US012595292B2

(12) United States Patent
Sahin et al.

(10) Patent No.: US 12,595,292 B2
(45) Date of Patent: Apr. 7, 2026

(54) INTERLEUKIN-2 RECEPTOR (IL2R) AND INTERLEUKIN-2 (IL2) VARIANTS FOR SPECIFIC ACTIVATION OF IMMUNE EFFECTOR CELLS

(71) Applicant: BioNTech Cell & Gene Therapies GmbH, Mainz (DE)

(72) Inventors: Ugur Sahin, Mainz (DE); Sina Fellermeier-Kopf, Mainz (DE); Alexander Muik, Mainz (DE); Matthias Birtel, Mainz (DE)

(73) Assignee: BIONTECH CELL & GENE THERAPIES GMBH, Mainz (DE)

( * ) Notice: Subject to any disclaimer, the term of this patent is extended or adjusted under 35 U.S.C. 154(b) by 1130 days.

(21) Appl. No.: 17/439,367

(22) PCT Filed: Mar. 16, 2020

(86) PCT No.: PCT/EP2020/057140
§ 371 (c)(1),
(2) Date: Sep. 14, 2021

(87) PCT Pub. No.: WO2020/187848
PCT Pub. Date: Sep. 24, 2020

(65) Prior Publication Data
US 2022/0177544 A1 Jun. 9, 2022

(30) Foreign Application Priority Data

Mar. 18, 2019 (WO) ................. PCT/EP2019/056719

(51) Int. Cl.

| | |
|---|---|
| *C07K 14/55* | (2006.01) |
| *A61K 38/20* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/715* | (2006.01) |
| *C12N 5/0783* | (2010.01) |

(52) U.S. Cl.
CPC ...... *C07K 14/7155* (2013.01); *A61K 38/2013* (2013.01); *A61K 40/11* (2025.01); *A61K 40/31* (2025.01); *A61K 40/4202* (2025.01); *A61P 35/00* (2018.01); *C07K 14/55* (2013.01); *C12N 5/0636* (2013.01); *A61K 2239/59* (2023.05); *C07K 2319/30* (2013.01)

(58) Field of Classification Search
None
See application file for complete search history.

(56) References Cited

U.S. PATENT DOCUMENTS

2008/0317746 A1 12/2008 Bauerle et al.

FOREIGN PATENT DOCUMENTS

| | | |
|---|---|---|
| RU | 2425054 C2 | 7/2011 |
| WO | 2005/086751 A2 | 9/2005 |
| WO | 2016/022671 A1 | 2/2016 |
| WO | 2017/044464 A1 | 3/2017 |
| WO | 2020/020783 A1 | 1/2020 |

OTHER PUBLICATIONS

Cosman, et al., (Dec. 1984) "Cloning, sequence and expression of human interleukin-2 receptor," Nature, 312: 768-771.
Kuznetsova—"Brackets in text of legal document as a linguistic and cognitive phenomenon," Institute of Humanities, Severodvisnk branch of Lomonosov Northern (Arctic) Federal University (2015) p. 37-43. English Abstract.
Rudikoff, et al. "Single amino acid substitution altering antigen-binding specificity." PNAS, 79: 1979-1983 (Mar. 1982).
Badri H. Optimization of radiation dosing schedules for proneural glioblastoma, J Math Bio, 2016, vol. 72, N. 5, pp. 1301-1336.
Baylot V. et al., TC TP Has a Crucial Role in the Different Stages of Prostate Cancer Malignant Progression, Results Probl cell Differ, 2017, vol. 64, pp. 255-261.
Abbas A. K., Murphy K. M., Sher A. Nature. Oct. 31, 1996 (vol. 383, No. 6603). pp. 787-793.
Roit A. et al., Immunology, Moscow, Mir, 2000, pp. 4-6 (with machine English translation).
Robb, R. J., et al., 1988, "Structure-function relationships for the interleukin 2 receptor: Location of ligand and antibody binding sites on the Tac receptor chain by mutational analysis", PNAS Immunology, 85(21), pp. 5654-5658.
GenBank, NP_000408.1, Feb. 10, 2019.
Sockolosky et al., Selective targeting of engineered T cells using orthogonal IL-2 cytokine-receptor complexes, Science, 2018, 359(6379), 1037-1042.
Minami et al., "The IL-2 Receptor Complex: Its Structure, Function, and Target Genes", Annual Review of Immunology, 1993, 11(1), 245-268.
International Search Report mailed May 13, 2020 in International Application No. PCT/EP2020/057140, 5 pages.

(Continued)

*Primary Examiner* — Michael D Pak

(74) *Attorney, Agent, or Firm* — McDonnell Boehnen Hulbert & Berghoff, LLP

(57) ABSTRACT

The invention relates to variants of the alpha subunit of interleukin-2 receptor (IL2R) and interleukin-2 (IL2). In one embodiment, the IL2 variants described herein have amino acid substitutions at the region of IL2 that contacts the alpha (α) subunit of the heterotrimeric IL2 receptor complex, IL2Rαβγ, reducing its ability to bind and activate the heterotrimeric receptor complex. Conversely, the corresponding IL2Rα variants described herein have amino acid substitutions compensating for such reduced ability of IL2 variants to bind to and activate IL2Rαβγ, preferably at amino acid residues contacted by IL2 amino acid residues that are substituted in the IL2 variants described herein.

16 Claims, 9 Drawing Sheets

Specification includes a Sequence Listing.

(56)         References Cited

OTHER PUBLICATIONS

Written Opinion mailed May 13, 2020 in International Application
No. PCT/EP2020/057140, 7 pages.
Rickert M et al., (Jun. 2005) "The structure of interleukin-2 complexed
with its alpha receptor." Science, 308 (5727): 1477-80.

A

B

A

B

A

B

A

B mock (CLDN18.2) CAR 28ζ

CLDN6 CAR 28ζ

A        hAlb

B        hAlb-hIL2_A3

C        hAlb-hIL2_A4

CLDN6 CAR BBζ

SEQUENCE LISTING

<160> NUMBER OF SEQ ID NOS: 17

<210> SEQ ID NO 1
<211> LENGTH: 133
<212> TYPE: PRT
<213> ORGANISM: Homo sapiens

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 2
<211> LENGTH: 251
<212> TYPE: PRT
<213> ORGANISM: Homo sapiens

<400> SEQUENCE: 2

```
Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
```

-continued

```
                    20                  25                  30

Gly Phe Arg Arg Ile Lys Ser Gly Ser Leu Tyr Met Leu Cys Thr Gly
                35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
                100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
                180                 185                 190

Leu Val Thr Thr Thr Asp Phe Gln Ile Gln Thr Glu Met Ala Ala Thr
            195                 200                 205

Met Glu Thr Ser Ile Phe Thr Thr Glu Tyr Gln Val Ala Val Ala Gly
        210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250
```

```
<210> SEQ ID NO 3
<211> LENGTH: 609
<212> TYPE: PRT
<213> ORGANISM: Homo sapiens

<400> SEQUENCE: 3

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
                35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
                100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140
```

-continued

```
Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
                180                 185                 190

Cys Gln Ala Ala Asp Lys Ala Ala Cys Leu Leu Pro Lys Leu Asp Glu
                195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
                355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
```

-continued

```
              565              570              575

Ala Phe Val Glu Lys Cys Cys Lys Ala Asp Asp Lys Glu Thr Cys Phe
            580              585              590

Ala Glu Glu Gly Lys Lys Leu Val Ala Ala Ser Gln Ala Ala Leu Gly
        595              600              605

Leu

<210> SEQ ID NO 4
<211> LENGTH: 272
<212> TYPE: PRT
<213> ORGANISM: Homo sapiens

<400> SEQUENCE: 4

Met Asp Ser Tyr Leu Leu Met Trp Gly Leu Leu Thr Phe Ile Met Val
1               5                  10                  15

Pro Gly Cys Gln Ala Glu Leu Cys Asp Asp Asp Pro Pro Glu Ile Pro
                20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
        50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
                100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
        130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
                180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
        210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 5
<211> LENGTH: 133
<212> TYPE: PRT
<213> ORGANISM: Artificial Sequence
<220> FEATURE:
<223> OTHER INFORMATION: hIL2_A3

<400> SEQUENCE: 5
```

-continued

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Glu Leu Thr Arg Met Leu Thr Phe Glu Phe Tyr Met Pro Lys
        35                  40                  45

Lys Ala Thr Glu Leu Lys His Leu Gln Cys Leu Glu Lys Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130
```

```
<210> SEQ ID NO 6
<211> LENGTH: 133
<212> TYPE: PRT
<213> ORGANISM: Artificial Sequence
<220> FEATURE:
<223> OTHER INFORMATION: hIL2_A4

<400> SEQUENCE: 6
```

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Glu Phe Tyr Met Pro Lys
        35                  40                  45

Lys Ala Thr Glu Leu Lys His Leu Gln Cys Leu Glu Lys Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130
```

```
<210> SEQ ID NO 7
<211> LENGTH: 133
<212> TYPE: PRT
<213> ORGANISM: Artificial Sequence
<220> FEATURE:
<223> OTHER INFORMATION: hIL2_A5

<400> SEQUENCE: 7
```

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

```
Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Lys Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 8
<211> LENGTH: 133
<212> TYPE: PRT
<213> ORGANISM: Artificial Sequence
<220> FEATURE:
<223> OTHER INFORMATION: hIL2_A8

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Glu Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 9
<211> LENGTH: 752
<212> TYPE: PRT
<213> ORGANISM: Artificial Sequence
<220> FEATURE:
<223> OTHER INFORMATION: hAlb-hIL2

<400> SEQUENCE: 9

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
```

-continued

```
            50                    55                    60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480
```

-continued

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu Gly Gly Ser Gly Gly Gly Gly Ser Gly Gly Ala Pro Thr Ser Ser
    610                 615                 620

Ser Thr Lys Lys Thr Gln Leu Gln Leu Glu His Leu Leu Leu Asp Leu
625                 630                 635                 640

Gln Met Ile Leu Asn Gly Ile Asn Asn Tyr Lys Asn Pro Lys Leu Thr
            645                 650                 655

Arg Met Leu Thr Phe Lys Phe Tyr Met Pro Lys Lys Ala Thr Glu Leu
            660                 665                 670

Lys His Leu Gln Cys Leu Glu Glu Glu Leu Lys Pro Leu Glu Glu Val
            675                 680                 685

Leu Asn Leu Ala Gln Ser Lys Asn Phe His Leu Arg Pro Arg Asp Leu
    690                 695                 700

Ile Ser Asn Ile Asn Val Ile Val Leu Glu Leu Lys Gly Ser Glu Thr
705                 710                 715                 720

Thr Phe Met Cys Glu Tyr Ala Asp Glu Thr Ala Thr Ile Val Glu Phe
            725                 730                 735

Leu Asn Arg Trp Ile Thr Phe Cys Gln Ser Ile Ile Ser Thr Leu Thr
            740                 745                 750

<210> SEQ ID NO 10
<211> LENGTH: 752
<212> TYPE: PRT
<213> ORGANISM: Artificial Sequence
<220> FEATURE:
<223> OTHER INFORMATION: hAlb-hIL2_A3

<400> SEQUENCE: 10

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
            85                  90                  95

-continued

```
Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
            130                 135                 140

Asp Val Met Cys Thr Ala Phe His Asp Asn Glu Glu Thr Phe Leu Lys
        145                 150                 155                 160

Lys Tyr Leu Tyr Glu Ile Ala Arg Arg His Pro Tyr Phe Tyr Ala Pro
                    165                 170                 175

Glu Leu Leu Phe Phe Ala Lys Arg Tyr Lys Ala Ala Phe Thr Glu Cys
                    180                 185                 190

Cys Gln Ala Ala Asp Lys Ala Ala Cys Leu Leu Pro Lys Leu Asp Glu
                    195                 200                 205

Leu Arg Asp Glu Gly Lys Ala Ser Ser Ala Lys Gln Arg Leu Lys Cys
            210                 215                 220

Ala Ser Leu Gln Lys Phe Gly Glu Arg Ala Phe Lys Ala Trp Ala Val
        225                 230                 235                 240

Ala Arg Leu Ser Gln Arg Phe Pro Lys Ala Glu Phe Ala Glu Val Ser
                    245                 250                 255

Lys Leu Val Thr Asp Leu Thr Lys Val His Thr Glu Cys Cys His Gly
                    260                 265                 270

Asp Leu Leu Glu Cys Ala Asp Asp Arg Ala Asp Leu Ala Lys Tyr Ile
                    275                 280                 285

Cys Glu Asn Gln Asp Ser Ile Ser Ser Lys Leu Lys Glu Cys Cys Glu
            290                 295                 300

Lys Pro Leu Leu Glu Lys Ser His Cys Ile Ala Glu Val Glu Asn Asp
        305                 310                 315                 320

Glu Met Pro Ala Asp Leu Pro Ser Leu Ala Ala Asp Phe Val Glu Ser
                    325                 330                 335

Lys Asp Val Cys Lys Asn Tyr Ala Glu Ala Lys Asp Val Phe Leu Gly
                    340                 345                 350

Met Phe Leu Tyr Glu Tyr Ala Arg Arg His Pro Asp Tyr Ser Val Val
                    355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
        385                 390                 395                 400

Phe Lys Pro Leu Val Glu Glu Pro Gln Asn Leu Ile Lys Gln Asn Cys
                    405                 410                 415

Glu Leu Phe Glu Gln Leu Gly Glu Tyr Lys Phe Gln Asn Ala Leu Leu
                    420                 425                 430

Val Arg Tyr Thr Lys Lys Val Pro Gln Val Ser Thr Pro Thr Leu Val
                    435                 440                 445

Glu Val Ser Arg Asn Leu Gly Lys Val Gly Ser Lys Cys Cys Lys His
            450                 455                 460

Pro Glu Ala Lys Arg Met Pro Cys Ala Glu Asp Tyr Leu Ser Val Val
        465                 470                 475                 480

Leu Asn Gln Leu Cys Val Leu His Glu Lys Thr Pro Val Ser Asp Arg
                    485                 490                 495

Val Thr Lys Cys Cys Thr Glu Ser Leu Val Asn Arg Arg Pro Cys Phe
                    500                 505                 510
```

-continued

---

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu Gly Gly Ser Gly Gly Gly Ser Gly Gly Ala Pro Thr Ser Ser
        610                 615                 620

Ser Thr Lys Lys Thr Gln Leu Gln Leu Glu His Leu Leu Leu Asp Leu
625                 630                 635                 640

Gln Met Ile Leu Asn Gly Ile Asn Asn Tyr Lys Asn Pro Glu Leu Thr
                645                 650                 655

Arg Met Leu Thr Phe Glu Phe Tyr Met Pro Lys Lys Ala Thr Glu Leu
                660                 665                 670

Lys His Leu Gln Cys Leu Glu Lys Glu Leu Lys Pro Leu Glu Glu Val
                675                 680                 685

Leu Asn Leu Ala Gln Ser Lys Asn Phe His Leu Arg Pro Arg Asp Leu
        690                 695                 700

Ile Ser Asn Ile Asn Val Ile Val Leu Glu Leu Lys Gly Ser Glu Thr
705                 710                 715                 720

Thr Phe Met Cys Glu Tyr Ala Asp Glu Thr Ala Thr Ile Val Glu Phe
                725                 730                 735

Leu Asn Arg Trp Ile Thr Phe Cys Gln Ser Ile Ile Ser Thr Leu Thr
                740                 745                 750

<210> SEQ ID NO 11
<211> LENGTH: 752
<212> TYPE: PRT
<213> ORGANISM: Artificial Sequence
<220> FEATURE:
<223> OTHER INFORMATION: hAlb-hIL2_A4

<400> SEQUENCE: 11

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
                100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys

```
545                550                555                560

Pro Lys Ala Thr Lys Glu Gln Leu Lys Ala Val Met Asp Asp Phe Ala
                 565                570                575

Ala Phe Val Glu Lys Cys Cys Lys Ala Asp Asp Lys Glu Thr Cys Phe
                 580                585                590

Ala Glu Glu Gly Lys Lys Leu Val Ala Ala Ser Gln Ala Ala Leu Gly
                 595                600                605

Leu Gly Gly Ser Gly Gly Gly Ser Gly Gly Ala Pro Thr Ser Ser
                 610                615                620

Ser Thr Lys Lys Thr Gln Leu Gln Leu Glu His Leu Leu Leu Asp Leu
625                630                635                640

Gln Met Ile Leu Asn Gly Ile Asn Asn Tyr Lys Asn Pro Lys Leu Thr
                 645                650                655

Arg Met Leu Thr Phe Glu Phe Tyr Met Pro Lys Lys Ala Thr Glu Leu
                 660                665                670

Lys His Leu Gln Cys Leu Glu Lys Glu Leu Lys Pro Leu Glu Glu Val
                 675                680                685

Leu Asn Leu Ala Gln Ser Lys Asn Phe His Leu Arg Pro Arg Asp Leu
                 690                695                700

Ile Ser Asn Ile Asn Val Ile Val Leu Glu Leu Lys Gly Ser Glu Thr
705                710                715                720

Thr Phe Met Cys Glu Tyr Ala Asp Glu Thr Ala Thr Ile Val Glu Phe
                 725                730                735

Leu Asn Arg Trp Ile Thr Phe Cys Gln Ser Ile Ile Ser Thr Leu Thr
                 740                745                750
```

```
<210> SEQ ID NO 12
<211> LENGTH: 752
<212> TYPE: PRT
<213> ORGANISM: Artificial Sequence
<220> FEATURE:
<223> OTHER INFORMATION: hAlb-hIL2_A5

<400> SEQUENCE: 12

Met Lys Trp Val Thr Phe Ile Ser Leu Leu Phe Leu Phe Ser Ser Ala
1                5                  10                 15

Tyr Ser Arg Gly Val Phe Arg Arg Asp Ala His Lys Ser Glu Val Ala
                 20                 25                 30

His Arg Phe Lys Asp Leu Gly Glu Glu Asn Phe Lys Ala Leu Val Leu
                 35                 40                 45

Ile Ala Phe Ala Gln Tyr Leu Gln Gln Cys Pro Phe Glu Asp His Val
                 50                 55                 60

Lys Leu Val Asn Glu Val Thr Glu Phe Ala Lys Thr Cys Val Ala Asp
65                70                 75                 80

Glu Ser Ala Glu Asn Cys Asp Lys Ser Leu His Thr Leu Phe Gly Asp
                 85                 90                 95

Lys Leu Cys Thr Val Ala Thr Leu Arg Glu Thr Tyr Gly Glu Met Ala
                 100                105                110

Asp Cys Cys Ala Lys Gln Glu Pro Glu Arg Asn Glu Cys Phe Leu Gln
                 115                120                125

His Lys Asp Asp Asn Pro Asn Leu Pro Arg Leu Val Arg Pro Glu Val
                 130                135                140

Asp Val Met Cys Thr Ala Phe His Asp Asn Glu Glu Thr Phe Leu Lys
145                150                155                160

Lys Tyr Leu Tyr Glu Ile Ala Arg Arg His Pro Tyr Phe Tyr Ala Pro
```

-continued

```
                    165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
            580                 585                 590
```

```
Ala Glu Glu Gly Lys Lys Leu Val Ala Ala Ser Gln Ala Ala Leu Gly
        595             600             605

Leu Gly Gly Ser Gly Gly Gly Gly Ser Gly Gly Ala Pro Thr Ser Ser
    610             615             620

Ser Thr Lys Lys Thr Gln Leu Gln Leu Glu His Leu Leu Leu Asp Leu
625             630             635             640

Gln Met Ile Leu Asn Gly Ile Asn Asn Tyr Lys Asn Pro Lys Leu Thr
            645             650             655

Arg Met Leu Thr Phe Lys Phe Tyr Met Pro Lys Lys Ala Thr Glu Leu
        660             665             670

Lys His Leu Gln Cys Leu Glu Lys Glu Leu Lys Pro Leu Glu Glu Val
        675             680             685

Leu Asn Leu Ala Gln Ser Lys Asn Phe His Leu Arg Pro Arg Asp Leu
        690             695             700

Ile Ser Asn Ile Asn Val Ile Val Leu Glu Leu Lys Gly Ser Glu Thr
705             710             715             720

Thr Phe Met Cys Glu Tyr Ala Asp Glu Thr Ala Thr Ile Val Glu Phe
            725             730             735

Leu Asn Arg Trp Ile Thr Phe Cys Gln Ser Ile Ile Ser Thr Leu Thr
            740             745             750
```

<210> SEQ ID NO 13
<211> LENGTH: 752
<212> TYPE: PRT
<213> ORGANISM: Artificial Sequence
<220> FEATURE:
<223> OTHER INFORMATION: hAlb-hIL2_A8

<400> SEQUENCE: 13

```
Met Lys Trp Val Thr Phe Ile Ser Leu Leu Phe Leu Phe Ser Ser Ala
1               5               10              15

Tyr Ser Arg Gly Val Phe Arg Arg Asp Ala His Lys Ser Glu Val Ala
            20              25              30

His Arg Phe Lys Asp Leu Gly Glu Glu Asn Phe Lys Ala Leu Val Leu
        35              40              45

Ile Ala Phe Ala Gln Tyr Leu Gln Gln Cys Pro Phe Glu Asp His Val
    50              55              60

Lys Leu Val Asn Glu Val Thr Glu Phe Ala Lys Thr Cys Val Ala Asp
65              70              75              80

Glu Ser Ala Glu Asn Cys Asp Lys Ser Leu His Thr Leu Phe Gly Asp
            85              90              95

Lys Leu Cys Thr Val Ala Thr Leu Arg Glu Thr Tyr Gly Glu Met Ala
            100             105             110

Asp Cys Cys Ala Lys Gln Glu Pro Glu Arg Asn Glu Cys Phe Leu Gln
        115             120             125

His Lys Asp Asp Asn Pro Asn Leu Pro Arg Leu Val Arg Pro Glu Val
        130             135             140

Asp Val Met Cys Thr Ala Phe His Asp Asn Glu Glu Thr Phe Leu Lys
145             150             155             160

Lys Tyr Leu Tyr Glu Ile Ala Arg Arg His Pro Tyr Phe Tyr Ala Pro
            165             170             175

Glu Leu Leu Phe Phe Ala Lys Arg Tyr Lys Ala Ala Phe Thr Glu Cys
            180             185             190

Cys Gln Ala Ala Asp Lys Ala Ala Cys Leu Leu Pro Lys Leu Asp Glu
        195             200             205
```

-continued

```
Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
                275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
                355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
                435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
            595                 600                 605

Leu Gly Gly Ser Gly Gly Gly Gly Ser Gly Gly Ala Pro Thr Ser Ser
    610                 615                 620
```

```
Ser Thr Lys Lys Thr Gln Leu Gln Leu Glu His Leu Leu Leu Asp Leu
625                 630                 635                 640

Gln Met Ile Leu Asn Gly Ile Asn Asn Tyr Lys Asn Pro Lys Leu Thr
                    645                 650                 655

Arg Met Leu Thr Phe Glu Phe Tyr Met Pro Lys Lys Ala Thr Glu Leu
                660                 665                 670

Lys His Leu Gln Cys Leu Glu Glu Glu Leu Lys Pro Leu Glu Glu Val
            675                 680                 685

Leu Asn Leu Ala Gln Ser Lys Asn Phe His Leu Arg Pro Arg Asp Leu
            690                 695                 700

Ile Ser Asn Ile Asn Val Ile Val Leu Glu Leu Lys Gly Ser Glu Thr
705                 710                 715                 720

Thr Phe Met Cys Glu Tyr Ala Asp Glu Thr Ala Thr Ile Val Glu Phe
                725                 730                 735

Leu Asn Arg Trp Ile Thr Phe Cys Gln Ser Ile Ile Ser Thr Leu Thr
                740                 745                 750
```

```
<210> SEQ ID NO 14
<211> LENGTH: 272
<212> TYPE: PRT
<213> ORGANISM: Artificial Sequence
<220> FEATURE:
<223> OTHER INFORMATION: hIL2RA_mut1

<400> SEQUENCE: 14
```

```
Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
                20                  25                  30

His Ala Thr Phe Lys Ala Met Ala Tyr Lys Glu Gly Thr Met Leu Asn
            35                  40                  45

Cys Lys Cys Lys Arg Gly Phe Arg Arg Ile Glu Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
                100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
                180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240
```

-continued

```
Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 15
<211> LENGTH: 272
<212> TYPE: PRT
<213> ORGANISM: Artificial Sequence
<220> FEATURE:
<223> OTHER INFORMATION: hIL2RA_mut2

<400> SEQUENCE: 15

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Glu Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
            130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 16
<211> LENGTH: 272
<212> TYPE: PRT
<213> ORGANISM: Artificial Sequence
<220> FEATURE:
<223> OTHER INFORMATION: hIL2RA_mut3

<400> SEQUENCE: 16

Met Asp Ser Tyr Leu Leu Met Trp Gly Leu Leu Thr Phe Ile Met Val
1               5                   10                  15
```

-continued

```
Pro Gly Cys Gln Ala Glu Leu Cys Asp Asp Asp Pro Pro Glu Ile Pro
            20              25              30

His Ala Thr Phe Lys Ala Met Ala Tyr Lys Glu Gly Thr Met Leu Asn
            35              40              45

Cys Lys Cys Lys Arg Gly Phe Arg Arg Ile Lys Ser Gly Ser Leu Tyr
    50              55              60

Met Leu Cys Thr Gly Asn Ser Ser His Ser Ser Trp Asp Asn Gln Cys
65              70              75              80

Gln Cys Thr Ser Ser Ala Thr Arg Asn Thr Thr Lys Gln Val Thr Pro
            85              90              95

Gln Pro Glu Glu Gln Lys Glu Arg Lys Thr Thr Glu Met Gln Ser Pro
            100             105             110

Met Gln Pro Val Asp Gln Ala Ser Leu Pro Gly His Cys Arg Glu Pro
            115             120             125

Pro Pro Trp Glu Asn Glu Ala Thr Glu Arg Ile Tyr His Phe Val Val
    130             135             140

Gly Gln Met Val Tyr Tyr Gln Cys Val Gln Gly Tyr Arg Ala Leu His
145             150             155             160

Arg Gly Pro Ala Glu Ser Val Cys Lys Met Thr His Gly Lys Thr Arg
            165             170             175

Trp Thr Gln Pro Gln Leu Ile Cys Thr Gly Glu Met Glu Thr Ser Gln
            180             185             190

Phe Pro Gly Glu Glu Lys Pro Gln Ala Ser Pro Glu Gly Arg Pro Glu
            195             200             205

Ser Glu Thr Ser Cys Leu Val Thr Thr Thr Asp Phe Gln Ile Gln Thr
    210             215             220

Glu Met Ala Ala Thr Met Glu Thr Ser Ile Phe Thr Thr Glu Tyr Gln
225             230             235             240

Val Ala Val Ala Gly Cys Val Phe Leu Leu Ile Ser Val Leu Leu Leu
            245             250             255

Ser Gly Leu Thr Trp Gln Arg Arg Gln Arg Lys Ser Arg Arg Thr Ile
            260             265             270
```

<210> SEQ ID NO 17
<211> LENGTH: 272
<212> TYPE: PRT
<213> ORGANISM: Artificial Sequence
<220> FEATURE:
<223> OTHER INFORMATION: hIL2RA_mut4

<400> SEQUENCE: 17

```
Met Asp Ser Tyr Leu Leu Met Trp Gly Leu Leu Thr Phe Ile Met Val
1               5               10              15

Pro Gly Cys Gln Ala Lys Leu Cys Asp Asp Asp Pro Pro Glu Ile Pro
            20              25              30

His Ala Thr Phe Lys Ala Met Ala Tyr Lys Glu Gly Thr Met Leu Asn
            35              40              45

Cys Lys Cys Lys Arg Gly Phe Arg Arg Ile Glu Ser Gly Ser Leu Tyr
    50              55              60

Met Leu Cys Thr Gly Asn Ser Ser His Ser Ser Trp Asp Asn Gln Cys
65              70              75              80

Gln Cys Thr Ser Ser Ala Thr Arg Asn Thr Thr Lys Gln Val Thr Pro
            85              90              95

Gln Pro Glu Glu Gln Lys Glu Arg Lys Thr Thr Glu Met Gln Ser Pro
            100             105             110
```

-continued

```
Met Gln Pro Val Asp Gln Ala Ser Leu Pro Gly His Cys Arg Glu Pro
        115             120             125

Pro Pro Trp Glu Asn Glu Ala Thr Glu Arg Ile Tyr His Phe Val Val
    130             135             140

Gly Gln Met Val Tyr Tyr Gln Cys Val Gln Gly Tyr Arg Ala Leu His
145             150             155             160

Arg Gly Pro Ala Glu Ser Val Cys Lys Met Thr His Gly Lys Thr Arg
            165             170             175

Trp Thr Gln Pro Gln Leu Ile Cys Thr Gly Glu Met Glu Thr Ser Gln
            180             185             190

Phe Pro Gly Glu Glu Lys Pro Gln Ala Ser Pro Glu Gly Arg Pro Glu
        195             200             205

Ser Glu Thr Ser Cys Leu Val Thr Thr Thr Asp Phe Gln Ile Gln Thr
    210             215             220

Glu Met Ala Ala Thr Met Glu Thr Ser Ile Phe Thr Thr Glu Tyr Gln
225             230             235             240

Val Ala Val Ala Gly Cys Val Phe Leu Leu Ile Ser Val Leu Leu Leu
            245             250             255

Ser Gly Leu Thr Trp Gln Arg Arg Gln Arg Lys Ser Arg Arg Thr Ile
            260             265             270
```

INTERLEUKIN-2 RECEPTOR (IL2R) AND INTERLEUKIN-2 (IL2) VARIANTS FOR SPECIFIC ACTIVATION OF IMMUNE EFFECTOR CELLS

CROSS REFERENCE TO RELATED APPLICATION(S)

This application is a U.S. National Phase of International Application No. PCT/EP2020/057140, filed on Mar. 16, 2020, which claims priority to International Application No. PCT/EP2019/056719, filed Mar. 18, 2019 all of which are incorporated by reference herein in their entirety.

TECHNICAL FIELD

The invention relates to variants of the alpha subunit of interleukin-2 receptor (IL2R) and interleukin-2 (IL2). In one embodiment, the IL2 variants described herein have amino acid substitutions at the region of IL2 that contacts the alpha (α) subunit of the heterotrimeric IL2 receptor complex, IL2Rαβγ, reducing its ability to bind and activate the heterotrimeric receptor complex. Conversely, the corresponding IL2Rα variants described herein have amino acid substitutions compensating for such reduced ability of IL2 variants to bind to and activate IL2Rαβγ, preferably at amino acid residues contacted by IL2 amino acid residues that are substituted in the IL2 variants described herein. The IL2 variants show impaired binding to and/or activation of wild type IL2R, i.e., IL2R comprising the (wild type) alpha subunit of IL2R. However, variation in the alpha subunit of IL2R at least partially restores binding to and/or activation of IL2R comprising a variant of the alpha subunit of IL2R. Thus, described herein are pairs, sets or systems of corresponding variants of alpha subunits of IL2R and IL2 which show a level of binding and/or activation which exceeds the level of binding and/or activation shown by the variants of IL2 and wild type IL2Rαβγ.

In particular, described herein are receptor polypeptides comprising a mutein of the alpha subunit of interleukin-2 receptor (IL2R) or of a functional variant of the alpha subunit of IL2R, wherein the alpha subunit of IL2R or the functional variant thereof is substituted at at least a position having an acidic amino acid residue in wild type alpha subunit of IL2R that contacts a basic amino acid residue in wild type IL2 and/or is substituted at at least a position having a basic amino acid residue in wild type alpha subunit of IL2R that contacts an acidic amino acid residue in wild type IL2. If the amino acid residue is an acidic amino acid residue in wild type alpha subunit of IL2R the substitution is by a basic amino acid residue. If the amino acid residue is a basic amino acid residue in wild type alpha subunit of IL2R the substitution is by an acidic amino acid residue. Also described are polynucleotides encoding the receptor polypeptides described herein, host cells, in particular immune effector cells such as T cells genetically modified to express a receptor polypeptide described herein, and pharmaceutical compositions and medical preparations comprising the polynucleotides and host cells.

Also described are respective ligand polypeptides comprising a mutein of IL2 or of a functional variant of IL2, wherein when the alpha subunit of IL2R or the functional variant thereof is substituted at at least a position having an acidic amino acid residue in wild type alpha subunit of IL2R that contacts a basic amino acid residue in wild type IL2, the IL2 or the functional variant thereof is substituted at at least said basic amino acid residue in wild type IL2 and/or when the alpha subunit of IL2R or the functional variant thereof is substituted at at least a position having a basic amino acid residue in wild type alpha subunit of IL2R that contacts an acidic amino acid residue in wild type IL2, the IL2 or the functional variant thereof is substituted at at least said acidic amino acid residue in wild type IL2. If the amino acid residue is a basic amino acid residue in wild type IL2 the substitution is by an acidic amino acid residue. If the amino acid residue is an acidic amino acid residue in wild type IL2 the substitution is by a basic amino acid residue.

Immune effector cells such as T cells harboring wild type IL2R will show reduced responsiveness when contacted with IL2 variants described herein. However, responsiveness of corresponding immune effector cells such as T cells harboring a variant IL2R (IL2R comprising an IL2Rα variant polypeptide) will be restored, at least partially. Pairs, sets or systems of corresponding variants of alpha subunits of IL2R and IL2 may be used to specifically activate immune effector cells such as T cells harboring a variant IL2R described herein. Such immune effector cells such as T cells harboring a variant IL2R described herein may be generated ex vivo or in vitro and subsequently administered to a subject in need of treatment or may be generated in vivo in a subject in need of treatment. Thus, the present disclosure also relates to methods and agents for enhancing the effect of immune effector cells such as T cells. Specifically, the present disclosure relates to methods comprising providing to a subject immune effector cells genetically modified to express a variant IL2R described herein and providing to the subject the corresponding IL2 variant, e.g., by administering to the subject the corresponding IL2 variant, a polynucleotide encoding the corresponding IL2 variant or a host cell genetically modified to express the corresponding IL2 variant. The methods and agents described herein are, in particular, useful for the treatment of diseases characterized by diseased cells expressing an antigen the immune effector cells are directed to. In one embodiment, the immune effector cells carry an antigen receptor such as T cell receptor (TCR) or chimeric antigen receptor (CAR) having a binding specificity for the antigen or a procession product thereof. In one embodiment, the immune effector cells are genetically modified to express the antigen receptor. Such genetic modification may be effected ex vivo or in vitro and subsequently the immune effector cells may be administered to a subject in need of treatment or may be effected in vivo in a subject in need of treatment.

BACKGROUND

The immune system plays an important role in cancer, autoimmunity, allergy as well as in pathogen-associated diseases. T cells and NK cells are important mediators of anti-tumor immune responses. CD8+ T cells and NK cells can directly lyse tumor cells. CD4+ T cells, on the other hand, can mediate the influx of different immune subsets including CD8+ T cells and NK cells into the tumor. CD4+ T cells are able to license dendritic cells (DCs) for the priming of anti-tumor CD8+ T cell responses and can act directly on tumor cells via IFNγ mediated MHC upregulation and growth inhibition. CD8+ as well as CD4+ tumor specific T-cell responses can be induced via vaccination or by adoptive transfer of T cells.

Adoptive cell transfer (ACT) based immunotherapy can be broadly defined as a form of passive immunization with previously sensitized T cells that are transferred to non-immune recipients or to the autologous host after ex vivo expansion from low precursor frequencies to clinically relevant cell numbers. Cell types that have been used for ACT experiments are lymphokine-activated killer (LAK) cells (Mule, J. J. et al. (1984) Science 225, 1487-1489; Rosenberg, S. A. et al. (1985) N. Engl. J. Med. 313, 1485-1492), tumor-infiltrating lymphocytes (TILs) (Rosenberg, S. A. et al. (1994) J. Natl. Cancer Inst. 86, 1159-1166), donor lymphocytes after hematopoietic stem cell transplantation (HSCT) as well as tumor-specific T cell lines or clones (Dudley, M. E. et al. (2001) J. Immunother. 24, 363-373; Yee, C. et al. (2002) Proc. Natl. Acad. Sci. U.S.A 99, 16168-16173). An alternative approach is the adoptive transfer of autologous T cells reprogrammed to express a tumor-reactive immunoreceptor of defined specificity during short-time ex vivo culture followed by reinfusion into the patient (Kershaw M. H. et al. (2013) Nature Reviews Cancer 13 (8):525-41). This strategy makes ACT applicable to a variety of common malignancies even if tumor-reactive T cells are absent in the patient. For example, adoptive transfer of chimeric antigen receptor modified T cells (CAR T cells) is investigated in an extensive number of clinical trials world-wide. Chimeric antigen receptors (CARs) are a type of antigen-targeted receptor composed of intracellular T cell signaling domains fused to extracellular antigen-binding moieties, most commonly single-chain variable fragments (scFvs) from monoclonal antibodies. CARs directly recognize cell surface antigens, independent of MHC-mediated presentation, permitting the use of a single receptor construct specific for any given antigen in all patients. CARs fuse antigen-recognition domains to the CD3$\zeta$ activation chain of the T cell receptor (TCR) complex and comprise secondary costimulatory signals in tandem with CD3$\zeta$, including intracellular domains from CD28 or a variety of TNF receptor family molecules such as 4-1BB (CD137) and OX40 (CD134). CARs dramatically improved antitumor efficacy, showing remarkable clinical efficacy especially in patients suffering from hematological malignancies (Hartmann, J. et al. EMBO Mol. Med. 9, 1183-1197 (2017)). Recently, two CAR T-cell therapies have received approval for the treatment of B-cell acute lymphoblastic leukaemia (Kymiah®) and diffuse large B-cell lymphoma (Yescarta®) by the FDA and EMA (Zheng, P. et al. Drug. Discov. Today 6, 1175-1182 (2018)). For solid tumors adoptive transfer of T cells, however, has shown limited efficacy so far and requires improvement (Newick, K. et al. Annu. Rev. Med. 68, 139-152 (2017)).

It is generally thought that robust in vivo expansion and persistence of tumor-reactive immunoreceptor-modified T cells are critical predictors of durable clinical remissions in patients with hematological malignancies (Guedan, S. et al. JCI Insight. 3 (1) (2018); Maude, S L. et al. N Engl J Med. 371, 1507-1517 (2014)). It can be presumed that the same is true for patients with solid tumors. Therefore, it would be desirable to support persistence or even expand therapeutically active cell clones in the patient.

One potential way of further improving clinical efficacy of immunoreceptor-modified T cells is the support and modulation of said cells via cytokines which affect cell survival and function. Hence, administration of cytokines crucial for survival can minimize the need for accompanying harsh lymphodepleting therapy like chemo- or radiotherapy, which is successfully used to increase persistence of adoptively transferred T cells (Maus, M. et al. Clin. Cancer Res. 22(8), 1875-1884 (2016)) by setting free survival signals like IL15 and IL7 otherwise consumed by resident immune cells (Gattinoni, L. et al. J. Exp. Med. 202, 907-12 (2005)). Moreover, the therapeutic potential of transferred cells can be enhanced by simultaneous administration of relevant cytokines. For example, interleukin-2 (IL2) is a potent immune stimulator, activating diverse cells of the immune system. IL2 is known to support the differentiation, proliferation, survival and effector functions of T cells and NK cells (Blattman, J. N. et al. Nat. Med. 9, 540-7 (2003)) and has been used for decades in the treatment of late stage malignant melanoma (Maas, R. A., Dullens, H. F. & Den Otter, W. Cancer Immunol. Immunother. 36, 141-8 (1993)).

However, there are several difficulties regarding the administration of cytokines for support of ACT:

(1) Recombinant cytokines have a very short plasma half-life creating the necessity to frequently inject high amounts of cytokine. In case of IL2 this leads to severe side effects such as vascular leak syndrome (VLS) (Rosenberg, S. A. et al. N. Engl. J. Med. 316, 889-97 (1987)).

(2) Immune cells generally compete for survival signals. Hence, administered cytokines are consumed by and influence both resident immune cells as well as transferred cells. As transferred cells are in the minority, mostly resident immune cells will be affected. This not only limits cytokine efficacy on ACT but also requires concomitant lymphoablative therapies (Gattinoni, L. et al. J. Exp. Med. 202, 907-12 (2005)).

(3) Cytokine administration might cause unwanted effects on resident immune ceils. For example, IL2 is known for its ability to stimulate regulatory T cells (Tregs) more potently than effector T cells (Todd, J. A. et al. PLoS Med. 13, e1002139 (2016)), as the high-affinity IL2 receptor (IL2R$\alpha\beta\gamma$) consisting of CD25 (IL2R$\alpha$), CD122 (IL2R$\beta$) and CD132 (IL2R$\gamma$) is expressed on Tregs as well as activated CD4$^+$ and CD8$^+$ T cells, while the intermediate-affinity receptor (IL2R$\beta\gamma$), which lacks CD25, is prevalent on naïve and memory T cells as well as NK cells. Tregs are correlated with reduced survival of cancer patients as they can suppress the function of anti-tumor effector T cells and NK cells (Nishikawa, H. & Sakaguchi. Curr. Opin. Immunol. 27, 1-7 (2014)). Attempts to alter IL2 in such a way that it loses preference for CD25 expressing cells, thereby relatively increasing the stimulatory potential on naïve and memory T cells as well as NK cells was shown to improve its anti-tumoral potential (Arenas-Ramirez, N. et al. Sci. Transl. Med. 8, 1-13 (2016)).

Clearly, there is a need for novel strategies to increase the effectiveness of immunotherapies, in particular cell-based cancer immunotherapies such as autologous TIL or TCR- or CAR-transgenic T cell based treatments and/or vaccines, in particular cancer vaccines. In order to address the limitations occurring when combining ACT or in vivo reprogramming of immune cells with cytokine therapy, we herein provide sets of variants of IL2R, in particular variants of the $\alpha$ subunit of IL2R, and variants of IL2. The IL2 variants described herein preferentially activate cells which express the corresponding variant $\alpha$ subunit of IL2R in relation to cells which express the wild type $\alpha$ subunit of IL2R. Adoptively transferred immune effector cells or in vivo genetically modified immune effector cells harboring a variant 2R are selectively targeted by the corresponding IL2 variant, while off-target effects on unmodified host immune cells are limited. Consequently, the novel variant pairs of IL2 and IL2R offer the ability to potently modulate survival and effector function of transferred cells leading to improved therapeutic efficacy.

SUMMARY

The present disclosure provides novel variant pairs of IL2 and IL2R. Specifically, variants of IL2 are described that contain mutations affecting CD25 binding ("mutCD25"). Corresponding variants of IL2Rα compensate for the affected CD25 binding of IL2 variants. Disruption of the interactions of IL2 with IL2Rα through appropriate modification of specific binding residues on the binding surface of IL2 was hypothesized to prevent effective binding (and thus activation) to cells expressing IL2Rαβγ. However, on cells expressing IL2Rαβγ comprising the corresponding variant α subunit of IL2R binding (and thus activation) to the cells will occur. An IL2 variant able to selectively activate IL2Rαβγ comprising the corresponding variant α subunit of IL2R on immune effector cells, e.g., T cells such as memory T cells, naïve T cells and effector T cells as well as NK cells, in preference to cells expressing wild type IL2Rαβγ is expected to have an improved therapeutic index over wild type IL2 and a reduced toxicity profile. An IL2 variant with an improved therapeutic index would have a significantly expanded range of use in the treatment of disorders requiring immune system stimulation, for example in the treatment of cancer (as a direct and/or adjunct therapy). In particular, administration of IL2 variant RNA is a promising approach to boost the therapeutic efficacy of multiple T and NK cell-based (cancer) immunotherapies.

Immune effector cells harboring a variant IL2R described herein may be generated in vitro and subsequently administered to a subject in need of treatment or may be generated in vivo in a subject in need of treatment. Administering to the subject the corresponding IL2 variant, a polynucleotide encoding the corresponding IL2 variant or a host cell genetically modified to express the corresponding IL2 variant allows for the specific stimulation of receptor-engineered immune effector cells. The methods and agents described herein are, in particular, useful for the treatment of diseases characterized by diseased cells expressing an antigen the immune effector cells are directed to. In one embodiment, the immune effector cells carry an antigen receptor such a T cell receptor (TCR) or chimeric antigen receptor (CAR) having a binding specificity for the antigen or a procession product thereof. In one embodiment, the immune effector cells are present in a subject to be treated and are genetically modified in vivo in the subject to express a receptor polypeptide described herein. In one embodiment, immune effector cells either from a subject to be treated or from a different subject are administered to the subject to be treated. The administered immune effector cells may be genetically modified ex vivo prior to administration or genetically modified in vivo in the subject following administration to express a receptor polypeptide described herein. In one embodiment, an antigen receptor is endogenous to the immune effector cells. In one embodiment, the immune effector cells are genetically modified, ex vivo or in vivo, to express the antigen receptor. Thus, such genetic modification with antigen receptor may be effected in vitro (optionally together with genetic modification by the IL2 receptor polypeptides described herein) and subsequently the immune effector cells administered to a subject in need of treatment or may be effected in vivo (optionally together with genetic modification by the IL2 receptor polypeptides described herein) in a subject in need of treatment. Thus, in one aspect, the present invention generally embraces the treatment of diseases by targeting cells expressing an antigen such as diseased cells, in particular cancer cells expressing a tumor antigen. The target cells may express the antigen on the cell surface or may present a procession product of the antigen. In one embodiment, the antigen is a tumor-associated antigen and the disease is cancer. Such treatment provides for the selective eradication of cells that express an antigen, thereby minimizing adverse effects to normal cells not expressing the antigen. In one embodiment, vaccine antigen or polynucleotide coding therefor is administered to provide (optionally following expression of the polynucleotide by appropriate target cells) antigen for stimulation, priming and/or expansion of the immune effector cells, wherein the immune effector cells (optionally genetically modified to express an antigen receptor) are targeted to the antigen or a procession product thereof and the immune response is an immune response to a target cell population or target tissue expressing the antigen. In one embodiment, the polynucleotide encoding the vaccine antigen is RNA. Immune effector cells such as T cells stimulated, primed and/or expanded in the patient are able to recognize cells expressing an antigen resulting in the eradication of diseased cells. The methods and agents described herein are particularly effective if RNA encoding IL2 variants is targeted to the liver for systemic availability. Liver cells can be efficiently transfected and are able to produce large amounts of protein. Antigen-encoding RNA is preferably targeted to secondary lymphoid organs.

Accordingly, one aspect relates to systems of alpha subunit of interleukin-2 receptor (IL2Rα) and interleukin-2 (IL2) variants for specific activation of immune effector cells in the treatment of diseases where such immune effector cells can be effective such as cancer including but not limited to solid tumors. In one embodiment, the present invention relates to a strategy of adoptive cell transfer of cells such as T cells transduced to express a CAR. CARs are molecules that combine specificity for a desired antigen (e.g., tumor antigen) which preferably is antibody-based with a T cell receptor-activating intracellular domain to generate a chimeric protein that exhibits a specific cellular immune activity (e.g., a specific anti-tumor cellular immune activity). Preferably, a cell can be genetically modified to stably express a CAR (and an IL2 receptor polypeptide described herein) on its surface, conferring novel antigen specificity that is MHC independent. T cells expressing a CAR are referred to herein as CAR T cells or CAR-modified T cells.

One aspect of the invention relates to a system comprising:

(i) a receptor polypeptide comprising a mutein of the alpha subunit of interleukin-2 receptor (IL2R) or of a functional variant of the alpha subunit of IL2R, wherein the alpha subunit of IL2R or the functional variant thereof is substituted at at least one position, (ii) a ligand polypeptide comprising a mutein of IL2 or of afunctional variant of IL2, wherein the IL2 or the functional variant thereof is substituted at at least one position, wherein the substitutions are such that (a) the mutein under (i) binds to and activates IL2R comprising the mutein under (i) as alpha subunit, and (b) binding to and/or activation of IL2R comprising the mutein under (i) as alpha subunit by the mutein under (ii) exceeds binding to and/or activation of IL2R comprising the alpha subunit of IL2R or the functional variant thereof as alpha subunit by the mutein under (ii).

In one embodiment, binding to and/or activation of IL2R comprising the mutein under (i) as alpha subunit by the mutein under (d) exceeds binding to and/or activation of IL2R comprising the mutein under (i) as alpha subunit by IL2 or the functional variant thereof. In one embodiment, binding to and/or activation of IL2R comprising the alpha subunit of IL2R or the functional variant thereof as alpha subunit by IL2 or the functional variant thereof exceeds binding to and/or activation of IL2R comprising the alpha subunit of IL2R or the functional variant thereof as alpha subunit by the mutein under (ii). In one embodiment, binding to and/or activation of IL2R comprising the alpha subunit of IL2R or the functional variant thereof as alpha subunit by IL2 or the functional variant thereof exceeds binding to and/or activation of IL2R comprising the mutein under (I) as alpha subunit by IL2 or the functional variant thereof.

In one embodiment, the system of the invention comprises (i) a receptor polypeptide comprising a mutein of the alpha subunit of IL2R or of afunctional variant of the alpha subunit of IL2R, wherein the alpha subunit of IL2R or the functional variant thereof is substituted at at least a position having an acidic amino acid residue in wild type alpha subunit of IL2R that contacts a basic amino acid residue in wild type IL2 and/or is substituted at at least a position having a basic amino acid residue in wild type alpha subunit of IL2R that contacts an acidic amino acid residue in wild type IL2, wherein if the amino acid residue is an acidic amino acid residue in wild type alpha subunit of IL2R the substitution is by a basic amino acid residue and if the amino acid residue is a basic amino acid residue in wild type alpha subunit of IL2R the substitution is by an acidic amino acid residue, (ii) a ligand polypeptide comprising a mutein of IL2 or of a functional variant of IL2, wherein when the alpha subunit of IL2R or the functional variant thereof is substituted at at least a position having an acidic amino acid residue in wild type alpha subunit of IL2R that contacts a basic amino acid residue in wild type IL2, the IL2 or the functional variant thereof is substituted at at least said basic amino acid residue in wild type IL2 and/or when the alpha subunit of IL2R or the functional variant thereof is substituted at at least a position having a basic amino acid residue in wild type alpha subunit of IL2R that contacts an acidic amino acid residue in wild type IL2, the IL2 or the functional variant thereof is substituted at at least said acidic amino acid residue in wild type IL2, wherein if the amino acid residue is a basic amino acid residue in wild type IL2 the substitution is by an acidic amino acid residue and if the amino acid residue is an acidic amino acid residue in wild type IL2 the substitution is by a basic amino acid residue.

In one embodiment, the system of the invention comprises (i) a receptor polypeptide comprising a mutein of the alpha subunit of interleukin-2 receptor (IL2R) or of a functional variant of the alpha subunit of IL2R, wherein the alpha subunit of IL2R or the functional variant thereof is substituted at at least a position having an acidic amino acid residue in wild type alpha subunit of IL2R that contacts a basic amino acid residue in wild type IL2 and/or is substituted at at least a position having a basic amino acid residue in wild type alpha subunit of IL2R that contacts an acidic amino acid residue in wild type IL2, wherein if the amino acid residue is an acidic amino acid residue in wild type alpha subunit of IL2R the substitution is by a basic amino acid residue and if the amino acid residue is a basic amino acid residue in wild type alpha subunit of IL2R the substitution is by an acidic amino acid residue, (ii) a ligand polypeptide comprising a mutein of IL2 or of a functional variant of IL2, wherein when the alpha subunit of IL2R or the functional variant thereof is substituted at at least a position having an acidic amino acid residue in wild type alpha subunit of IL2R that contacts a basic amino acid residue in wild type IL2, the IL2 or the functional variant thereof is substituted at at least said basic amino acid residue in wild type IL2 and/or when the alpha subunit of IL2R or the functional variant thereof is substituted at at least a position having a basic amino acid residue in wild type alpha subunit of IL2R that contacts an acidic amino acid residue in wild type IL2, the IL2 or the functional variant thereof is substituted at at least said acidic amino acid residue in wild type IL2, wherein if the amino acid residue is a basic amino acid residue in wild type IL2 the substitution is by an acidic amino acid residue and if the amino acid residue is an acidic amino acid residue in wild type IL2 the substitution is by a basic amino acid residue.

In one embodiment of the system of the invention the alpha subunit of IL2R is the human alpha subunit of IL2R. In one embodiment of the system of the invention the IL2 is human IL2.

In different embodiments, the human alpha subunit of IL2R or the functional variant thereof and the human IL2 or the functional variant thereof are substituted at at least the following positions (relative to wild type human alpha subunit of IL2R and numbered in accordance with wild type human alpha subunit of IL2R, and relative to wild type human IL2 and numbered in accordance with wild type human IL2):

(i) IL2R or functional variant thereof: position 1 (glutamic acid), and
IL2 or functional variant thereof: position 35 (lysine);

(ii) IL2R or functional variant thereof: position 29 (glutamic acid), and
IL2 or functional variant thereof: position 43 (lysine);

(iii) IL2R or functional variant thereof: position 38 (lysine), and
IL2 or functional variant thereof: position 61 (glutamic acid);

(iv) IL2R or functional variant thereof: position 1 (glutamic acid),
IL2 or functional variant thereof: position 35 (lysine),
IL2R or functional variant thereof: position 29 (glutamic acid), and
IL2 or functional variant thereof: position 43 (lysine);

(v) IL2R or functional variant thereof: position 1 (glutamic acid),
IL2 or functional variant thereof: position 35 (lysine),
IL2R or functional variant thereof: position 38 (lysine), and
IL2 or functional variant thereof: position 61 (glutamic acid);

(vi) IL2R or functional variant thereof: position 29 (glutamic acid),
IL2 or functional variant thereof: position 43 (lysine),
IL2R or functional variant thereof: position 38 (lysine), and
IL2 or functional variant thereof: position 61 (glutamic acid); or (vii) IL2R or functional variant thereof: position 1 (glutamic acid),
IL2 or functional variant thereof: position 35 (lysine),
IL2R or functional variant thereof: position 29 (glutamic acid), IL2 or functional variant thereof: position 43 (lysine), IL2R or functional variant thereof: position 38 (lysine),
and IL2 or functional variant thereof: position 61 (glutamic acid).

IL2R or the functional variant thereof: In one embodiment, position 1 is substituted with lysine. In one embodiment, position 29 is substituted with lysine. In one embodiment, position 38 is substituted with glutamic acid.

IL2 or the functional variant thereof: In one embodiment, position 35 is substituted with glutamic acid. In one embodiment, position 43 is substituted with glutamic acid. In one embodiment, position 61 is substituted with lysine.

In one embodiment of the system of the invention (i) the alpha subunit of IL2R is the human alpha subunit of IL2R and the alpha subunit of IL2R or the functional variant thereof is substituted at at least position 1 (glutamic acid) relative to wild type human alpha subunit of IL2R and numbered in accordance with wild type human alpha subunit of IL2R, and (ii) the IL2 is human IL2 and the IL2 or the functional variant thereof is substituted at at least position 35 (lysine) relative to wild type human IL2 and numbered in accordance with wild type human IL2.

In one embodiment, position 1 is substituted with lysine. In one embodiment, position 35 is substituted with glutamic acid.

In one embodiment of the system of the invention (i) the alpha subunit of IL2R is the human alpha subunit of IL2R and the alpha subunit of IL2R or the functional variant thereof is substituted at at least position 29 (glutamic acid) relative to wild type human alpha subunit of IL2R and numbered in accordance with wild type human alpha subunit of IL2R, and (ii) the IL2 is human IL2 and the IL2 or the functional variant thereof is substituted at at least position 43 (lysine) relative to wild type human IL2 and numbered in accordance with wild type human IL2.

In one embodiment, position 29 is substituted with lysine. In one embodiment, position 43 is substituted with glutamic acid.

In one embodiment of the system of the invention (i) the alpha subunit of IL2R is the human alpha subunit of IL2R and the alpha subunit of IL2R or the functional variant thereof is substituted at at least position 38 (lysine) relative to wild type human alpha subunit of IL2R and numbered in accordance with wild type human alpha subunit of IL2R, and (ii) the IL2 is human IL2 and the IL2 or the functional variant thereof is substituted at at least position 61 (glutamic acid) relative to wild type human IL2 and numbered in accordance with wild type human IL2.

In one embodiment, position 38 is substituted with glutamic acid. In one embodiment, position 61 is substituted with lysine.

In one embodiment of the system of the invention (i) the alpha subunit of IL2R is the human alpha subunit of IL2R and the alpha subunit of IL2R or the functional variant thereof is substituted at at least position 1 (glutamic acid) by lysine, position 29 (glutamic acid) by lysine and position 38 (lysine) by glutamic acid relative to wild type human alpha subunit of IL2R and numbered in accordance with wild type human alpha subunit of IL2R, and (ii) the IL2 is human IL2 and the IL2 or the functional variant thereof is substituted at at least position 35 (lysine) by glutamic acid, position 43 (lysine) by glutamic acid and position 61 (glutamic acid) by lysine relative to wild type human IL2 and numbered in accordance with wild type human IL2.

In one embodiment of the system of the invention (i) the alpha subunit of IL2R is the human alpha subunit of IL2R and the alpha subunit of IL2R or the functional variant thereof is substituted at at least position 29 (glutamic acid) by lysine and position 38 (lysine) by glutamic acid relative to wild type human alpha subunit of IL2R and numbered in accordance with wild type human alpha subunit of IL2R, and (ii) the IL2 is human IL2 and the IL2 or the functional variant thereof is substituted at at least position 43 (lysine) by glutamic acid and position 61 (glutamic acid) by lysine relative to wild type human IL2 and numbered in accordance with wild type human IL2.

In one embodiment of the system of the invention (i) the alpha subunit of IL2R is the human alpha subunit of IL2R and the alpha subunit of IL2R or the functional variant thereof is substituted at at least position 38 (lysine) by glutamic acid relative to wild type human alpha subunit of IL2R and numbered in accordance with wild type human alpha subunit of IL2R, and (i) the IL2 is human IL2 and the IL2 or the functional variant thereof is substituted at at least position 61 (glutamic acid) by lysine relative to wild type human IL2 and numbered in accordance with wild type human 112.

In one embodiment of the system of the invention (i) the alpha subunit of IL2R is the human alpha subunit of IL2R and the alpha subunit of IL2R or the functional variant thereof is substituted at at least position 29 (glutamic acid) by lysine relative to wild type human alpha subunit of IL2R and numbered in accordance with wild type human alpha subunit of IL2R, and (ii) the IL2 is human IL2 and the IL2 or the functional variant thereof is substituted at at least position 43 (lysine) by glutamic acid relative to wild type human IL2 and numbered in accordance with wild type human IL2.

In one embodiment of the system of the invention (i) the alpha subunit of IL2R is the human alpha subunit of IL2R and the alpha subunit of IL2R or the functional variant thereof is substituted at at least position 29 (glutamic acid) by lysine and position 38 (lysine) by glutamic acid relative to wild type human alpha subunit of IL2R and numbered in accordance with wild type human alpha subunit of IL2R, and (ii) the IL2 is human IL2 and the IL2 or the functional variant thereof is substituted at at least position 35 (lysine) by glutamic acid, position 43 (lysine) by glutamic acid and position 61 (glutamic acid) by lysine relative to wild type human IL2 and numbered in accordance with wild type human IL2.

In one embodiment of the system of the invention (i) the alpha subunit of IL2R is the human alpha subunit of IL2R and the alpha subunit of IL2R or the functional variant thereof is substituted at at least position 29 (glutamic acid) by lysine relative to wild type human alpha subunit of IL2R and numbered in accordance with wild type human alpha subunit of IL2R, and (ii) the IL2 is human IL2 and the IL2 or the functional variant thereof is substituted at at least position 35 (lysine) by glutamic acid, position 43 (lysine) by glutamic acid and position 61 (glutamic acid) by lysine relative to wild type human IL2 and numbered in accordance with wild type human IL2.

In one embodiment of the system of the invention (i) the alpha subunit of IL2R is the human alpha subunit of IL2R and the alpha subunit of IL2R or the functional variant thereof is substituted at at least position 29 (glutamic acid) by lysine relative to wild type human alpha subunit of IL2R and numbered in accordance with wild type human alpha subunit of IL2R, and (ii) the IL2 is human IL2 and the IL2 or the functional variant thereof is substituted at at least position 43 (lysine) by glutamic acid and position 61 (glutamic acid) by lysine relative to wild type human IL2 and numbered in accordance with wild type human IL2.

In one embodiment of the system of the invention (i) the alpha subunit of IL2R is the human alpha subunit of IL2R and the alpha subunit of IL2R or the functional variant thereof is substituted at at least position 1 (glutamic acid) by lysine, position 29 (glutamic acid) by lysine and position 38 (lysine) by glutamic acid relative to wild type human alpha subunit of IL2R and numbered in accordance with wild type human alpha subunit of IL2R, and (ii) the IL2 is human IL2 and the IL2 or the functional variant thereof is substituted at at least position 43 (lysine) by glutamic acid and position 61 (glutamic acid) by lysine relative to wild type human IL2 and numbered in accordance with wild type human IL2.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 1 (glutamic acid) by a basic amino acid residue relative to wild type human alpha subunit of IL2R and numbered in accordance with wild type human alpha subunit of IL2R, and (ii) a ligand polypeptide comprising a mutein of human IL2 or of a functional variant of human IL2, wherein the IL2 or the functional variant thereof is substituted at at least position 35 (lysine) by an acidic amino acid residue relative to wild type human IL2 and numbered in accordance with wild type human IL2.

In one embodiment, position 1 is substituted with lysine. In one embodiment, position 35 is substituted with glutamic acid.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 29 (glutamic acid) by a basic amino acid residue relative to wild type human alpha subunit of IL2R and numbered in accordance with wild type human alpha subunit of IL2R, and (ii) a ligand polypeptide comprising a mutein of human IL2 or of a functional variant of human IL2, wherein the IL2 or the functional variant thereof is substituted at at least position 43 (lysine) by an acidic amino acid residue relative to wild type human IL2 and numbered in accordance with wild type human IL2.

In one embodiment, position 29 is substituted with lysine. In one embodiment, position 43 is substituted with glutamic acid.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 38 (lysine) by an acidic amino acid residue relative to wild type human alpha subunit of IL2R and numbered in accordance with wild type human alpha subunit of IL2R, and (ii) a ligand polypeptide comprising a mutein of human IL2 or of a functional variant of human IL2, wherein the IL2 or the functional variant thereof is substituted at at least position 61 (glutamic acid) by a basic amino acid residue relative to wild type human IL2 and numbered in accordance with wild type human IL2.

In one embodiment, position 38 is substituted with glutamic acid. In one embodiment, position 61 is substituted with lysine.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 1 (glutamic acid) by lysine, position 29 (glutamic acid) by lysine and position 38 (lysine) by glutamic acid relative to wild type human alpha subunit of IL2R and numbered in accordance with wild type human alpha subunit of IL2R, and (ii) a ligand polypeptide comprising a mutein of human IL2 or of a functional variant of human IL2, wherein the IL2 or the functional variant thereof is substituted at at least position 35 (lysine) by glutamic acid, position 43 (lysine) by glutamic acid and position 61 (glutamic acid) by lysine relative to wild type human IL2 and numbered in accordance with wild type human IL2.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 29 (glutamic acid) by lysine and position 38 (lysine) by glutamic acid relative to wild type human alpha subunit of IL2R and numbered in accordance with wild type human alpha subunit of IL2R, and (ii) a ligand polypeptide comprising a mutein of human IL2 or of a functional variant of human IL2, wherein the IL2 or the functional variant thereof is substituted at at least position 43 (lysine) by glutamic acid and position 61 (glutamic acid) by lysine relative to wild type human IL2 and numbered in accordance with wild type human IL2.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 38 (lysine) by glutamic acid relative to wild type human alpha subunit of IL2R and numbered in accordance with wild type human alpha subunit of IL2R, and (ii) a ligand polypeptide comprising a mutein of human IL2 or of afunctional variant of human IL2, wherein the IL2 or the functional variant thereof is substituted at at least position 61 (glutamic acid) by lysine relative to wild type human IL2 and numbered in accordance with wild type human IL2.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 29 (glutamic acid) by lysine relative to wild type human alpha subunit of IL2R and numbered in accordance with wild type human alpha subunit of IL2R, and (i) a ligand polypeptide comprising a mutein of human IL2 or of afunctional variant of human IL2, wherein the IL2 or the functional variant thereof is substituted at at least position 43 (lysine) by glutamic acid relative to wild type human IL2 and numbered in accordance with wild type human IL2.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 29 (glutamic acid) by lysine and position 38 (lysine) by glutamic acid relative to wild type human alpha subunit of IL2R and numbered in accordance with wild type human alpha subunit of IL2R, and (ii) a ligand polypeptide comprising a mutein of human IL2 or of afunctional variant of human IL2, wherein the IL2 or the functional variant thereof is substituted at at least position 35 (lysine) by glutamic acid, position 43 (lysine) by glutamic acid and position 61 (glutamic acid) by lysine relative to wild type human IL2 and numbered in accordance with wild type human IL2.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 29 (glutamic acid) by lysine relative to wild type human alpha subunit of IL2R and numbered in accordance with wild type human alpha subunit of IL2R, and (ii) a ligand polypeptide comprising a mutein of human IL2 or of a functional variant of human IL2, wherein the IL2 or the functional variant thereof is substituted at at least position 35 (lysine) by glutamic acid, position 43 (lysine) by glutamic acid and position 61 (glutamic acid) by lysine relative to wild type human IL2 and numbered in accordance with wild type human IL2.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 29 (glutamic acid) by lysine relative to wild type human alpha subunit of IL2R and numbered in accordance with wild type human alpha subunit of IL2R, and (ii) a ligand polypeptide comprising a mutein of human IL2 or of afunctional variant of human IL2, wherein the IL2 or the functional variant thereof is substituted at at least position 43 (lysine) by glutamic acid and position 61 (glutamic acid) by lysine relative to wild type human IL2 and numbered in accordance with wild type human IL2.

A further aspect of the invention relates to a system comprising:

(i) a receptor polypeptide comprising a mutein of the human alpha subunit of interleukin-2 receptor (IL2R) or of a functional variant of the human alpha subunit of IL2R, wherein the alpha subunit of IL2R or the functional variant thereof is substituted at at least position 1 (glutamic acid) by lysine, position 29 (glutamic acid) by lysine and position 38 (lysine) by glutamic acid relative to wild type human alpha subunit of IL2R and numbered in accordance with wild type human alpha subunit of IL2R, and (ii) a ligand polypeptide comprising a mutein of human IL2 or of afunctional variant of human IL2, wherein the IL2 or the functional variant thereof is substituted at at least position 43 (lysine) by glutamic acid and position 61 (glutamic acid) by lysine relative to wild type human IL2 and numbered in accordance with wild type human IL2.

In different embodiments, the alpha subunit of IL2R or functional variant thereof and/or the IL2 or functional variant thereof is each substituted at one or more, such as two or more or three or more, such as 2, 3, 4, 5, 6, 7 or 8 positions, in particular positions having an acidic or basic amino acid residue in wild type alpha subunit of IL2R and/or wild type IL2, wherein the respective positions in wild type alpha subunit of IL2R and/or wild type IL2 are positions forming pairs of acidic/basic amino acids contacting each other. In one embodiment, an acidic amino acid residue in wild type IL2 contacts a basic amino acid residue in the alpha subunit of IL2R. In one embodiment, a basic amino acid residue in wild type IL2 contacts an acidic amino acid residue in the alpha subunit of IL2R.

In one embodiment of the system of any aspect of the invention the alpha subunit of IL2R has the amino acid sequence according to SEQ ID NO: 2.

In one embodiment of the system of any aspect of the invention the IL2 has the amino acid sequence according to SEQ ID NO: 1.

In one embodiment, the mutein under (ii) binds to and activates IL2R comprising the mutein under (i) as alpha subunit. In one embodiment, binding to and/or activation of IL2R comprising the mutein under (i) as alpha subunit by the mutein under (ii) exceeds binding to and/or activation of IL2R comprising the alpha subunit of IL2R or the functional variant thereof as alpha subunit by the mutein under (i). In one embodiment, binding to and/or activation of IL2R comprising the mutein under (i) as alpha subunit by the mutein under (ii) exceeds binding to and/or activation of IL2R comprising the mutein under (i) as alpha subunit by IL2 or the functional variant thereof. In one embodiment, binding to and/or activation of IL2R comprising the alpha subunit of IL2R or the functional variant thereof as alpha subunit by IL2 or the functional variant thereof exceeds binding to and/or activation of IL2R comprising the alpha subunit of IL2R or the functional variant thereof as alpha subunit by the mutein under (ii). In one embodiment, binding to and/or activation of IL2R comprising the alpha subunit of IL2R or the functional variant thereof as alpha subunit by IL2 or the functional variant thereof exceeds binding to and/or activation of IL2R comprising the mutein under (i) as alpha subunit by IL2 or the functional variant thereof.

In one embodiment of the system of any aspect of the invention the substitution in IL2 or the functional variant thereof reduces the affinity for IL2R comprising the wild type alpha subunit of IL2R as alpha subunit (IL2Rαβγ).

In one embodiment of the system of any aspect of the invention the substitution in IL2 or the functional variant thereof reduces the affinity for IL2R comprising the wild type alpha subunit of IL2R as alpha subunit (IL2Rαβγ) to a greater extent than for the βγ IL2 receptor complex (IL2Rβγ).

In one embodiment of the system of any aspect of the invention the mutein under (ii) has a decreased ability to stimulate regulatory T cells compared to wild type IL2.

In one embodiment, the substituted IL2 or functional variant thereof (IL2 mutein) described above has an amino acid sequence identical to wild type IL2 at the other, non-substituted residues. In one embodiment, the IL2 mutein described above has amino acid modifications such as amino acid substitutions at one or more sites in or at the other residues of wild type IL2. In one embodiment, such amino acid substitutions result in relatively increased affinity for IL2Rβγ when compared to wild type IL2 (also termed "mutβγ" mutations herein). Such mutants are potent IL2 signaling agonists. In one embodiment, such amino acid substitutions are at amino acid residues that contact IL2Rβ and/or IL2Rγ.

In one embodiment, the one or more amino acid substitutions which enhance the affinity for IL2Rβγ comprise substitutions at one or more positions of IL2 selected from the group consisting of K9, L12, Q13, E15, H16, D20, Q74, L80, R81, D84, L85, I86, N88, I92, L94, and E95.

In one embodiment, the one or more amino acid substitutions which enhance the affinity for IL2Rβγ comprise a substitution at at least one of positions 24, 65, 74, 80, 81, 85, 86, 89, 92, and 93 relative to wild type human IL2 and numbered in accordance with wild type human IL2. The substituted amino acid residue(s) can be, but are not necessarily, conservative substitutions. For example, the mutation can be: I24V, P65H, Q74R, Q74H, Q74N, Q74S, L80F, L80V, R81I, R81T, R81D, L85V, I86V, I89V, I92F, V93I.

In one embodiment, the IL2 mutein comprises the following set of amino acid substitutions: 80F/81D/85V/86V/ 92F. The IL2 mutein may further comprise the amino acid substitution 42A. The IL2 mutein may further comprise one or more of the following amino acid substitutions: 24V, 65H, 74R, 74H, 74N, 74S, 89V, 93I.

In some embodiments, the IL2 mutein comprises a set of amino acid substitutions selected from the group consisting of:

(i) 74N, 80F, 81D, 85V, 86V, 89V, 92F;

(ii) 74H, 80F, 81D, 85V, 86V, 92F;

(iii) 74S, 80F, 81D, 85V, 86V, 92F;

(iv) 74N, 80F, 81D, 85V, 86V, 92F;

(v) 80F, 81D, 85V, 86V, 92F;

(vi) 80F, 81D, 85V, 86V, 89V, 92F, 93I;

(vii) 18R, 22E, 80F, 81D, 85V, 86V, 89V, 92F, 93I, 126T;

(viii) 18R, 22E, 74S, 80F, 81T, 85V, 86V, 89V, 92F, 93I, 126T.

In one embodiment of the system of any aspect of the invention the mutein under (ii) further comprises one or more amino acid substitutions which enhance the affinity for IL2Rβγ. In one embodiment, the one or more amino acid substitutions which enhance the affinity for IL2Rβγ comprise the following set of substitutions: 80F, 81D, 85V, 86V, 92F.

The IL2 mutein described herein may be attached to a pharmacokinetic modifying group and, thus, may be an "extended-pharmacokinetic (PK) IL2". In one aspect, the ligand polypeptide described herein is an extended pharmacokinetic (PK) IL2 further comprising an amino acid sequence which is heterologous to the IL2 or functional variant thereof fused to the IL2 mutein. In one embodiment, the amino acid sequence which is heterologous to the IL2 or functional variant thereof is selected from the group consisting of serum albumin, an immunoglobulin fragment, transferrin, and Fn3, or variants thereof. In one embodiment, the serum albumin comprises mouse serum albumin or human serum albumin. In one embodiment, the immunoglobulin fragment comprises an immunoglobulin Fc domain.

In one embodiment of the system of any aspect of the invention the ligand polypeptide is an extended pharmacokinetic (PK) polypeptide. In one embodiment, the extended-PK polypeptide comprises a fusion protein. In one embodiment, the fusion protein comprises a moiety of the mutein under (i) and a moiety which is heterologous to IL2 or the functional variant thereof. In one embodiment, the fusion protein comprises a moiety of the mutein under (ii) and a moiety selected from the group consisting of serum albumin, an immunoglobulin fragment, transferrin, Fn3, and variants thereof. In one embodiment, the serum albumin comprises mouse serum albumin or human serum albumin. In one embodiment, the immunoglobulin fragment comprises an immunoglobulin Fc domain.

The above described receptor polypeptides are also termed "IL2Rα variant polypeptide", "IL2R variant polypeptide" or simply "IL2R variant" herein. The above described ligand polypeptides are also termed "IL2 variant polypeptide" or simply "IL2 variant" herein.

In different embodiments, a system described herein comprises combinations of receptor polypeptides and ligand polypeptides comprising IL2R receptor polypeptides and IL2 ligand polypeptides, respectively, selected from the following:

| IL2R receptor polypeptide | IL2 ligand polypeptide |
| --- | --- |
| SEQ ID NO: 17 (optionally without N-terminal 21 aa signal peptide) | SEQ ID NO: 5 or SEQ ID NO: 10 |
| SEQ ID NO: 14 (optionally without N-terminal 21 aa signal peptide) | SEQ ID NO: 6 or SEQ ID NO: 11 |
| SEQ ID NO: 15 (optionally without N-terminal 21 aa signal peptide) | SEQ ID NO: 7 or SEQ ID NO: 12 |
| SEQ ID NO: 16 (optionally without N-terminal 21 aa signal peptide) | SEQ ID NO: 8 or SEQ ID NO: 13 |
| SEQ ID NO: 14 (optionally without N-terminal 21 aa signal peptide) | SEQ ID NO: 5 or SEQ ID NO: 10 |
| SEQ ID NO: 16 (optionally without N-terminal 21 aa signal peptide) | SEQ ID NO: 6 or SEQ ID NO: 11 |
| SEQ ID NO: 16 (optionally without N-terminal 21 aa signal peptide) | SEQ ID NO: 5 or SEQ ID NO: 10 |
| SEQ ID NO: 17 (optionally without N-terminal 21 aa signal peptide) | SEQ ID NO: 6 or SEQ ID NO: 11 |

A further aspect of the invention relates to a receptor polypeptide of any of the systems described herein.

A further aspect of the invention relates to a polynucleotide encoding the receptor polypeptide described herein. In one embodiment, the polynucleotide is RNA.

A further aspect of the invention relates to a host cell comprising the polynucleotide described herein. A further aspect of the invention relates to a host cell genetically modified to express a receptor polypeptide of any of the systems described herein. In one embodiment, the host cell is an immune effector cell. In one embodiment, the immune effector cell is a T cell.

A further aspect of the invention relates to a pharmaceutical composition comprising the polynucleotide described herein or the host cell described herein. In one embodiment, the pharmaceutical composition further comprises one or more pharmaceutically acceptable carriers, diluents and/or excipients.

A further aspect of the invention relates to a method of treating a subject comprising administering to the subject the polynucleotide described herein, the host cell described herein, or the pharmaceutical composition described herein. In one embodiment, the method is a method for treating or preventing cancer in a subject.

A further aspect of the invention relates to a medical preparation comprising:

(i) a polynucleotide encoding a receptor polypeptide of the system described herein or an immune effector cell genetically modified to express a receptor polypeptide of the system described herein, and (ii) the corresponding ligand polypeptide of the system under (i), a polynucleotide encoding the ligand polypeptide, or a host cell genetically modified to express the ligand polypeptide.

In one embodiment, the medical preparation is a kit. In one embodiment, the medical preparation comprises each component (i) and (ii) in separate containers. In one embodiment, the components are present in a pharmaceutical composition. In one embodiment, the pharmaceutical composition further comprises one or more pharmaceutically acceptable carriers, diluents and/or excipients. In one embodiment, the medical preparation further comprises instructions for use of the medical preparation for treating or preventing cancer.

A further aspect of the invention relates to the medical preparation described herein for pharmaceutical use. In one embodiment, the pharmaceutical use comprises a therapeutic or prophylactic treatment of a disease or disorder.

A further aspect of the invention relates to the medical preparation described herein for use in a method for treating or preventing cancer in a subject.

A further aspect of the invention relates to a method for treating a subject comprising:

(i) providing to the subject immune effector cells genetically modified to express a receptor polypeptide of the system described herein, and (ii) administering to the subject the corresponding ligand polypeptide of the system under (i), a polynucleotide encoding the ligand polypeptide, or a host cell genetically modified to express the ligand polypeptide.

In one embodiment, the subject has cancer.

In one embodiment, the method is a method of inducing an immune response in said subject. In one embodiment, the immune response is a T cell-mediated immune response.

A further aspect of the invention relates to a method for treating a subject having a disease, disorder or condition associated with expression or elevated expression of an antigen comprising:

(i) providing to the subject immune effector cells genetically modified to express a receptor polypeptide of the system described herein, the immune effector cells being targeted to the antigen or cells expressing the antigen and (ii) administering to the subject the corresponding ligand polypeptide of the system under (i), a polynucleotide encoding the ligand polypeptide, or a host cell genetically modified to express the ligand polypeptide.

In one embodiment, the disease, disorder or condition is cancer and the antigen is a tumor-associated antigen.

In one embodiment, the immune effector cells genetically modified to express a receptor polypeptide are provided to the subject by administering the immune effector cells genetically modified to express a receptor polypeptide or by generating the immune effector cells genetically modified to express a receptor polypeptide in the subject.

In one embodiment, the method described herein is a method for treating or preventing cancer in a subject. In one embodiment, the cancer is selected from the group consisting of melanoma, leukemia, lymphoma, lung cancer, breast cancer, prostate cancer, ovarian cancer, colon cancer, mesothelioma, renal cell carcinoma, and brain cancer.

In one embodiment of a medical preparation or method described herein, the polynucleotide encoding the receptor polypeptide and/or the polynucleotide encoding the ligand polypeptide is RNA.

In one embodiment of the medical preparation, the RNA is present in a form selected from a liquid form, a solid form, or a combination thereof. In one embodiment, the solid form is a frozen form or a dehydrated form. In one embodiment, the dehydrated form is a freeze-dried or spray-dried form.

In one embodiment of a medical preparation or method described herein, the immune effector cells genetically modified to express a receptor polypeptide comprise a polynucleotide encoding the receptor polypeptide.

In one embodiment of a medical preparation or method described herein, the host cell genetically modified to express the ligand polypeptide comprises a polynucleotide encoding the ligand polypeptide.

In one embodiment of a medical preparation or method described herein, the polynucleotide encoding the receptor polypeptide and/or the polynucleotide encoding the ligand polypeptide is RNA.

In one embodiment of a medical preparation or method described herein, the immune effector cells are T cells.

In one embodiment, the methods described herein further comprise administering to the subject an immune checkpoint inhibitor. In one embodiment, the immune checkpoint inhibitor targets the interaction between (i) PD-1 and PD-L1, or (ii) CTLA-4 and CD80 or CD86. In one embodiment, the immune checkpoint inhibitor is an antibody or antibody fragment. In one embodiment, the antibody or antibody fragment targets PD-1, PD-L1, or CTLA-4.

Similarly, in one embodiment, the medical preparation described herein further comprises an immune checkpoint inhibitor. In one embodiment, the immune checkpoint inhibitor targets the interaction between (i) PD-1 and PD-1, or (ii) CTLA-4 and CD80 or CD86. In one embodiment, the immune checkpoint inhibitor is an antibody or antibody fragment. In one embodiment, the antibody or antibody fragment targets PD-1, PD-L1, or CTLA-4.

In a further aspect, the invention relates to the agents and compositions described herein, e.g., IL2R variants, IL2 variants or IL2R/IL2 variant systems described herein, polynucleotides coding for IL2R variants, IL2 variants or IL2R/IL2 variant systems described herein, cells expressing IL2R variants described herein, for therapeutic use, in particular for use in the methods described herein.

Other features and advantages of the instant invention will be apparent from the following detailed description and claims.

Figure 7:
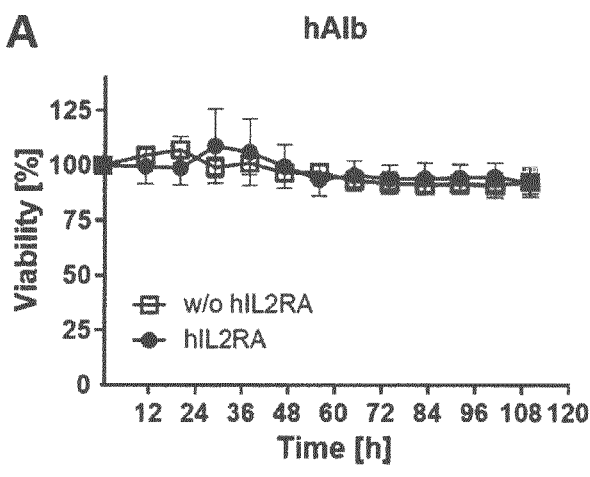
FIG. 7, 8, 9: Effect of hAlb-hIL2 variants on in vitro anti-tumor efficacy of CAR redirected CD8⁺ T cells electroporated with different hIL2RA (CD25) mutants.
Figure 7:
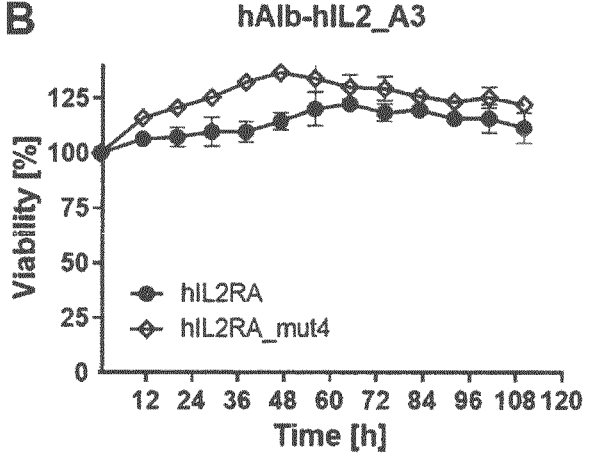
Figure 7:
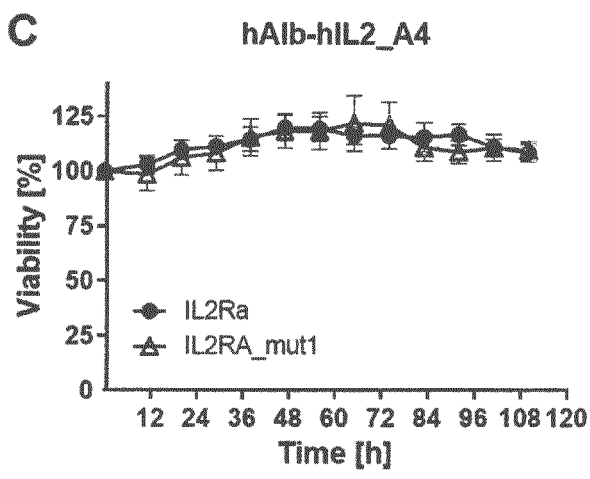

Claudin-6 (CLDN6) positive, eGFP-transgenic PA-1 tumor spheroids were cultivated together with CD8⁺ T cells electroporated with IVT-mRNA coding for hIL2RA mutants (hIL2RA_mut1, hIL2RA_mut4 or hIL2RA wild-type) and CLDN6-specific CAR constructs. A Claudin-18.2 (CLDN18.2)-specific CAR construct was used as a negative control (mock CAR). Co-cultures were initiated with a sub-optimal effector-to-target ratio of 10:1 and treated with 25% supernatants containing the corresponding reciprocal hAlb-hIL2 variants hAlb-hIL2_A3, hAlb-hIL2_A4 or hAlb as control with n=3 replicates per condition. CAR T cell mediated cytotoxicity was assessed over time using the fluorescence signal of tumor spheroids as a surrogate marker for cell viability in an Incucyte S3 live cell imaging system. The total green object area of each tumor spheroid triplicate was recorded and normalized to the respective spheroid area at the beginning of the co-culture. Data for each CAR construct (CLDN18.2 CAR 28K, CLDN6 CAR 28ζ and CLDN6 CAR BBζ) are plotted separately in FIG. 7, FIG. 8 and FIG. 9, respectively.

DETAILED DESCRIPTION

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term 'about' means approximately or nearly, and in the context of a numerical value or range set forth herein in one embodiment means ±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and al examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e., for the purpose of this embodiment "comprising" is to be understood as having the meaning of "consisting of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

In the following, definitions will be provided which apply to all aspects of the present disclosure. The following terms have the following meanings unless otherwise indicated. Any undefined terms have their art recognized meanings.

Definitions

Terms such as "reduce", "decrease", "inhibit" or "impair" as used herein relate to an overall decrease or the ability to cause an overall decrease, preferably of 5% or greater, 10% or greater, 20% or greater, more preferably of 50% or greater, and most preferably of 75% or greater, in the level, e.g. in the level of binding.

Terms such as "increase", "enhance" or 'exceed' preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, or even more.

According to the disclosure, the term "peptide" comprises oligopeptides and refers to substances which comprise about two or more, about 3 or more, about 4 or more, about 6 or more, about 8 or more, about or more, about 13 or more, about 16 or more, about 20 or more, and up to about 50, about 100 or about 150, consecutive amino acids linked to one another via peptide bonds. The term "protein" or "polypeptide" refers to large peptides, in particular peptides having at least about 150 amino acids, but the terms "peptide", "protein" and "polypeptide" are used herein usually as synonyms.

A "therapeutic protein" has a positive or advantageous effect on a condition or disease state of a subject when provided to the subject in a therapeutically effective amount. In one embodiment, a therapeutic protein has curative or palliative properties and may be administered to ameliorate, relieve, alleviate, reverse, delay onset of or lessen the severity of one or more symptoms of a disease or disorder. A therapeutic protein may have prophylactic properties and may be used to delay the onset of a disease or to lessen the severity of such disease or pathological condition. The term "therapeutic protein" includes entire proteins or peptides, and can also refer to therapeutically active fragments thereof. It can also include therapeutically active variants of a protein. Examples of therapeutically active proteins include, but are not limited to, cytokines, and antigens for vaccination.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

By "variant" or "variant protein" or "variant polypeptide" herein is meant a protein that differs from a wild type protein by virtue of at least one amino acid modification. The parent polypeptide may be a naturally occurring or wild type (WT) polypeptide, or may be a modified version of a wild type polypeptide. Preferably, the variant polypeptide has at least one amino acid modification compared to the parent polypeptide, e.g. from 1 to about 20 amino acid modifications, and preferably from 1 to about 10 or from 1 to about 5 amino acid modifications compared to the parent.

By "parent polypeptide", "parent protein", "precursor polypeptide", or "precursor protein" as used herein is meant an unmodified polypeptide that is subsequently modified to generate a variant. A parent polypeptide may be a wild type polypeptide, or a variant or engineered version of a wild type polypeptide.

By "wild type" or "WT" or "native" herein is meant an amino acid sequence that is found in nature, including allelic variations. A wild type protein or polypeptide has an amino acid sequence that has not been intentionally modified.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all splice variants, posttranslationally modified variants, conformations, isoforms and species homologs, in particular those which are naturally expressed by cells. The term "variant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:

glycine, alanine;

valine, isoleucine, leucine;

aspartic acid, glutamic acid;

asparagine, glutamine;

serine, threonine;

lysine, arginine; and phenylalanine, tyrosine.

The term "acidic amino acid residue" preferably relates to glutamic acid (glutamate, Glu) or aspartic acid (aspartate, Asp), in particular glutamic acid. The term "basic amino acid residue" preferably relates to lysine (Lys) or arginine (Arg), in particular lysine.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the disclosure at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one embodiment, a fragment or variant of an amino acid sequence (peptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent. With respect to cytokines such as IL2, one particular function is one or more immunomodulatory activities displayed by the amino acid sequence from which the fragment or variant is derived and/or binding to the receptor(s) the amino acid sequence from which the fragment or variant is derived binds to. With respect to cytokine receptors such as IL2R, one particular function is one or more immunomodulatory activities displayed by the amino acid sequence from which the fragment or variant is derived and/or binding to the ligand(s) the amino acid sequence from which the fragment or variant is derived binds to. The term "functional fragment" or "functional variant", as used herein, in particular refers to a variant molecule or sequence that comprises an amino acid sequence that is altered by one or more amino acids compared to the amino acid sequence of the parent molecule or sequence and that is still capable of fulfilling one or more of the functions of the parent molecule or sequence, e.g., binding to a target molecule or contributing to binding to a target molecule. In one embodiment, the modifications in the amino acid sequence of the parent molecule or sequence do not significantly affect or alter the binding characteristics of the molecule or sequence. In different embodiments, binding of the functional fragment or functional variant may be reduced but still significantly present, e.g., binding of the functional variant may be at least 50%, at least 60%, at least 70%, at least 80%, or at least 90% of the parent molecule or sequence. However, in other embodiments, binding of the functional fragment or functional variant may be enhanced compared to the parent molecule or sequence.

An amino acid sequence (peptide, protein or polypeptide) "derived from" a designated amino acid sequence (peptide, protein or polypeptide) refers to the origin of the first amino acid sequence. Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof. For example, it will be understood by one of ordinary skill in the art that the antigens and cytokines (e.g., IL2) suitable for use herein may be altered such that they vary in sequence from the naturally occurring or native sequences from which they were derived, while retaining the desirable activity of the native sequences.

As used herein, an "instructional material" or "instructions" includes a publication, a recording, a diagram, or any other medium of expression which can be used to communicate the usefulness of the compositions and methods of the invention. The instructional material of the kit of the invention may, for example, be affixed to a container which contains the compositions of the invention or be shipped together with a container which contains the compositions. Alternatively, the instructional material may be shipped separately from the container with the intention that the instructional material and the compositions be used cooperatively by the recipient.

"Isolated" means altered or removed from the natural state. For example, a nucleic acid or a peptide naturally present in a living animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a host cell.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "specifically binds", as used herein, is meant a molecule such as an antibody or CAR which recognizes a specific antigen, but does not substantially recognize or bind other molecules in a sample or in a subject. For example, an antibody that specifically binds to an antigen from one species may also bind to that antigen from one or more other species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding", or "specifically binding", can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "genetic modification" includes the transfection of cells with nucleic acid. The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. RNA can be transfected into cells to transiently express its coded protein. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. Such stable transfection can be achieved by using virus-based systems or transposon-based systems for transfection. Generally, cells that are genetically modified to express a receptor polypeptide and/or an antigen receptor are stably transfected with nucleic acid encoding the receptor polypeptide and/or nucleic acid encoding the antigen receptor, while, generally, nucleic acid encoding a ligand polypeptide and/or nucleic acid encoding antigen is transiently transfected into cells.

Immune Effector Cells

The cells used in connection with the present invention and into which nucleic acids (DNA or RNA) encoding IL2 receptor polypeptides, in particular IL2Rα, (optionally together with nucleic acids encoding IL2Rβ and/or IL2Rγ), and optionally nucleic acids (DNA or RNA) encoding antigen receptors may be introduced include any cell which, either naturally or following transfection with one or more IL2R polypeptides, is responsive to IL2. Such responsiveness includes activation, differentiation, proliferation, survival and/or indication of one or more immune effector functions. The cells include, in particular, immune effector cells such as cells with lytic potential, in particular lymphoid cells, and are preferably T cells, in particular cytotoxic lymphocytes, preferably selected from cytotoxic T cells, natural killer (NK) cells, and lymphokine-activated killer (LAK) cells. Upon activation, each of these cytotoxic lymphocytes triggers the destruction of target cells. For example, cytotoxic T cells trigger the destruction of target cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target cells. The cells used in connection with the present invention will preferably be autologous cells, although heterologous cells or allogenic cells can be used.

The term "effector functions" in the context of the present invention includes any functions mediated by components of the immune system that result, for example, in the killing of diseased cells such as tumor cells, or in the inhibition of tumor growth and/or inhibition of tumor development, including inhibition of tumor dissemination and metastasis. Preferably, the effector functions in the context of the present invention are T cell mediated effector functions. Such functions comprise in the case of a helper T cell (CD4$^+$ T cell) the release of cytokines and/or the activation of CD8$^+$ lymphocytes (CTLs) and/or B cells, and in the case of CTL the elimination of cells, i.e., cells characterized by expression of an antigen, for example, via apoptosis or perforin-mediated cell lysis, production of cytokines such as IFN-γ and TNF-α, and specific cytolytic killing of antigen expressing target cells.

The term "immune effector cell" or "immunoreactive cell" in the context of the present invention relates to a cell which exerts effector functions during an immune reaction. An "immune effector cell" in one embodiment is capable of binding an antigen such as an antigen presented in the context of MHC on a cell or expressed on the surface of a cell and mediating an immune response. For example, immune effector cells comprise T cells (cytotoxic T cells, helper T cells, tumor infiltrating T cells), B cells, natural killer cells, neutrophils, macrophages, and dendritic cells. Preferably, in the context of the present invention, "immune effector cells" are T cells, preferably CD4$^+$ and/or CD8$^+$ T cells. According to the invention, the term "immune effector cell" also includes a cell which can mature into an immune cell (such as T cell, in particular T helper cell, or cytolytic T cell) with suitable stimulation. Immune effector cells comprise CD34$^+$ hematopoietic stem cells, immature and mature T cells and immature and mature B cells. The differentiation of T cell precursors into a cytolytic T cell, when exposed to an antigen, is similar to clonal selection of the immune system.

Preferably, an "immune effector cell" recognizes an antigen with some degree of specificity, in particular if presented in the context of MHC or present on the surface of diseased cells such as cancer cells. Preferably, said recognition enables the cell that recognizes an antigen to be responsive or reactive. If the cell is a helper T cell (CD4$^+$ T cell) such responsiveness or reactivity may involve the release of cytokines and/or the activation of CD8$^+$ lymphocytes (CTLs) and/or B cells. If the cell is a CTL such responsiveness or reactivity may involve the elimination of cells, i.e., cells characterized by expression of an antigen, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen and are responsive or reactive are also termed "antigen-responsive CTL" herein.

In one embodiment, the immune effector cells are CAR-expressing immune effector cells. In one embodiment, the immune effector cells are TCR-expressing immune effector cells.

The immune effector cells to be used according to the invention may express an endogenous antigen receptor such as T cell receptor or B cell receptor or may lack expression of an endogenous antigen receptor.

A "lymphoid cell" is a cell which, optionally after suitable modification, e.g. after transfer of an antigen receptor such as a TCR or a CAR, is capable of producing an immune response such as a cellular immune response, or a precursor cell of such cell, and includes lymphocytes, preferably T lymphocytes, lymphoblasts, and plasma cells. A lymphoid cell may be an immune effector cell as described herein. A preferred lymphoid cell is a T cell which can be modified to express an antigen receptor on the cell surface. In one embodiment, the lymphoid cell lacks endogenous expression of a T cell receptor.

The terms "T cell" and "T lymphocyte" are used interchangeably herein and include T helper cells (CD4$^+$ T cells) and cytotoxic T cells (CTLs, CD8$^+$ T cells) which comprise cytolytic T cells. The term "antigen-specific T cell" or similar terms relate to a T cell which recognizes the antigen to which the T cell is targeted and preferably exerts effector functions of T cells. T cells are considered to be specific for antigen if the cells kill target cells expressing an antigen. T cell specificity may be evaluated using any of a variety of standard techniques, for example, within a chromium release assay or proliferation assay. Alternatively, synthesis of lymphokines (such as IFN-γ) can be measured.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4$^+$ T cells because they express the CD4 glycoprotein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8$^+$ T cells since they express the CD8 glycoprotein on their surface. These cells recognize their targets by binding to antigen associated with MHC class I, which is present on the surface of nearly every cell of the body.

"Regulatory T cells" or "Tregs" are a subpopulation of T cells that modulate the immune system, maintain tolerance to self-antigens, and prevent autoimmune disease. Tregs are immunosuppressive and generally suppress or downregulate induction and proliferation of effector T cells. Tregs express the biomarkers CD4, FoxP3, and CD25.

As used herein, the term "naïve T cell" refers to mature T cells that, unlike activated or memory T cells, have not encountered their cognate antigen within the periphery. Naïve T cells are commonly characterized by the surface expression of L-selectin (CD62L), the absence of the activation markers CD25, CD44 or CD69 and the absence of the memory CD45RO isoform.

As used herein, the term "memory T cells" refers to a subgroup or subpopulation of T cells that have previously encountered and responded to their cognate antigen. At a second encounter with the antigen, memory T cells can reproduce to mount a faster and stronger immune response than the first time the immune system responded to the antigen. Memory T cells may be either CD4$^+$ or CD8$^+$ and usually express CD45RO.

All T cells have a T cell receptor (TCR) existing as a complex of several proteins. In the majority of T cells, the actual T cell receptor is composed of two separate peptide chains, which are produced from the independent T cell receptor alpha and beta (TCRα and TCRβ) genes and are called α- and β-TCR chains. A much less common (2% of total T cells) group of T cells, the γδ T cells (gamma delta T cells) possess a distinct T cell receptor (TCR) on their surface, which is made up of one γ-chain and one δ-chain.

All T cells originate from hematopoietic stem cells in the bone marrow. Hematopoietic progenitors derived from hematopoietic stem cells populate the thymus and expand by cell division to generate a large population of Immature thymocytes. The earliest thymocytes express neither CD4 nor CD8, and are therefore classed as double-negative (CD4$^-$CD8$^-$) cells. As they progress through their development they become double-positive thymocytes (CD4$^+$ CD8$^+$), and finally mature to single-positive (CD4$^+$CD8$^-$ or CD4$^-$ CD8$^+$) thymocytes that are then released from the thymus to peripheral tissues.

T cells may generally be prepared in vitro or ex vivo, using standard procedures. For example, T cells may be isolated from bone marrow, peripheral blood or a fraction of bone marrow or peripheral blood of a mammal, such as a patient, using a commercially available cell separation system. Alternatively, T cells may be derived from related or unrelated humans, non-human animals, cell lines or cultures. A sample comprising T cells may, for example, be peripheral blood mononuclear cells (PBMC).

As used herein, the term "NK cell" or "Natural Killer cell" refers to a subset of peripheral blood lymphocytes defined by the expression of CD56 or CD16 and the absence of the T cell receptor. As provided herein, the NK cell can also be differentiated from a stem cell or progenitor cell.

Nucleic Acids

The term "polynucleotide" or "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the invention, a polynucleotide is preferably isolated.

Nucleic acids may be comprised in a vector. The term "vector" as used herein includes any vectors known to the skilled person including plasmid vectors, cosmid vectors, phage vectors such as lambda phage, viral vectors such as retroviral, adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In one embodiment of all aspects of the invention, nucleic acid such as nucleic acid encoding an IL2 variant, nucleic acid encoding an IL2R variant polypeptide, nucleic acid encoding an antigen receptor or nucleic acid encoding a vaccine antigen is expressed in cells of the subject treated to provide the IL2 variant, IL2R variant polypeptide, antigen receptor or vaccine antigen. In one embodiment of all aspects of the invention, the nucleic acid is transiently expressed in cells of the subject. Thus, in one embodiment, the nucleic acid is not integrated into the genome of the cells. In one embodiment of all aspects of the invention, the nucleic acid is RNA, preferably in vitro transcribed RNA.

The nucleic acids described herein may be recombinant and/or isolated molecules.

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In one embodiment, the RNA may have modified ribonucleotides. Examples of modified ribonucleotides include, without limitation, 5-methylcytidine, pseudouridine and/or 1-methyl-pseudouridine.

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5' to 5' triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes.

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) tail. Thus, the 3'-UTR is upstream of the poly(A) sequence (if present), e.g. directly adjacent to the poly(A) sequence.

In some embodiments, the RNA according to the present disclosure comprises a 3'-poly(A) sequence. As used herein, the term "poly(A) sequence" or "poly-A tail" refers to an uninterrupted or interrupted sequence of adenylate residues which is typically located at the 3' end of an RNA molecule. Poly(A) sequences are known to those of skill in the art and may follow the 3' UTR in the RNAs described herein. The poly(A) sequence may be of any length. In some embodiments, a poly(A) sequence comprises or consists of at least 20, at least 30, at least 40, at least 80, or at least 100 and up to 500, up to 400, up to 300, up to 200, or up to 150 nucleotides, and, in particular, about 110 nucleotides.

In some embodiments, the poly(A) sequence only consists of A nucleotides. In some embodiments, the poly(A) sequence essentially consists of A nucleotides, but is interrupted by a random sequence of the four nucleotides (A, C, G, and U), as disclosed in WO 2016/005324 A1, hereby incorporated by reference. Such random sequence may be 5 to 50, 10 to 30, or 10 to 20 nucleotides in length. A poly(A) cassette present in the coding strand of DNA that essentially consists of dA nucleotides, but is interrupted by a random sequence having an equal distribution of the four nucleotides (dA, dC, dG, dT) and having a length of e.g. 5 to 50 nucleotides shows, on DNA level, constant propagation of plasmid DNA in *E. coli* and is still associated, on RNA level, with the beneficial properties with respect to supporting RNA stability and translational efficiency.

In some embodiments, no nucleotides other than A nucleotides flank a poly(A) sequence at its 3' end, i.e., the poly(A) sequence is not masked or followed at its 3' end by a nucleotide other than A.

In the context of the present disclosure, the term "transcription" relates to a process, wherein the genetic code in a DNA sequence is transcribed into RNA. Subsequently, the RNA may be translated into peptide or protein.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence.

As used herein, the terms "inked," "fused", or "fusion" are used interchangeably. These terms refer to the joining together of two or more elements or components or domains.

Cytokines

Cytokines are a category of small proteins (~5-20 kDa) that are important in cell signaling. Their release has an effect on the behavior of cells around them. Cytokines are involved in autocrine signaling, paracrine signaling and endocrine signaling as immunomodulating agents. Cytokines include chemokines, interferons, interleukins, lymphokines, and tumour necrosis factors but generally not hormones or growth factors (despite some overlap in the terminology). Cytokines are produced by a broad range of cells, including immune cells like macrophages, B lymphocytes, T lymphocytes and mast cells, as well as endothelial cells, fibroblasts, and various stromal cells. A given cytokine may be produced by more than one type of cell. Cytokines act through receptors, and are especially important in the immune system; cytokines modulate the balance between humoral and cell-based immune responses, and they regulate the maturation, growth, and responsiveness of particular cell populations. Some cytokines enhance or inhibit the action of other cytokines in complex ways.

IL2 and IL2R

Interleukin-2 (IL2) is a cytokine that induces proliferation of antigen-activated T cells and stimulates natural killer (NK) cells. The biological activity of IL2 is mediated through a multi-subunit IL2 receptor complex (IL2R) of three polypeptide subunits that span the cell membrane: p55 (IL2Rα, the alpha subunit, also known as CD25 in humans), p75 (IL2R$, the beta subunit, also known as CD122 in humans) and p64 (IL2Rγ, the gamma subunit, also known as CD132 in humans). T cell response to IL2 depends on a variety of factors, including: (1) the concentration of IL2; (2) the number of IL2R molecules on the cell surface; and (3) the number of IL2R occupied by IL2 (i.e., the affinity of the binding interaction between IL2 and IL2R (Smith, "Cell Growth Signal Transduction is Quantal" In Receptor Activation by Antigens, Cytokines, Hormones, and Growth Factors 766:263-271, 1995)). The IL2:IL2R complex is internalized upon ligand binding and the different components undergo differential sorting. When administered as an intravenous (i.v.) bolus, IL2 has a rapid systemic clearance (an initial clearance phase with a half-life of 12.9 minutes followed by a slower clearance phase with a half-life of 85 minutes) (Konrad et al., Cancer Res. 50:2009-2017, 1990).

In eukaryotic cells human IL2 is synthesized as a precursor polypeptide of 153 amino acids, from which amino acids are removed to generate mature secreted IL2. Recombinant human IL2 has been produced in E. coli, in insect cells and in mammalian COS cells.

Outcomes of systemic IL2 administration in cancer patients are far from ideal. While 15 to 20 percent of patients respond objectively to high-dose IL2, the great majority do not, and many suffer severe, life-threatening side effects, including nausea, confusion, hypotension, and septic shock. The severe toxicity associated with high-dose IL2 treatment is largely attributable to the activity of natural killer (NK) cells. Attempts to reduce serum concentration by reducing dose and adjusting dosing regimen have been attempted, and while less toxic, such treatments were also less efficacious.

According to the disclosure, in certain embodiments, the IL2 variant polypeptides described herein comprise a pharmacokinetic modifying group. In one embodiment, the IL2 variant portion or mutein described herein is attached to a pharmacokinetic modifying group. The resulting molecule, hereafter referred to as "extended-pharmacokinetic (PK) IL2," has a prolonged circulation half-life relative to free IL2. The prolonged circulation half-life of extended-PK IL2 permits in vivo serum IL2 concentrations to be maintained within a therapeutic range, potentially leading to the enhanced activation of many types of immune cells, including T cells. Because of its favorable pharmacokinetic profile, extended-PK IL2 can be dosed less frequently and for longer periods of time when compared with unmodified IL2.

As used herein, "half-life" refers to the time taken for the serum or plasma concentration of a compound such as a peptide or protein to reduce by 50%, in vivo, for example due to degradation and/or clearance or sequestration by natural mechanisms. An extended-PK cytokine such as an extended-PK interleukin (IL) suitable for use herein is stabilized in vivo and its half-life increased by, e.g., fusion to serum albumin (e.g., HSA or MSA), which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound to a subject; collecting blood samples or other samples from said subject at regular intervals; determining the level or concentration of the amino acid sequence or compound in said blood sample; and calculating, from (a plot of) the data thus obtained, the time until the level or concentration of the amino acid sequence or compound has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

According to the disclosure, IL2 (optionally as a portion of extended-PK IL2) may be naturally occurring IL2 or a fragment or variant thereof. IL2 may be human IL2 and may be derived from any vertebrate, especially any mammal.

As used herein, "human IL2" or "wild type human IL2" means IL2, whether native or recombinant, having the normally occurring 133 amino acid sequence of native human IL2 (less the signal peptide, consisting of an additional 20 N-terminal amino acids), whose amino acid sequence is described in Fujita, et. al, PNAS USA, 80, 7437-7441 (1983), with or without an additional N-terminal Methionine which is necessarily included when the protein is expressed as an intracellular fraction in E. coli. In one embodiment, human IL2 comprises the amino acid sequence of SEQ ID NO: 1. In one embodiment, a functional variant of human IL2 comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1. In one embodiment, a functional variant of IL2 binds to the IL2 receptor or a subunit of the IL2 receptor such as the alpha subunit and/or the beta/gamma subunit.

In certain embodiments described herein, the IL2 variant portion or mutein is fused to a heterologous polypeptide (i.e., a polypeptide that is not IL2 and preferably is not a variant of IL2). The heterologous polypeptide can increase the circulating half-life of IL2. As discussed in further detail infra, the polypeptide that increases the circulating half-life may be serum albumin, such as human or mouse serum albumin.

As used herein, "IL2 mutein" means a variant of IL2 (including functional variants thereof), in particular a polypeptide wherein specific substitutions to the IL2 protein have been made. In one embodiment, substitutions to the human IL2 protein have been made at at least a position that contacts the alpha subunit of the αβγ IL2 receptor complex (IL2Rαβγ). In one embodiment, such position has an acidic or basic amino acid residue in wild type human IL2, wherein if the amino acid residue is an acidic amino acid residue in wild type human IL2 the substitution is by a basic amino acid residue and if the amino acid residue is a basic amino acid residue in wild type human IL2 the substitution is by an acidic amino acid residue. Particularly preferred embodiments include the following: lysine (Lys) residue at position 35, lysine (Lys) residue at position 43, and glutamic acid (Glu) residue at position 61, relative to wild type human IL2 and numbered in accordance with wild type human IL2, or any combination thereof.

IL2 muteins may have an amino acid sequence identical to wild type IL2 at the other, non-substituted residues (i.e., the IL2 muteins comprise "mutCD25" mutations). However, the IL2 muteins may also be characterized by amino acid insertions, deletions, substitutions and modifications at one or more sites in or at the other residues of the native IL2 polypeptide chain. In accordance with this invention any such insertions, deletions, substitutions and modifications may result in an IL2 mutein that retains affinity for IL2Rβγ while having reduced affinity for IL2Rαβγ.

For example, the IL2 muteins may also be characterized by amino acid substitutions at one or more sites in or at the other residues of the native IL2 polypeptide chain such amino acid substitutions resulting, for example, in relatively increased affinity for IL2Rβγ when compared to wild type IL2 (i.e., the IL2 muteins in addition to the mutCD25 mutations also comprise "mutβγ" mutations). Such mutants are potent IL2 signaling agonists. These mutations can be at amino acid residues that contact IL2Rβ and/or IL2Rγ.

In various embodiments, the IL2 muteins described herein can differ from wild type IL2 by a substitution of one or more of the residues at positions 24, 65, 74, 80, 81, 85, 86, 89, 92, and 93 of wild type IL2. The substituted amino acid residue(s) can be, but are not necessarily, conservative substitutions.

For example, the mutation can be: I24V, P65H, Q74R, Q74H, Q74N, Q74S, L80F, L80V, R81I, R81T, R81D, L85V, I86V, I89V, I92F, V93I.

In one embodiment, an IL2 mutein is provided wherein the mutein comprises the following set of amino acid substitutions: 80F/81D/85V/86V/92F. The mutein may further comprise the amino acid substitution 42A. The mutein may further comprise one or more of the following amino acid substitutions: 24V, 65H, 74R, 74H, 74N, 74S, 89V, 93I.

In some embodiments, an IL2 mutein is provided wherein the mutein comprises a set of amino acid substitutions selected from the group consisting of:

(i) 74N, 80F, 81D, 85V, 86V, 89V, 92F;
(ii) 74H, 80F, 81D, 85V, 86V, 92F;
(iii) 74S, 80F, 81D, 85V, 86V, 92F;
(iv) 74N, 80F, 81D, 85V, 86V, 92F;
(v) 80F, 81D, 85V, 86V, 92F;
(vi) 80F, 81D, 85V, 86V, 89V, 92F, 93I;
(vii) 18R, 22E, 80F, 81D, 85V, 86V, 89V, 92F, 93I, 126T;
(viii) 18R, 22E, 74S, 80F, 81T, 85V, 86V, 89V, 92F, 93I, 126T.

By "numbered in accordance with wild type IL2" we mean identifying a chosen amino acid with reference to the position at which that amino acid normally occurs in the mature sequence of wild type IL2. Where insertions or deletions are made to the IL2 mutein, one of skill in the art will appreciate that an amino acid normally occurring at a certain position may be shifted in position in the mutein. However, the location of the shifted amino acid can be readily determined by inspection and correlation of the flanking amino acids with those flanking the amino acid in wild type IL2.

The IL2 variant polypeptides described herein and polynucleotides coding therefor can be produced by any suitable method known in the art. Such methods include introducing appropriate nucleotide changes into the nucleic acid encoding IL2 or by in vitro synthesis of the IL2 polynucleotide or protein. For example, a DNA sequence encoding the IL2 variant polypeptide described herein may be constructed and those sequences may be expressed in a suitably transformed host or in any other suitable expression system. This method will produce the IL2 variant polypeptides described herein and/or RNA encoding therefor. However, the IL2 variant polypeptides described herein and polynucleotides coding therefor may also be produced, albeit less preferably, by chemical synthesis.

IL2 variant polypeptides described herein may bind IL2Rαβγ with an affinity that is lower than the affinity with which the IL2 variant polypeptide binds IL2Rα'βγ (α' is a variant alpha subunit of IL2R described herein). Affinity of IL2 variant polypeptides described herein to IL2Rαβγ may be at least 2-fold, at least 5-fold, at least 10-fold, at least 20-fold, at least 50-fold, or at least 100-fold lower than the affinity with which the IL2 variant polypeptide binds IL2Rα'βγ.

IL2 variant polypeptides described herein may bind IL2Rαβγ with an affinity that is lower than the affinity with which wild type IL2 binds IL2Rαβγ. Affinity of IL2 variant polypeptides described herein to IL2Rαβγ may be at least 2-fold, at least 5-fold, at least 10-fold, at least 20-fold, at least 50-fold, or at least 100-fold lower than the affinity with which wild type IL2 binds IL2Rαβγ.

IL2 variant polypeptides described herein may bind IL2Rβγ with an affinity that is greater than the affinity with which wild type IL2 binds IL2Rβγ. Affinity of IL2 variant polypeptides described herein to IL2Rβγ may be at least 2-fold, at least 5-fold, at least 10-fold, at least 20-fold, at least 50-fold, or at least 100-fold greater than the affinity with which wild type IL2 binds IL2Rβγ.

IL2 variant polypeptides described herein may have a decreased ability to stimulate regulatory T cells than wild type IL2, in particular when compared to the ability to stimulate effector T cells and/or NK cells.

IL2 variant polypeptides described herein may have a mutation (e.g., a deletion, addition, or substitution) of 1, 2, 3, 4, 5, 6, 7, 8, 9, 10, 11, 12, 13, 14, 15, 16, 17, 18, 19, 20, or more amino acid residues relative to wild type IL2.

IL2 variant polypeptides described herein may include an amino acid sequence that is at least about 50%, at least about 65%, at least about 70%, at least about 80%, at least about 85%, at least about 87%, at least about 90%, at least about 95%, at least about 97%, at least about 98%, or at least about 99% identical to wild type IL2.

In one embodiment, the IL2 variant polypeptides described herein have one or more, preferably all of the following properties:
1) Agonist action at IL2Rβγ. This property can be evaluated directly in in vitro proliferation assays with cell lines dependent on IL2.
2) Loss of capacity, as compared to wild type IL2, to stimulate in vitro and/or in vivo populations of regulatory T cells. This property can be assessed, for instance, by studying the ability of the muteins, as compared to those of wild type IL2, to induce expansion of regulatory T cells.
3) Increased therapeutic effect with respect to the native IL2 in animal models. This property can be assessed, for example, by comparing the antitumor or anti-metastatic effect of the IL2 variant polypeptides described herein and the wild type IL2 as monotherapy in transplantable tumor models (e.g. B16 melanoma). It can also be evaluated through the potentiating effect of the cellular and/or humoral response to a vaccine of interest.

Many immune cells transiently up-regulate IL2Rαβγ upon activation to increase IL2 sensitivity when mounting an immunological response, including priming of CD8 T cells. Since some IL2Rαβγ binding by IL2 may be necessary, the present invention envisions the use of a mixture of IL2 variant polypeptides described herein in combination with IL2 (including functional variants thereof) that does not demonstrate reduced affinity towards IL2Rαβγ, such as wild type IL2. In certain embodiments, the molar ratio of IL2 variant polypeptides described herein to IL2 that does not demonstrate reduced affinity towards IL2Rαβγ is from 50:1 to 1:1, 20:1 to 2:1, 10:1 to 5:1, or 5:1 to 3:1.

According to the disclosure, alpha subunit of IL2 receptor (IL2R) or IL2Rα may be naturally occurring IL2Rα or a fragment or variant thereof. IL2Rα may be human IL2Rα and may be derived from any vertebrate, especially any mammal.

As used herein, "human IL2Rα" or "wild type human IL2Rα" means IL2Rα, whether native or recombinant, having the normally occurring 251 amino acid sequence of native human IL2Rα (less the signal peptide, consisting of an additional 21 N-terminal amino acids). Human IL2Rα, whether native or recombinant, including the signal peptide, consisting of an additional 21 N-terminal amino acids, has the 272 amino acid sequence shown in SEQ ID NO: 4. In one embodiment, human IL2Rα comprises the amino acid sequence of SEQ ID NO: 2 or SEQ ID NO: 4. In one embodiment, a functional variant of human IL2Rα comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or SEQ ID NO: 4. In one embodiment, a functional variant of IL2Rα, optionally as part of IL2Rαβγ, binds to IL2.

As used herein, "IL2Rα mutein" means a variant of IL2Rα (including functional variants thereof), in particular a polypeptide wherein specific substitutions to the IL2Rα protein have been made. In one embodiment, substitutions to the human IL2Rα protein have been made at at least a position that contacts IL2. In one embodiment, such position has an acidic or basic amino acid residue in wild type human IL2Rα, wherein if the amino acid residue is an acidic amino acid residue in wild type human IL2Rα the substitution is by a basic amino acid residue and if the amino acid residue is a basic amino acid residue in wild type human IL2Rα the substitution is by an acidic amino acid residue. Particularly preferred embodiments include the following: glutamic acid (Glu) residue at position 1, glutamic acid (Glu) residue at position 29, and lysine (Lys) residue at position 38, relative to wild type human IL2Rα and numbered in accordance with wild type human IL2Rα, or any combination thereof.

IL2Rα muteins may have an amino acid sequence identical to wild type IL2Rα at the other, non-substituted residues. However, the IL2Rα muteins may also be characterized by amino acid insertions, deletions, substitutions and modifications at one or more sites in or at the other residues of the native IL2Rα polypeptide chain.

By "numbered in accordance with wild type IL2Rα" we mean identifying a chosen amino acid with reference to the position at which that amino acid normally occurs in the mature sequence of wild type IL2Rα. Where insertions or deletions are made to the IL2Rα mutein, one of skill in the art will appreciate that an amino acid normally occurring at a certain position may be shifted in position in the mutein. However, the location of the shifted amino acid can be readily determined by inspection and correlation of the flanking amino acids with those flanking the amino acid in wild type IL2Rα.

The IL2Rα variant polypeptides described herein and polynucleotides coding therefor can be produced by any suitable method known in the art. Such methods include introducing appropriate nucleotide changes into the nucleic acid encoding IL2Rα or by in vitro synthesis of the IL2Rα polynucleotide or protein. For example, a DNA sequence encoding the IL2Rα variant polypeptide described herein may be constructed and those sequences may be expressed in a suitably transformed host or in any other suitable expression system. This method will produce the IL2Rα variant polypeptides described herein and/or RNA encoding therefor. However, the IL2Rα variant polypeptides described herein and polynucleotides coding therefor may also be produced, albeit less preferably, by chemical synthesis.

Extended-PK Group

IL2 variant polypeptides described herein can be prepared as fusion or chimeric polypeptides that include an IL2 variant portion and a heterologous polypeptide (i.e., a polypeptide that is not IL2 or a variant thereof). The IL2 variants may be fused to an extended-PK group, which increases circulation half-life. Non-limiting examples of extended-PK groups are described infra. It should be understood that other PK groups that increase the circulation half-life of cytokines, or variants thereof, are also applicable to the present disclosure. In certain embodiments, the extended-PK group is a serum albumin domain (e.g., mouse serum albumin, human serum albumin).

As used herein, the term "PK" is an acronym for "pharmacokinetic" and encompasses properties of a compound including, by way of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include serum albumin (e.g., HSA), Immunoglobulin Fc or Fc fragments and variants thereof, transferrin and variants thereof, and human serum albumin (HSA) binders (as disclosed in U.S. Publication Nos. 2005/0287153 and 2007/0003549). Other exemplary extended-PK groups are disclosed in Kontermann, Expert Opin Biol Ther, 2016 July; 16(7):903-15 which is herein incorporated by reference in its entirety. As used herein, an "extended-PK cytokine" refers to a cytokine moiety in combination with an extended-PK group. In one embodiment, the extended-PK cytokine is a fusion protein in which a cytokine moiety is linked or fused to an extended-PK group. As used herein, an "extended-PK IL" refers to an interleukin (IL) moiety (including an IL variant moiety) in combination with an extended-PK group. In one embodiment, the extended-PK IL is a fusion protein in which an IL moiety is linked or fused to an extended-PK group. An exemplary fusion protein is an HSA/IL2 fusion in which an IL2 moiety is fused with HSA.

In certain embodiments, the serum half-life of an extended-PK IL is increased relative to the IL alone (i.e., the IL not fused to an extended-PK group). In certain embodiments, the serum half-life of the extended-PK IL is at least 20, 40, 60, 80, 100, 120, 150, 180, 200, 400, 600, 800, or 1000% longer relative to the serum half-life of the IL alone. In certain embodiments, the serum half-life of the extended-PK IL is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the IL alone. In certain embodiments, the serum half-life of the extended-PK IL is at least hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

In certain embodiments, the extended-PK group includes serum albumin, or fragments thereof or variants of the serum albumin or fragments thereof (all of which for the purpose of the present disclosure are comprised by the term 'albumin'). Polypeptides described herein may be fused to albumin (or a fragment or variant thereof) to form albumin fusion proteins. Such albumin fusion proteins are described in U.S. Publication No. 20070048282.

As used herein, "albumin fusion protein" refers to a protein formed by the fusion of at least one molecule of albumin (or a fragment or variant thereof) to at least one molecule of a protein such as a therapeutic protein, in particular IL2 (or variant thereof). The albumin fusion protein may be generated by translation of a nucleic acid in which a polynucleotide encoding a therapeutic protein is joined in-frame with a polynucleotide encoding an albumin. The therapeutic protein and albumin, once part of the albumin fusion protein, may each be referred to as a "portion", "region" or "moiety" of the albumin fusion protein (e.g., a "therapeutic protein portion" or an "albumin protein portion"). In a highly preferred embodiment, an albumin fusion protein comprises at least one molecule of a therapeutic protein (including, but not limited to a mature form of the therapeutic protein) and at least one molecule of albumin (including but not limited to a mature form of albumin). In one embodiment, an albumin fusion protein is processed by a host cell such as a cell of the target organ for administered RNA, e.g. a liver cell, and secreted into the circulation. Processing of the nascent albumin fusion protein that occurs in the secretory pathways of the host cell used for expression of the RNA may include, but is not limited to signal peptide cleavage; formation of disulfide bonds; proper folding; addition and processing of carbohydrates (such as for example, N- and O-linked glycosylation); specific proteolytic cleavages; and/or assembly into multimeric proteins. An albumin fusion protein is preferably encoded by RNA in a non-processed form which in particular has a signal peptide at its N-terminus and following secretion by a cell is preferably present in the processed form wherein in particular the signal peptide has been cleaved off. In a most preferred embodiment, the "processed form of an albumin fusion protein" refers to an albumin fusion protein product which has undergone N-terminal signal peptide cleavage, herein also referred to as a "mature albumin fusion protein".

In preferred embodiments, albumin fusion proteins comprising a therapeutic protein have a higher plasma stability compared to the plasma stability of the same therapeutic protein when not fused to albumin. Plasma stability typically refers to the time period between when the therapeutic protein is administered in vivo and carried into the bloodstream and when the therapeutic protein is degraded and cleared from the bloodstream, into an organ, such as the kidney or liver that ultimately clears the therapeutic protein from the body. Plasma stability is calculated in terms of the half-life of the therapeutic protein in the bloodstream. The half-life of the therapeutic protein in the bloodstream can be readily determined by common assays known in the art.

As used herein, "albumin" refers collectively to albumin protein or amino acid sequence, or an albumin fragment or variant, having one or more functional activities (e.g., biological activities) of albumin. In particular, "albumin" refers to human albumin or fragments or variants thereof especially the mature form of human albumin, or albumin from other vertebrates or fragments thereof, or variants of these molecules. The albumin may be derived from any vertebrate, especially any mammal, for example human, mouse, cow, sheep, or pig. Non-mammalian albumins include, but are not limited to, hen and salmon. The albumin portion of the albumin fusion protein may be from a different animal than the therapeutic protein portion.

In certain embodiments, the albumin is human serum albumin (HSA), or fragments or variants thereof, such as those disclosed in U.S. Pat. No. 5,876,969, WO 2011/124718, WO 2013/075066, and WO 2011/0514789.

The terms, human serum albumin (HSA) and human albumin (HA) are used interchangeably herein. The terms, "albumin and "serum albumin" are broader, and encompass human serum albumin (and fragments and variants thereof) as well as albumin from other species (and fragments and variants thereof).

As used herein, a fragment of albumin sufficient to prolong the therapeutic activity or plasma stability of the therapeutic protein refers to a fragment of albumin sufficient in length or structure to stabilize or prolong the therapeutic activity or plasma stability of the protein so that the plasma stability of the therapeutic protein portion of the albumin fusion protein is prolonged or extended compared to the plasma stability in the non-fusion state.

The albumin portion of the albumin fusion proteins may comprise the full length of the albumin sequence, or may include one or more fragments thereof that are capable of stabilizing or prolonging the therapeutic activity or plasma stability. Such fragments may be of 10 or more amino acids in length or may include about 15, 20, 25, 30, 50, or more contiguous amino acids from the albumin sequence or may include part or all of specific domains of albumin. For instance, one or more fragments of HSA spanning the first two immunoglobulin-like domains may be used. In a preferred embodiment, the HSA fragment is the mature form of HSA.

Generally speaking, an albumin fragment or variant will be at least 100 amino acids long, preferably at least 150 amino acids long.

According to the disclosure, albumin may be naturally occurring albumin or a fragment or variant thereof. Albumin may be human albumin and may be derived from any vertebrate, especially any mammal. In one embodiment, albumin comprises the amino acid sequence of SEQ ID NO: 3 or an amino acid sequence that is at least 80%, 81%. 82%, 83%, 84%, 85%, 86%, 87%, 88%, 89%, 90%, 91%, 92%, 93%, 94%, 95%, 96%, 97%, 98%, or 99% identical to SEQ ID NO: 3.

Preferably, the albumin fusion protein comprises albumin as the N-terminal portion, and a therapeutic protein as the C-terminal portion. Alternatively, an albumin fusion protein comprising albumin as the C-terminal portion, and a therapeutic protein as the N-terminal portion may also be used.

In one embodiment, the therapeutic protein(s) is (are) joined to the albumin through (a) peptide linker(s). A linker peptide between the fused portions may provide greater physical separation between the moieties and thus maximize the accessibility of the therapeutic protein portion, for instance, for binding to its cognate receptor. The linker peptide may consist of amino acids such that it is flexible or more rigid. The linker sequence may be cleavable by a protease or chemically.

As used herein, the term "Fc region" refers to the portion of a native immunoglobulin formed by the respective Fc domains (or Fc moieties) of its two heavy chains. As used herein, the term "Fc domain" refers to a portion or fragment of a single immunoglobulin (Ig) heavy chain wherein the Fc domain does not comprise an Fv domain. In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains of a polypeptide described herein may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

In certain embodiments, an extended-PK group includes an Fc domain or fragments thereof or variants of the Fc domain or fragments thereof (all of which for the purpose of the present disclosure are comprised by the term "Fc domain"). The Fc domain does not contain a variable region that binds to antigen. Fc domains suitable for use in the present disclosure may be obtained from a number of different sources. In certain embodiments, an Fc domain is derived from a human immunoglobulin. In certain embodiments, the Fc domain is from a human IgG1 constant region. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species.

Moreover, the Fc domain (or a fragment or variant thereof) may be derived from any immunoglobulin class, including IgM, IgG, IgD, IgA, and IgE, and any immunoglobulin isotype, including IgG1, IgG2, IgG3, and IgG4.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or fragments or variants thereof) can be derived from these sequences using art recognized techniques.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety. In certain embodiments, the extended- PK group is transferrin, as disclosed in U.S. Pat. Nos. 7,176,278 and 8,158,579, which are herein incorporated by reference in their entirety. In certain embodiments, the extended-PK group is a serum immunoglobulin binding protein such as those disclosed in US2007/0178082, US2014/0220017, and US2017/0145062, which are herein incorporated by reference in their entirety. In certain embodiments, the extended-PK group is a fibronectin (Fn)-based scaffold domain protein that binds to serum albumin, such as those disclosed in US20120094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

In certain aspects, the extended-PK IL, suitable for use according to the disclosure, can employ one or more peptide linkers. As used herein, the term "peptide linker" refers to a peptide or polypeptide sequence which connects two or more domains (e.g., the extended-PK moiety and an IL moiety such as IL2) in a linear amino acid sequence of a polypeptide chain. For example, peptide linkers may be used to connect an IL2 moiety to a HSA domain.

Linkers suitable for fusing the extended-PK group to e.g. IL2 are well known in the art. Exemplary linkers include glycine-seine-polypeptide linkers, glycine-proline-polypeptide linkers, and proline-alanine polypeptide linkers. In certain embodiments, the linker is a glycine-serine-polypeptide linker, i.e., a peptide that consists of glycine and serine residues.

In addition to, or in place of, the heterologous polypeptides described above, an IL2 variant polypeptide described herein can contain sequences encoding a "marker" or "reporter". Examples of marker or reporter genes include β-lactamase, chloramphenicol acetyltransferase (CAT), adenosine deaminase (ADA), aminoglycoside phosphotransferase, dihydrofolate reductase (DHFR), hygromycin-B-phosphotransferase (HPH), thymidine kinase (TK), β-galactosidase, and xanthine guanine phosphoribosyltransferase (XGPRT).

Antigen Receptors

Cells described herein such as immune effector cells that may be modified (e.g., ex vivo/in vitro or in vivo in a subject to be treated) to express an IL2R variant polypeptide described herein may express an antigen receptor such as a T cell receptor (TCR) or chimeric antigen receptor (CAR) binding antigen or a procession product thereof, in particular when present on or presented by a target cell. Cells may naturally express an antigen receptor or be modified (e.g., ex vivo/in vitro or in vivo in a subject to be treated) to express an antigen receptor. In one embodiment, modification to express an IL2R variant polypeptide described herein and modification to express an antigen receptor take place ex vivo/in vitro, either simultaneously or at different time points. Subsequently, modified cells may be administered to a patient.

In one embodiment, modification to express an IL2R variant polypeptide described herein takes place ex viva/n vitro, and, following administration of the cells to a patient, modification to express an antigen receptor takes place in vivo. In one embodiment, modification to express an antigen receptor takes place ex vivo/in vitro, and, following administration of the cells to a patient, modification to express an IL2R variant polypeptide described herein takes place in vivo. In one embodiment, modification to express an IL2R variant polypeptide described herein and modification to express an antigen receptor takes place in vivo, either simultaneously or at different time points. The cells may be endogenous cells of the patient or may have been administered to a patient.

Chimeric Antigen Receptors

Adoptive cell transfer therapy with CAR-engineered T cells expressing chimeric antigen receptors is a promising anti-cancer therapeutic as CAR-modified T cells can be engineered to target virtually any tumor antigen. For example, patient's T cells may be genetically engineered (genetically modified) to express CARs specifically directed towards antigens on the patient's tumor cells, then infused back into the patient.

According to the invention, the term "CAR" (or "chimeric antigen receptor") is synonymous with the terms "chimeric T cell receptor" and "artificial T cell receptor" and relates to an artificial receptor comprising a single molecule or a complex of molecules which recognizes, i.e. binds to, a target structure (e.g. an antigen) on a target cell such as a cancer cell (e.g. by binding of an antigen binding domain to an antigen expressed on the surface of the target cell) and may confer specificity onto an immune effector cell such as a T cell expressing said CAR on the cell surface. Preferably, recognition of the target structure by a CAR results in activation of an immune effector cell expressing said CAR. A CAR may comprise one or more protein units said protein units comprising one or more domains as described herein. The term "CAR" does not include T cell receptors.

A CAR comprises a target-specific binding element otherwise referred to as an antigen binding moiety or antigen binding domain that is generally part of the extracellular domain of the CAR. The antigen binding domain recognizes a ligand that acts as a cell surface marker on target cells associated with a particular disease state. Specifically, the CAR of the invention targets the antigen such as tumor antigen on a diseased cell such as tumor cell.

In one embodiment, the binding domain in the CAR binds specifically to the antigen. In one embodiment, the antigen to which the binding domain in the CAR binds is expressed in a cancer cell (tumor antigen). In one embodiment, the antigen is expressed on the surface of a cancer cell. In one embodiment, the binding domain binds to an extracellular domain or to an epitope in an extracellular domain of the antigen. In one embodiment, the binding domain binds to native epitopes of the antigen present on the surface of living cells.

In one embodiment of the invention, an antigen binding domain comprises a variable region of a heavy chain of an immunoglobulin (VH) with a specificity for the antigen and a variable region of a light chain of an immunoglobulin (VL) with a specificity for the antigen. In one embodiment, an immunoglobulin is an antibody. In one embodiment, said heavy chain variable region (VH) and the corresponding light chain variable region (VL) are connected via a peptide linker. Preferably, the antigen binding moiety portion in the CAR is a scFv.

The CAR is designed to comprise a transmembrane domain that is fused to the extracellular domain of the CAR. In one embodiment, the transmembrane domain is not naturally associated with one of the domains in the CAR. In one embodiment, the transmembrane domain is naturally associated with one of the domains in the CAR. In one embodiment, the transmembrane domain is modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain.

In some instances, the CAR of the invention comprises a hinge domain which forms the linkage between the transmembrane domain and the extracellular domain.

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

In one embodiment, the CAR comprises a primary cytoplasmic signaling sequence derived from CD3-zeta. Further, the cytoplasmic domain of the CAR may comprise the CD3-zeta signaling domain combined with a costimulatory signaling region.

The identity of the co-stimulation domain is limited only in that it has the ability to enhance cellular proliferation and survival upon binding of the targeted moiety by the CAR. Suitable co-stimulation domains include CD28, CD137 (4-1BB), a member of the tumor necrosis factor receptor (TNFR) superfamily, CD134 (OX40), a member of the TNFR-superfamily of receptors, and CD278 (ICOS), a CD28-superfamily co-stimulatory molecule expressed on activated T cells. The skilled person will understand that sequence variants of these noted co-stimulation domains can be used without adversely impacting the invention, where the variants have the same or similar activity as the domain on which they are modeled. Such variants will have at least about 80% sequence identity to the amino acid sequence of the domain from which they are derived. In some embodiments of the invention, the CAR constructs comprise two co-stimulation domains. While the particular combinations include all possible variations of the four noted domains, specific examples include CD28+CD137 (4-1BB) and CD28+CD134 (OX40).

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the CAR comprises a signal peptide which directs the nascent protein into the endoplasmic reticulum. In one embodiment, the signal peptide precedes the antigen binding domain. In one embodiment, the signal peptide is derived from an immunoglobulin such as IgG.

The term "antibody" includes an immunoglobulin comprising at least two heavy (H) chains and two light (L) chains inter-connected by disulfide bonds. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. An antibody binds, preferably specifically binds with an antigen. Antibodies can be intact immunoglobulins derived from natural sources or from recombinant sources and can be immunoreactive portions or fragments of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab')$_2$, as well as single chain antibodies and humanized antibodies (Harlow et al., 1999, In: Using Antibodies: A Laboratory Manual, Cold Spring Harbor Laboratory Press, NY; Harlow et al., 1989, in: Antibodies: A Laboratory Manual, Cold Spring Harbor, New York; Houston et al., 1988, Proc. Natl. Acad. Sci. USA 85:5879-5883; Bird et al., 1988, Science 242:423-426). Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "antibody fragment" refers to a portion of an intact antibody and typically comprises the antigenic determining variable regions of an intact antibody.

Examples of antibody fragments include, but are not limited to, Fab, Fab', F(ab')$_2$, and Fv fragments, linear antibodies, scFv antibodies, and multispecific antibodies formed from antibody fragments.

An "antibody heavy chain", as used herein, refers to the larger of the two types of polypeptide chains present in antibody molecules in their naturally occurring conformations.

An "antibody light chain", as used herein, refers to the smaller of the two types of polypeptide chains present in antibody molecules in their naturally occurring conformations, κ and λ light chains refer to the two major antibody light chain isotypes.

According to the disclosure, a CAR which when present on a T cell recognizes an antigen such as on the surface of antigen presenting cells or diseased cells such as cancer cells, such that the T cell is stimulated, and/or expanded or exerts effector functions as described above.

Genetic Modification of Immune Effector Cells

A variety of methods may be used to introduce IL2 receptor polypeptides such as IL2Rα variants described herein and optionally antigen receptors such as CAR constructs into calls such as T cells to produce cells genetically modified to express the IL2 receptor polypeptides such as IL2Rα variants described herein and optionally antigen receptors. Such methods including non-viral-based DNA transfection, non-viral-based RNA transfection, e.g., mRNA transfection, transposon-based systems, and viral-based systems. Non-viral-based DNA transfection has low risk of insertional mutagenesis. Transposon-based systems can integrate transgenes more efficiently than plasmids that do not contain an integrating element. Viral-based systems include the use of γ-retroviruses and lentiviral vectors. γ-Retroviruses are relatively easy to produce, efficiently and permanently transduce T cells, and have preliminarily proven safe from an integration standpoint in primary human T cells. Lentiviral vectors also efficiently and permanently transduce T cells but are more expensive to manufacture. They are also potentially safer than retrovirus based systems.

In one embodiment of all aspects of the invention, T cells or T cell progenitors are transfected either ex vivo or in vivo with nucleic acid encoding the IL2 receptor polypeptide and optionally nucleic acid encoding the antigen receptor. In one embodiment, a combination of ex vivo and in vivo transfection may be used. In one embodiment of all aspects of the invention, the T cells or T cell progenitors are from the subject to be treated. In one embodiment of all aspects of the invention, the T cells or T cell progenitors are from a subject which is different to the subject to be treated.

CAR T cells may be produced in vivo, and therefore nearly instantaneously, using nanoparticles targeted to T cells. For example, poly(β-amino ester)-based nanoparticles may be coupled to anti-CD3e F(ab) fragments for binding to CD3 on T cells. Upon binding to T cells, these nanoparticles are endocytosed. Their contents, for example plasmid DNA encoding an anti-tumor antigen CAR, may be directed to the T cell nucleus due to the inclusion of peptides containing microtubule-associated sequences (MTAS) and nuclear localization signals (NLSs). The inclusion of transposons flanking the CAR gene expression cassette and a separate plasmid encoding a hyperactive transposase, may allow for the efficient integration of the CAR vector into chromosomes. Such system that allows for the in vivo production of CAR T cells following nanoparticle infusion is described in Smith et al. (2017) Nat. Nanotechnol. 12:813-820.

Another possibility is to use the CRISPR/Cas9 method to deliberately place a CAR coding sequence at a specific locus. For example, existing T cell receptors (TCR) may be knocked out, while knocking in the CAR and placing it under the dynamic regulatory control of the endogenous promoter that would otherwise moderate TCR expression; c.f., e.g., Eyquem et al. (2017) Nature 543:113-117.

In one embodiment of all aspects of the invention, the cells genetically modified to express one or more IL2 receptor polypeptides such as IL2Rα variants described herein and optionally an antigen receptor are stably or transiently transfected with nucleic acid encoding the IL2 receptor polypeptides such as IL2Rα variants described herein and optionally nucleic acid encoding the antigen receptor. In one embodiment, the cells are stably transfected with some nucleic acid and transiently transfected with other nucleic acid. Thus, the nucleic acid encoding the IL2 receptor polypeptides such as IL2Rα variants described herein and optionally the nucleic acid encoding the antigen receptor is integrated or not integrated into the genome of the cells.

In one embodiment of all aspects of the invention, the cells genetically modified to express an antigen receptor are inactivated for expression of an endogenous T cell receptor and/or endogenous HLA.

In one embodiment of all aspects of the invention, the cells described herein may be autologous, allogeneic or syngeneic to the subject to be treated. In one embodiment, the present disclosure envisions the removal of cells from a patient and the subsequent re-delivery of the cells to the patient. In one embodiment, the present disclosure does not envision the removal of cells from a patient. In the latter case all steps of genetic modification of cells are performed in vivo.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

Antigen

In one embodiment, the methods described herein further comprise the step of contacting the immune effector cells, in particular immune effector cells expressing an antigen receptor, e.g., immune effector cells which are genetically manipulated to express an antigen receptor, either ex vivo or in the subject being treated, with a cognate antigen molecule, wherein the antigen molecule or a procession product thereof, e.g., a fragment thereof, binds to the antigen receptor such as TCR or CAR carried by the immune effector cells. In one embodiment, the cognate antigen molecule is selected from the group consisting of the antigen expressed by a target cell to which the immune effector cells are targeted or a fragment thereof, or a variant of the antigen or the fragment. In one embodiment, the immune effector cells are contacted with the cognate antigen molecule under conditions such that expansion and/or activation of the immune effector cells occurs. In one embodiment, the step of contacting the immune effector cells with the cognate antigen molecule takes place in vivo or ex vivo.

In one embodiment, the methods described herein comprise the step of administering the cognate antigen molecule or a nucleic acid coding therefor to the subject. In one embodiment, the nucleic acid encoding the cognate antigen molecule is expressed in cells of the subject to provide the cognate antigen molecule. In one embodiment, expression of the cognate antigen molecule is at the cell surface. In one embodiment, the nucleic acid encoding the cognate antigen molecule is transiently expressed in cells of the subject. In one embodiment, the nucleic encoding the cognate antigen molecule is RNA. In one embodiment, the cognate antigen molecule or the nucleic acid coding therefor is administered systemically. In one embodiment, after systemic administration of the nucleic acid encoding the cognate antigen molecule, expression of the nucleic acid encoding the cognate antigen molecule in spleen occurs. In one embodiment, after systemic administration of the nucleic acid encoding the cognate antigen molecule, expression of the nucleic acid encoding the cognate antigen molecule in antigen presenting cells, preferably professional antigen presenting cells, occurs. In one embodiment, the antigen presenting cells are selected from the group consisting of dendritic cells, macrophages and B cells. In one embodiment, after systemic administration of the nucleic acid encoding the cognate antigen molecule, no or essentially no expression of the nucleic acid encoding the cognate antigen molecule in lung and/or liver occurs. In one embodiment, after systemic administration of the nucleic acid encoding the cognate antigen molecule, expression of the nucleic acid encoding the cognate antigen molecule in spleen is at least 5-fold the amount of expression in lung.

A peptide and protein antigen which is provided to a subject according to the invention (either by administering the peptide and protein antigen or a nucleic acid, in particular RNA, encoding the peptide and protein antigen), i.e., a vaccine antigen, preferably results in stimulation, priming and/or expansion of immune effector cells in the subject being administered the peptide or protein antigen or nucleic acid. Said stimulated, primed and/or expanded immune effector cells are preferably directed against a target antigen, in particular a target antigen expressed by diseased cells, tissues and/or organs, i.e., a disease-associated antigen. Thus, a vaccine antigen may comprise the disease-associated antigen, or a fragment or variant thereof. In one embodiment, such fragment or variant is immunologically equivalent to the disease-associated antigen. In the context of the present disclosure, the term "fragment of an antigen" or "variant of an antigen" means an agent which results in stimulation, priming and/or expansion of immune effector cells which stimulated, primed and/or expanded immune effector cells target the antigen, i.e. a disease-associated antigen, in particular when presented by diseased cells, tissues and/or organs. Thus, the vaccine antigen may correspond to or may comprise the disease-associated antigen, may correspond to or may comprise a fragment of the disease-associated antigen or may correspond to or may comprise an antigen which is homologous to the disease-associated antigen or a fragment thereof. If the vaccine antigen comprises a fragment of the disease-associated antigen or an amino acid sequence which is homologous to a fragment of the disease-associated antigen said fragment or amino acid sequence may comprise an epitope of the disease-associated antigen to which the antigen receptor of the immune effector cells is targeted or a sequence which is homologous to an epitope of the disease-associated antigen. Thus, according to the disclosure, a vaccine antigen may comprise an immunogenic fragment of a disease-associated antigen or an amino acid sequence being homologous to an immunogenic fragment of a disease-associated antigen. An "immunogenic fragment of an antigen" according to the disclosure preferably relates to a fragment of an antigen which is capable of stimulating, priming and/or expanding immune effector cells carrying an antigen receptor binding to the antigen or cells expressing the antigen. It is preferred that the vaccine antigen (similar to the disease-associated antigen) provides the relevant epitope for binding by the antigen binding domain present in the immune effector cells. In one embodiment, the vaccine antigen (similar to the disease-associated antigen) is expressed on the surface of a cell such as an antigen-presenting cell so as to provide the relevant epitope for binding by immune effector cells. The vaccine antigen may be a recombinant antigen.

In one embodiment of all aspects of the invention, the nucleic acid encoding the vaccine antigen is expressed in cells of a subject to provide the antigen or a procession product thereof for binding by the antigen receptor expressed by immune effector cells, said binding resulting in stimulation, priming and/or expansion of the immune effector cells.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present disclosure, the term "immunologically equivalent" is preferably used with respect to the immunological effects or properties of antigens or antigen variants used for immunization. For example, an amino acid sequence is immunologically equivalent to a reference amino acid sequence if said amino acid sequence when exposed to the immune system of a subject such as T cells binding to the reference amino acid sequence or cells expressing the reference amino acid sequence induces an immune reaction having a specificity of reacting with the reference amino acid sequence. Thus, a molecule which is immunologically equivalent to an antigen exhibits the same or essentially the same properties and/or exerts the same or essentially the same effects regarding the stimulation, priming and/or expansion of T cells as the antigen to which the T cells are targeted.

"Activation" or "stimulation", as used herein, refers to the state of an immune effector cell such as T cell that has been sufficiently stimulated to induce detectable cellular proliferation. Activation can also be associated with initiation of signaling pathways, induced cytokine production, and detectable effector functions. The term "activated immune effector cells" refers to, among other things, immune effector cells that are undergoing cell division.

The term "priming" refers to a process wherein an immune effector cell such as a T cell has its first contact with its specific antigen and causes differentiation into effector cells such as effector T cells.

The term "clonal expansion" or "expansion" refers to a process wherein a specific entity is multiplied. In the context of the present disclosure, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

The term "antigen" relates to an agent comprising an epitope against which an immune response can be generated. The term "antigen" includes, in particular, proteins and peptides. In one embodiment, an antigen is presented or present on the surface of cells of the immune system such as antigen presenting cells like dendritic cells or macrophages. An antigen or a procession product thereof such as a T cell epitope is in one embodiment bound by an antigen receptor. Accordingly, an antigen or a procession product thereof may react specifically with immune effector cells such as T-lymphocytes (T cells). In one embodiment, an antigen is a disease-associated antigen, such as a tumor antigen, a viral antigen, or a bacterial antigen and an epitope is derived from such antigen.

The term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen or an epitope thereof may therefore be used for therapeutic purposes. Disease-associated antigens may be associated with infection by microbes, typically microbial antigens, or associated with cancer, typically tumors.

The term "tumor antigen" refers to a constituent of cancer cells which may be derived from the cytoplasm, the cell surface and the cell nucleus. In particular, it refers to those antigens which are produced intracellularly or as surface antigens on tumor cells. A tumor antigen is typically expressed preferentially by cancer cells (e.g., it is expressed at higher levels in cancer cells than in non-cancer cells) and in some instances it is expressed solely by cancer cells. Examples of tumor antigens include, without limitation, p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap 100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A 10, MAGE-A 11, or MAGE-A12, MAGE-B, MAGE-C, MART-1/Melan-A, MC1R, Myosin/m, MUC1, MUM-1, MUM-2, MUM-3, NA88-A, NF1, NY-ESO-1, NY-BR-1, p190 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, and WT-1.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "expressed on the cell surface" or "associated with the cell surface" means that a molecule such as a receptor or antigen is associated with and located at the plasma membrane of a cell, wherein at least a part of the molecule faces the extracellular space of said cell and is accessible from the outside of said cell, e.g., by antibodies located outside the cell. In this context, a part is preferably at least 4, preferably at least 8, preferably at least 12, more preferably at least 20 amino acids. The association may be direct or indirect. For example, the association may be by one or more transmembrane domains, one or more lipid anchors, or by the interaction with any other protein, lipid, saccharide, or other structure that can be found on the outer leaflet of the plasma membrane of a cell. For example, a molecule associated with the surface of a cell may be a transmembrane protein having an extracellular portion or may be a protein associated with the surface of a cell by interacting with another protein that is a transmembrane protein.

"Cell surface" or "surface of a cell" is used in accordance with its normal meaning in the art, and thus includes the outside of the cell which is accessible to binding by proteins and other molecules.

The term "extracellular portion" or "exodomain" in the context of the present invention refers to a part of a molecule such as a protein that is facing the extracellular space of a cell and preferably is accessible from the outside of said cell, e.g., by binding molecules such as antibodies located outside the cell. Preferably, the term refers to one or more extracellular loops or domains or a fragment thereof.

The term "epitope" refers to a part or fragment of a molecule such as an antigen that is recognized by the immune system. For example, the epitope may be recognized by T cells, B cells or antibodies. An epitope of an antigen may include a continuous or discontinuous portion of the antigen and may be between about and about 100, such as between about 5 and about 50, more preferably between about 8 and about 30, most preferably between about 10 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope is between about 10 and about 25 amino acids in length. The term "epitope" includes T cell epitopes.

The term "T cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

In one embodiment, the target antigen is a tumor antigen and the vaccine antigen or a fragment thereof (e.g., an epitope) is derived from the tumor antigen. The tumor antigen may be a "standard" antigen, which is generally known to be expressed in various cancers. The tumor antigen may also be a "neo-antigen", which is specific to an individual's tumor and has not been previously recognized by the immune system. A neo-antigen or neo-epitope may result from one or more cancer-specific mutations in the genome of cancer cells resulting in amino acid changes. If the tumor antigen is a neo-antigen, the vaccine antigen preferably comprises an epitope or a fragment of said neo-antigen comprising one or more amino acid changes.

Cancer mutations vary with each individual. Thus, cancer mutations that encode novel epitopes (neo-epitopes) represent attractive targets in the development of vaccine compositions and immunotherapies. The efficacy of tumor immunotherapy relies on the selection of cancer-specific antigens and epitopes capable of inducing a potent immune response within a host. RNA can be used to deliver patient-specific tumor epitopes to a patient. Dendritic cells (DCs) residing in the spleen represent antigen-presenting cells of particular interest for RNA expression of immunogenic epitopes or antigens such as tumor epitopes.

The use of multiple epitopes has been shown to promote therapeutic efficacy in tumor vaccine compositions. Rapid sequencing of the tumor mutanome may provide multiple epitopes for individualized vaccines which can be encoded by RNA described herein, e.g., as a single polypeptide wherein the epitopes are optionally separated by linkers. In certain embodiments of the present disclosure, the RNA encodes at least one epitope, at least two epitopes, at least three epitopes, at least four epitopes, at least five epitopes, at least six epitopes, at least seven epitopes, at least eight epitopes, at least nine epitopes, or at least ten epitopes. Exemplary embodiments include RNA that encodes at least five epitopes (termed a "pentatope") and RNA that encodes at least ten epitopes (termed a "decatope").

According to the various aspects of the invention, the aim is preferably to provide an immune response against cancer cells expressing a tumor antigen and to treat a cancer disease involving cells expressing a tumor antigen. Preferably the invention involves the administration of antigen receptor-engineered immune effector cells such as T cells targeted against cancer cells expressing a tumor antigen.

The peptide and protein antigen can be 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids in length. In some embodiments, a peptide can be greater than 50 amino acids. In some embodiments, the peptide can be greater than 100 amino acids.

According to the invention, the vaccine antigen should be recognizable by an immune effector cell. Preferably, the antigen if recognized by an immune effector cell is able to induce in the presence of appropriate co-stimulatory signals, stimulation, priming and/or expansion of the immune effector cell carrying an antigen receptor recognizing the antigen. In the context of the embodiments of the present invention, the antigen is preferably present on the surface of a cell, preferably an antigen presenting cell. Recognition of the antigen on the surface of a diseased cell may result in an immune reaction against the antigen (or cell expressing the antigen).

In one embodiment of all aspects of the invention, an antigen is expressed in a diseased cell such as a cancer cell. In one embodiment, an antigen is expressed on the surface of a diseased cell such as a cancer cell. In one embodiment, an antigen receptor is a CAR which binds to an extracellular domain or to an epitope in an extracellular domain of an antigen. In one embodiment, a CAR binds to native epitopes of an antigen present on the surface of living cells. In one embodiment, binding of a CAR when expressed by T cells and/or present on T cells to an antigen present on cells such as antigen presenting cells results in stimulation, priming and/or expansion of said T cells. In one embodiment, binding of a CAR when expressed by T cells and/or present on T cells to an antigen present on diseased cells such as cancer cells results in cytolysis and/or apoptosis of the diseased cells, wherein said T cells preferably release cytotoxic factors, e.g. perforins and granzymes.

Immune Checkpoint Inhibitors

In certain embodiments, immune checkpoint inhibitors are used in combination with other therapeutic agents described herein.

As used herein, "immune checkpoint" refers to co-stimulatory and inhibitory signals that regulate the amplitude and quality of T cell receptor recognition of an antigen. In certain embodiments, the immune checkpoint is an inhibitory signal. In certain embodiments, the inhibitory signal is the interaction between PD-1 and PD-L1. In certain embodiments, the inhibitory signal is the interaction between CTLA-4 and CD80 or CD86 to displace CD28 binding. In certain embodiments the inhibitory signal is the interaction between LAG3 and MHC class II molecules. In certain embodiments, the inhibitory signal is the interaction between TIM3 and galectin 9.

As used herein, "immune checkpoint inhibitor" refers to a molecule that totally or partially reduces, inhibits, interferes with or modulates one or more checkpoint proteins. In certain embodiments, the immune checkpoint inhibitor prevents inhibitory signals associated with the immune checkpoint. In certain embodiments, the immune checkpoint inhibitor is an antibody, or fragment thereof that disrupts inhibitory signaling associated with the immune checkpoint. In certain embodiments, the immune checkpoint inhibitor is a small molecule that disrupts inhibitory signaling. In certain embodiments, the immune checkpoint inhibitor is an antibody, fragment thereof, or antibody mimic, that prevents the interaction between checkpoint blocker proteins, e.g., an antibody, or fragment thereof, that prevents the interaction between PD-1 and PD-L1. In certain embodiments, the immune checkpoint inhibitor is an antibody, or fragment thereof, that prevents the interaction between CTLA-4 and CD80 or CD86. In certain embodiments, the immune checkpoint inhibitor is an antibody, or fragment thereof, that prevents the interaction between LAG3 and its ligands, or TIM-3 and its ligands. The checkpoint inhibitor may also be in the form of the soluble form of the molecules (or variants thereof) themselves, e.g., a soluble PD-L1 or PD-L1 fusion.

The "Programmed Death-1 (PD-1)" receptor refers to an immuno-inhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1.

"Programmed Death Ligand-1 (PD-1)" is one of two cell surface glycoprotein ligands for PD-1 (the other being PD-L2) that downregulates T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1.

"Cytotoxic T Lymphocyte Associated Antigen-4 (CTLA-4)" is a T cell surface molecule and is a member of the immunoglobulin superfamily. This protein downregulates the immune system by binding to CD80 and CD86. The term "CTLA-4" as used herein includes human CTLA-4 (hCTLA-4), variants, isoforms, and species homologs of hCTLA-4, and analogs having at least one common epitope with hCTLA-4.

"Lymphocyte Activation Gene-3 (LAG3)" is an inhibitory receptor associated with inhibition of lymphocyte activity by binding to MHC class II molecules. This receptor enhances the function of Treg cells and inhibits CD8$^+$ effector T cell function. The term "LAG3" as used herein includes human LAG3 (hLAG3), variants, isoforms, and species homologs of hLAG3, and analogs having at least one common epitope.

"T Cell Membrane Protein-3 (TIM3)" is an inhibitory receptor involved in the inhibition of lymphocyte activity by inhibition of TH1 cell responses. Its ligand is galectin 9, which is upregulated in various types of cancers. The term "TIM3" as used herein includes human TIM3 (hTIM3), variants, isoforms, and species homologs of hTIM3, and analogs having at least one common epitope.

The "B7 family" refers to inhibitory ligands with undefined receptors. The B7 family encompasses B7-H3 and B7-H4, both upregulated on tumor cells and tumor infiltrating cells.

In certain embodiments, the immune checkpoint inhibitor suitable for use in the methods disclosed herein, is an antagonist of inhibitory signals, e.g., an antibody which targets, for example, PD-1, PD-L1, CTLA-4, LAG3, B7-H3, B7-H4, or TIM3. These ligands and receptors are reviewed in Pardoll, D., Nature. 12: 252-264, 2012.

In certain embodiments, the immune checkpoint inhibitor is an antibody or an antigen-binding portion thereof, that disrupts or inhibits signaling from an inhibitory immunoregulator. In certain embodiments, the immune checkpoint inhibitor is a small molecule that disrupts or inhibits signaling from an inhibitory immunoregulator.

In certain embodiments, the inhibitory immunoregulator is a component of the PD-1/PD-L1 signaling pathway. Accordingly, certain embodiments of the disclosure provide for administering to a subject an antibody or an antigen-binding portion thereof that disrupts the interaction between the PD-1 receptor and its ligand, PD-L1. Antibodies which bind to PD-1 and disrupt the interaction between the PD-1 and its ligand, PD-L1, are known in the art. In certain embodiments, the antibody or antigen-binding portion thereof binds specifically to PD-1. In certain embodiments, the antibody or antigen-binding portion thereof binds specifically to PD-L1 and inhibits its interaction with PD-1, thereby increasing immune activity.

In certain embodiments, the inhibitory immunoregulator is a component of the CTLA-4 signaling pathway. Accordingly, certain embodiments of the disclosure provide for administering to a subject an antibody or an antigen-binding portion thereof that targets CTLA-4 and disrupts its interaction with CD80 and CD86.

In certain embodiments, the inhibitory immunoregulator is a component of the LAG3 (lymphocyte activation gene 3) signaling pathway. Accordingly, certain embodiments of the disclosure provide for administering to a subject an antibody or an antigen-binding portion thereof that targets LAG3 and disrupts its interaction with MHC class II molecules.

In certain embodiments, the inhibitory immunoregulator is a component of the B7 family signaling pathway. In certain embodiments, the B7 family members are B7-H3 and B7-H4. Accordingly, certain embodiments of the disclosure provide for administering to a subject an antibody or an antigen-binding portion thereof that targets B7-H3 or H4.

The B7 family does not have any defined receptors but these ligands are upregulated on tumor cells or tumor-infiltrating cells. Preclinical mouse models have shown that blockade of these ligands can enhance anti-tumor immunity.

In certain embodiments, the inhibitory immunoregulator is a component of the TIM3 (T cell membrane protein 3) signaling pathway. Accordingly, certain embodiments of the disclosure provide for administering to a subject an antibody or an antigen-binding portion thereof that targets TIM3 and disrupts its interaction with galectin 9.

It will be understood by one of ordinary skill in the art that other immune checkpoint targets can also be targeted by antagonists or antibodies, provided that the targeting results in the stimulation of an immune response such as an anti-tumor immune response as reflected in, e.g., an increase in T cell proliferation, enhanced T cell activation, and/or increased cytokine production (e.g., IFN-γ, IL2).

RNA Targeting

It is particularly preferred according to the invention that the peptides, proteins or polypeptides described herein, in particular the IL2 variant polypeptides and/or vaccine antigens, are administered in the form of RNA encoding the peptides, proteins or polypeptides described herein. In one embodiment, different peptides, proteins or polypeptides described herein are encoded by different RNA molecules.

In one embodiment, the RNA is formulated in a delivery vehicle. In one embodiment, the delivery vehicle comprises particles. In one embodiment, the delivery vehicle comprises at least one lipid. In one embodiment, the at least one lipid comprises at least one cationic lipid. In one embodiment, the lipid forms a complex with and/or encapsulates the RNA. In one embodiment, the lipid is comprised in a vesicle encapsulating the RNA. In one embodiment, the RNA is formulated in liposomes.

According to the disclosure, after administration of the RNA described herein, at least a portion of the RNA is delivered to a target cell. In one embodiment, at least a portion of the RNA is delivered to the cytosol of the target cell. In one embodiment, the RNA is translated by the target cell to produce the encoded peptide or protein.

Some aspects of the disclosure involve the targeted delivery of the RNA disclosed herein (e.g., RNA encoding IL2 variant polypeptides and/or RNA encoding vaccine antigen).

In one embodiment, the disclosure involves targeting the lymphatic system, in particular secondary lymphoid organs, more specifically spleen. Targeting the lymphatic system, in particular secondary lymphoid organs, more specifically spleen is in particular preferred if the RNA administered is RNA encoding vaccine antigen.

In one embodiment, the target cell is a spleen cell. In one embodiment, the target cell is an antigen presenting cell such as a professional antigen presenting cell in the spleen. In one embodiment, the target cell is a dendritic cell in the spleen.

The "lymphatic system" is part of the circulatory system and an important part of the immune system, comprising a network of lymphatic vessels that carry lymph. The lymphatic system consists of lymphatic organs, a conducting network of lymphatic vessels, and the circulating lymph. The primary or central lymphoid organs generate lymphocytes from immature progenitor cells. The thymus and the bone marrow constitute the primary lymphoid organs. Secondary or peripheral lymphoid organs, which include lymph nodes and the spleen, maintain mature naïve lymphocytes and initiate an adaptive immune response.

RNA may be delivered to spleen by so-called lipoplex formulations, in which the RNA is bound to liposomes comprising a cationic lipid and optionally an additional or helper lipid to form injectable nanoparticle formulations. The liposomes may be obtained by injecting a solution of the lipids in ethanol into water or a suitable aqueous phase. RNA lipoplex particles may be prepared by mixing the liposomes with RNA. Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

In the context of the present disclosure, the term "RNA lipoplex particle" relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In one embodiment, a RNA lipoplex particle is a nanoparticle.

As used herein, a "cationic lipid" refers to a lipid having a net positive charge. Cationic lipids bind negatively charged RNA by electrostatic interaction to the lipid matrix. Generally, cationic lipids possess a lipophilic moiety, such as a sterol, an acyl or diacyl chain, and the head group of the lipid typically carries the positive charge. Examples of cationic lipids include, but are not limited to 1,2-di-O-octadecenyl-3-trimethylammonium propane (DOTMA), dimethyldioctadecylammonium (DDAB); 1,2-dioleoyl-3-trimethylammonium propane (DOTAP); 1,2-dioleoyl-3-di-methylammonium-propane (DODAP); 1,2-diacryloxy-3-di-methylammonium propanes; 1,2-dialkyloxy-3-dimethylammonium propanes; dioctadecyldimethyl ammonium chloride (DODAC), 2,3-di(tetradecoxy)propyl-(2-hydroxyethyl)-dimethylazanium (DMRIE), 1,2-dimyristoyl-sn-glycero-3-ethylphosphocholine (DMEPC), 1,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2(spermine carboxamide)ethyl]-N,N-dimethyl-l-propanamium trifluoroacetate (DOSPA). Preferred are DOTMA, DOTAP, DODAC, and DOSPA. In specific embodiments, the cationic lipid is DOTMA and/or DOTAP.

An additional lipid may be incorporated to adjust the overall positive to negative charge ratio and physical stability of the RNA lipoplex particles. In certain embodiments, the additional lipid is a neutral lipid. As used herein, a "neutral lipid" refers to a lipid having a net charge of zero. Examples of neutral lipids include, but are not limited to, 1,2-di-(9Z-octadecenoyl)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, cholesterol, and cerebroside. In specific embodiments, the additional lipid is DOPE, cholesterol and/or DOPC.

In certain embodiments, the RNA lipoplex particles include both a cationic lipid and an additional lipid. In an exemplary embodiment, the cationic lipid is DOTMA and the additional lipid is DOPE.

In some embodiments, the molar ratio of the at least one cationic lipid to the at least one additional lipid is from about 10:0 to about 1:9, about 4:1 to about 1:2, or about 3:1 to about 1:1. In specific embodiments, the molar ratio may be about 3:1, about 2.75:1, about 2.5:1, about 2.25:1, about 2:1, about 1.75:1, about 1.5:1, about 1.25:1, or about 1:1. In an exemplary embodiment, the molar ratio of the at least one cationic lipid to the at least one additional lipid is about 2:1.

RNA lipoplex particles described herein have an average diameter that in one embodiment ranges from about 200 nm to about 1000 nm, from about 200 nm to about 800 nm, from about 250 to about 700 nm, from about 400 to about 600 nm, from about 300 nm to about 500 nm, or from about 350 nm to about 400 nm. In specific embodiments, the RNA lipoplex particles have an average diameter of about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 700 nm, about 725 nm, about 750 nm, about 775 nm, about 800 nm, about 825 nm, about 850 nm, about 875 nm, about 900 nm, about 925 nm, about 950 nm, about 975 nm, or about 1000 nm. In an embodiment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm.

The electric charge of the RNA lipoplex particles of the present disclosure is the sum of the electric charges present in the at least one cationic lipid and the electric charges present in the RNA. The charge ratio is the ratio of the positive charges present in the at least one cationic lipid to the negative charges present in the RNA. The charge ratio of the positive charges present in the at least one cationic lipid to the negative charges present in the RNA is calculated by the following equation: charge ratio=[(cationic lipid concentration (mol))*(the total number of positive charges in the cationic lipid)]/[(RNA concentration (mol))*(the total number of negative charges in RNA)].

The spleen targeting RNA lipoplex particles described herein at physiological pH preferably have a net negative charge such as a charge ratio of positive charges to negative charges from about 1.9:2 to about 1:2. In specific embodiments, the charge ratio of positive charges to negative charges in the RNA lipoplex particles at physiological pH is about 1.9:2.0, about 1.8:2.0, about 1.7:2.0, about 1.6:2.0, about 1.5:2.0, about 1.4:2.0, about 1.3:2.0, about 1.2:2.0, about 1.1:2.0, or about 1:2.0.

RNA delivery systems have an inherent preference to the liver. This pertains to lipid-based particles, cationic and neutral nanoparticles, in particular lipid nanoparticles such as liposomes, nanomicelles and lipophilic ligands in bioconjugates. Liver accumulation is caused by the discontinuous nature of the hepatic vasculature or the lipid metabolism (liposomes and lipid or cholesterol conjugates).

In one embodiment of the targeted delivery of an IL2 variant polypeptide described herein, the target organ is liver and the target tissue is liver tissue. The delivery to such target tissue is preferred, in particular, if presence of the IL2 variant polypeptide in this organ or tissue is desired and/or if it is desired to express large amounts of the IL2 variant polypeptide and/or if systemic presence of the IL2 variant polypeptide, in particular in significant amounts, is desired or required.

In one embodiment, RNA encoding an IL2 variant polypeptide is administered in a formulation for targeting liver. Such formulations are described herein above.

For in vim delivery of RNA to the liver, a drug delivery system may be used to transport the RNA into the liver by preventing its degradation. For example, polyplex nanomicelles consisting of a poly(ethylene glycol) (PEG)-coated surface and an mRNA-containing core is a useful system because the nanomicelles provide excellent in vivo stability of the RNA, under physiological conditions. Furthermore, the stealth property provided by the polyplex nanomicelle surface, composed of dense PEG palisades, effectively evades host immune defenses.

Pharmaceutical Compositions

The peptides, proteins, polypeptides, RNA, RNA particles, immune effector cells and further agents, e.g., immune checkpoint inhibitors, described herein may be administered in pharmaceutical compositions or medicaments for therapeutic or prophylactic treatments and may be administered in the form of any suitable pharmaceutical composition which may comprise a pharmaceutically acceptable carrier and may optionally comprise one or more adjuvants, stabilizers etc. In one embodiment, the pharmaceutical composition is for therapeutic or prophylactic treatments, e.g., for use in treating or preventing a disease involving an antigen such as a cancer disease such as those described herein.

The term "pharmaceutical composition" relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation. In the context of the present disclosure, the pharmaceutical composition comprises peptides, proteins, polypeptides, RNA, RNA particles, immune effector cells and/or further agents as described herein.

The pharmaceutical compositions of the present disclosure may comprise one or more adjuvants or may be administered with one or more adjuvants. The term 'adjuvant' relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cytokines, such as monokines, lymphokines, interleukins, chemokines. The cytokines may be IL1, IL2, IL3, IL4, IL5, IL6, IL7, IL8, IL9, IL10, IL12, IFNα, IFNγ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys.

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" or "therapeutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

In one embodiment, pharmaceutical compositions described herein may be administered intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical compositions is formulated for systemic administration. In another preferred embodiment, the systemic administration is by intravenous administration. In one embodiment of all aspects of the invention, RNA encoding an IL2 variant polypeptide described herein and optionally RNA encoding an antigen is administered systemically.

The term "co-administering" as used herein means a process whereby different compounds or compositions (e.g., immune effector cells, RNA encoding an IL2 variant polypeptide, and optionally RNA encoding a vaccine antigen) are administered to the same patient. The different compounds or compositions may be administered simultaneously, at essentially the same time, or sequentially.

Treatments

The agents, compositions and methods described herein can be used to treat a subject with a disease, e.g., a disease characterized by the presence of diseased cells expressing an antigen. Particularly preferred diseases are cancer diseases. For example, if the antigen is derived from a virus, the agents, compositions and methods may be useful in the treatment of a viral disease caused by said virus. If the antigen is a tumor antigen, the agents, compositions and methods may be useful in the treatment of a cancer disease wherein cancer cells express said tumor antigen.

The agents, compositions and methods described herein may be used in the therapeutic or prophylactic treatment of various diseases, wherein provision of immune effector cells and/or activity of immune effector cells as described herein is beneficial for a patient such as cancer and infectious diseases In one embodiment, the agents, compositions and methods described herein are useful in a prophylactic and/or therapeutic treatment of a disease involving an antigen.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

In one embodiment of the disclosure, the aim is to provide an immune response against diseased cells expressing an antigen such as cancer cells expressing a tumor antigen, and to treat a disease such as a cancer disease involving cells expressing an antigen such as a tumor antigen.

As used herein, "immune response" refers to an integrated bodily response to an antigen or a cell expressing an antigen and refers to a cellular immune response and/or a humoral immune response.

"Cell-mediated immunity", "cellular immunity", "cellular immune response", or similar terms are meant to include a cellular response directed to cells characterized by expression of an antigen, in particular characterized by presentation of an antigen with class I or class II MHC. The cellular response relates to cells called T cells or T lymphocytes which act as either "helpers" or "killers". The helper T cells (also termed CD4+ T cells) play a central role by regulating the immune response and the killer cells (also termed cytotoxic T cells, cytolytic T cells, CD8+ T cells or CTLs) kill diseased cells such as cancer cells, preventing the production of more diseased cells.

The present disclosure contemplates an immune response that may be protective, preventive, prophylactic and/or therapeutic. As used herein, "induces [or inducing] an immune response" may indicate that no immune response against a particular antigen was present before induction or it may indicate that there was a basal level of immune response against a particular antigen before induction, which was enhanced after induction. Therefore, "induces [or inducing] an immune response" includes "enhances [or enhancing] an immune response".

The term "immunotherapy" relates to the treatment of a disease or condition by inducing, or enhancing an immune response. The term "immunotherapy" includes antigen immunization or antigen vaccination.

The terms "immunization" or "vaccination" describe the process of administering an antigen to an individual with the purpose of inducing an immune response, for example, for therapeutic or prophylactic reasons.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells. In one embodiment, the macrophages are splenic macrophages.

The term "dendritic cell" (DC) refers to another subtype of phagocytic cells belonging to the class of antigen presenting cells. In one embodiment, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. In one embodiment, the dendritic cells are splenic dendritic cells.

The term "antigen presenting cell" (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, such as antigen presenting cells to specific T cells.

The term "disease involving an antigen" refers to any disease which implicates an antigen, e.g. a disease which is characterized by the presence of an antigen. The disease involving an antigen can be an infectious disease, or a cancer disease or simply cancer. As mentioned above, the antigen may be a disease-associated antigen, such as a tumor-associated antigen, a viral antigen, or a bacterial antigen. In one embodiment, a disease involving an antigen is a disease involving cells expressing an antigen, preferably on the cell surface.

The term "infectious disease" refers to any disease which can be transmitted from individual to individual or from organism to organism, and is caused by amicrobial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the disclosure also comprises cancer metastases.

Combination strategies in cancer treatment may be desirable due to a resulting synergistic effect, which may be considerably stronger than the impact of a monotherapeutic approach. In one embodiment, the pharmaceutical composition is administered with an immunotherapeutic agent. As used herein "immunotherapeutic agent" relates to any agent that may be involved in activating a specific immune response and/or immune effector function(s). The present disclosure contemplates the use of an antibody as an immunotherapeutic agent. Without wishing to be bound by theory, antibodies are capable of achieving a therapeutic effect against cancer cells through various mechanisms, including inducing apoptosis, block components of signal transduction pathways or inhibiting proliferation of tumor cells. In certain embodiments, the antibody is a monoclonal antibody. A monoclonal antibody may induce cell death via antibody-dependent cell mediated cytotoxicity (ADCC), or bind complement proteins, leading to direct cell toxicity, known as complement dependent cytotoxicity (CDC). Non-limiting examples of anti-cancer antibodies and potential antibody targets (in brackets) which may be used in combination with the present disclosure include: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Atezolizumab (PD-L1), Bavituximab (phosphatidylserine), Bectumomab (CD22), Belimumab (BAFF), Bevacizumab (VEGF-A), Bivatuzumab mertansine (CD44 v6), Blinatumomab (CD 19), Brentuximab vedotin (CD30 TNFRSF8), Cantuzumab mertansin (mucin CanAg), Cantuzumab ravtansine (MUC1), Capromab pendetide (prostatic carcinoma cells), Cardumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin αvβ3), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-β), Galiximab (CD80), Ganitumab (IGF-1), Gemtuzumab ozogamicin (CD33), Gevokizumab (ILIβ), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD 152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL5), Milatuzumab (CD74), Mitumomab (GD3 ganglioside), Mogamuizumab (CCR4), Moxetumomab pasudotox (CD22), Nacolomab tafenatox (C242 antigen), Naptumomab estatenatox (5T4), Namatumab (RON), Necitumumab (EGFR), Nimotuzumab (EGFR), Nivolumab (IgG4), Ofatumumab (CD20), Olaratumab (PDGF-R a), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzuma (HER2/neu), Pintumomab (adenocarcinoma antigen), Pritumumab (vimentin), Racotumomab (N-glycolyl-neuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL6), Tabalumab (BAFF), Tacatuzumab tetraxetan (alpha-fetoprotein), Taplitumomab paptox (CD 19), Tenatumomab (tenascin C), Teprotumumab (CD221), Ticilimumab (CTLA-4), Tigatuzumab (TRAIL-R2), TNX-650 (IL13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1 BB), Volociximab (integrin α5β1), Votumumab (tumor antigen CTAA 16.88), Zalutumumab (EGFR), and Zanokimumab (CD4).

Citation of documents and studies referenced herein is not intended as an admission that any of the foregoing is pertinent prior art. All statements as to the contents of these documents are based on the information available to the The four different hIL2 variants comprised the following amino acid substitutions:

hIL2_A3: K35E, K43E and E61K
hIL2_A4: K43E and E61K
hIL2_A5: E61K
hIL2_A8: K43E

The four different hIL2RA mutants comprised the following substitutions:

hIL2RA_mut1: E29K and K38E
hIL2RA_mut2: K38E
hIL2RA_mut3: E29K
hIL2RA_mut4: E1K, E29K and K38E Based on this initial design four beneficial combinations of matching mutated hIL2 and hIL2RA were predicted (see Table 1).

TABLE 1

Predictions of matching hIL2RA mutant and hAIb-hIL2 variant pairings (marked with X) based on the positions of the amino acid substitutions within the hIL2 and hIL2RA sequence.

| | | hIL2RA mutant | | | |
| --- | --- | --- | --- | --- | --- |
| | | hIL2RA_mut1 (E29K,K38E) | hIL2RA_mut2 (K38E) | hIL2RA_mut3 (E29K) | hIL2RA_mut4 (E1K,E29K,K38E) |
| hAIb-hIL2 variant | hAIb-hIL2_A3 (K35E,K43E,E61K) | | | | X |
| | hAIb-hIL2_A4 (K43E,E61K) | X | | | |
| | hAIb-hIL2_A5 (E61K) | | X | | |
| | hAIb-hIL2_A8 (K43E) | | | X | | applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Construct Design

In order to design reciprocal pairs of human IL2 (hIL2) and interleukin 2 receptor subunit alpha (hIL2RA, CD25), various amino acid substitutions were implemented at the hIL2:hIL2RA binding interface. In more detail, guided by the crystal structure of the hIL2 high-affinity receptor complex as published by Stauber et al. (Stauber, D. et al. PNAS Feb. 21, 2006103 (8) 2788-2793) three pairs of basic and acidic amino acid residues were identified that are part of the ionic interactions that drive hIL2:hIL2RA binding. The respective residues were exchanged in a reciprocal fashion, mutating basic amino acids to acidic amino acids and vice versa. For both hIL2 and the corresponding hIL2RA up to three amino acid positions were mutated resulting in four hIL2 variants with predicted altered hIL2RA binding and four hIL2RA mutants with predicted altered hIL2 binding.

Example 2: mRNA Production

Cytokine encoding mRNAs for in vitro transcription were based on the pST1-T7-AGA-dEarl-hAg-MCS-FI-A30LA70 plasmid-backbone and derivative DNA-constructs. These plasmid constructs contain a 5' UTR (untranslated region, a derivative of the 5'-UTR of Homo sapiens hemoglobin subunit alpha 1 (hAg)), a 3' FI element (where F is a 136 nucleotide long 3'-UTR fragment of amino-terminal enhancer of split mRNA and I is a 142 nucleotide long fragment of mitochondrially encoded 12S RNA both identified in Homo sapiens; WO 2017/060314) and a poly(A) tail of 100 nucleotides, with a linker after 70 nucleotides.

Cytokine and serum albumin (hAlb) encoding sequences originate from Homo sapiens and no changes in the resulting amino acid sequences were introduced except for the intended mutations in the hIL2 variants described above (hIL2: NP_000577.2; NCBI protein resource[AM1]). For cytokine constructs the hIL2 variant was added to the C-terminus of hAlb and encoded proteins were equipped with an N-terminal signal peptide (SP) that is the native SP of the respective protein. In case of fusion proteins, only the SP of the N-terminal moiety was maintained, for further moieties only the mature portion (protein without SP) was encoded. A stop-codon was introduced for the most C-terminal moiety only. Different protein moieties in the cytokine and hAlb fusion constructs were separated by a 30-nucleotide long linker sequence encoding for glycine and serine residues.

The IL2RA encoding sequence originates from Homo sapiens and no changes in the resulting amino acid sequences were introduced except for the intended mutations to alter hIL2 binding in the reciprocal hIL2RA mutants described above (hIL2RA: NP_000408.1; NCBI protein resource). Encoded proteins were equipped with an N-terminal signal peptide (SP) that is the native SP of hIL2RA.

mRNA was generated by in vitro transcription as described by Kreiter et al. (Kreiter, S. et al. Cancer Immunol. Immunother. 56, 1577-87 (2007)) with substitution of the normal nucleoside uridine by 1-methyl-pseudouridine. Resulting mRNAs were equipped with a Cap1-structure and double-stranded (dsRNA) molecules were depleted. Purified mRNA was eluted in H$_2$O and stored at −80° C. until further use. In vitro transcription of all described mRNA constructs was carried out at BioNTech RNA Pharmaceuticals GmbH. A list of all constructs used in subsequent experiments is shown in Table 2.

TABLE 2

| Amino acid sequences of mRNA encoded and expressed proteins. | |
| --- | --- |
| hAIb (SEQ ID NO: 3) | MKWVTFISLLFLFSSAYSRGVFRRDAHKSEVAHRFKDLGEENFKALVLIAFAQYLQQCPFE DHVKLVNEVTEFAKTCVADESAENCDKSLHTLFGDKLCTVATLRETYGEMADCCAKQEPE RNECFLQHKDDNPNLPRLVRPEVDVMCTAFHDNEETFLKKYLYEIARRHPYFYAPELLFFA KRYKAAFTECCQAADKAACLLPKLDELRDEGKASSAKQRLKCASLQKFGERAFKAWAVA RLSQRFPKAEFAEVSKLVTDLTKVHTECCHGDLLECADDRADLAKYICENQDSISSKLKEC CEKPLLEKSHCIAEVENDEMPADLPSLAADFVESKDVCKNYAEAKDVFLGMFLYEYARRH PDYSVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSVVLNQ LCVLHEKTPVSDRVTKCCTESLVNRRPCFSALEVDETYVPKEFNAETFTFHADICTLSEKE RQIKKQTALVELVKHKPKATKEQLKAVMDDFAAFVEKCCKADDKETCFAEEGKKLVAASQ AALGL |
| hAIb-hIL2 (SEQ ID NO: 9) | MKWVTFISLLFLFSSAYSRGVFRRDAHKSEVAHRFKDLGEENFKALVLIAFAQYLQQCPFE DHVKLVNEVTEFAKTCVADESAENCDKSLHTLFGDKLCTVATLRETYGEMADCCAKQEPE RNECFLQHKDDNPNLPRLVRPEVDVMCTAFHDNEETFLKKYLYEIARRHPYFYAPELLFFA KRYKAAFTECCQAADKAACLLPKLDELRDEGKASSAKQRLKCASLQKFGERAFKAWAVA RLSQRFPKAEFAEVSKLVTDLTKVHTECCHGDLLECADDRADLAKYICENQDSISSKLKEC CEKPLLEKSHCIAEVENDEMPADLPSLAADFVESKDVCKNYAEAKDVFLGMFLYEYARRH PDYSVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSVVLNQ LCVLHEKTPVSDRVTKCCTESLVNRRPCFSALEVDETYVPKEFNAETFTFHADICTLSEKE RQIKKQTALVELVKHKPKATKEQLKAVMDDFAAFVEKCCKADDKETCFAEEGKKLVAASQ AALGLGGSGGGGSGGAPTSSSTKKTQLQLEHLLLDLQMILNGINNYKNPKLTRMLTFKFY MPKKATELKHLQCLEEELKPLEEVLNLAQSKNFHLRPRDLISNINVIVLELKGSETTFMCEY ADETATIVEFLNRWITFCQSIISTLT |
| hAIb-hIL2_A3 (SEQ ID NO: 10) | MKWVTFISLLFLFSSAYSRGVFRRDAHKSEVAHRFKDLGEENFKALVLIAFAQYLQQCPFE DHVKLVNEVTEFAKTCVADESAENCDKSLHTLFGDKLCTVATLRETYGEMADCCAKQEPE RNECFLQHKDDNPNLPRLVRPEVDVMCTAFHDNEETFLKKYLYEIARRHPYFYAPELLFFA KRYKAAFTECCQAADKAACLLPKLDELRDEGKASSAKQRLKCASLQKFGERAFKAWAVA RLSQRFPKAEFAEVSKLVTDLTKVHTECCHGDLLECADDRADLAKYICENQDSISSKLKEC CEKPLLEKSHCIAEVENDEMPADLPSLAADFVESKDVCKNYAEAKDVFLGMFLYEYARRH PDYSVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSVVLNQ LCVLHEKTPVSDRVTKCCTESLVNRRPCFSALEVDETYVPKEFNAETFTFHADICTLSEKE RQIKKQTALVELVKHKPKATKEQLKAVMDDFAAFVEKCCKADDKETCFAEEGKKLVAASQ AALGLGGSGGGGSGGAPTSSSTKKTQLQLEHLLLDLQMILNGINNYKNPELTRMLTFEFY MPKKATELKHLQCLEKELKPLEEVLNLAQSKNFHLRPRDLISNINVIVLELKGSETTFMCEY ADETATIVEFLNRWITFCQSIISILT |
| hAIb-hIL2_A4 (SEQ ID NO: 11) | MKWVTFISLLFLFSSAYSRGVFRRDAHKSEVAHRFKDLGEENFKALVLIAFAQYLQQCPFE DHVKLVNEVTEFAKTCVADESAENCDKSLHTLFGDKLCTVATLRETYGEMADCCAKQEPE RNECFLQHKDDNPNLPRLVRPEVDVMCTAFHDNEETFLKKYLYEIARRHPYFYAPELLFFA KRYKAAFTECCQAADKAACLLPKLDELRDEGKASSAKQRLKCASLQKFGERAFKAWAVA RLSQRFPKAEFAEVSKLVTDLTKVHTECCHGDLLECADDRADLAKYICENQDSISSKLKEC CEKPLLEKSHCIAEVENDEMPADLPSLAADFVESKDVCKNYAEAKDVFLGMFLYEYARRH PDYSVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSVVLNQ LCVLHEKTPVSDRVTKCCTESLVNRRPCFSALEVDETYVPKEFNAETFTFHADICTLSEKE RQIKKQTALVELVKHKPKATKEQLKAVMDDFAAFVEKCCKADDKETCFAEEGKKLVAASQ AALGLGGSGGGGSGGAPTSSSTKKTQLQLEHLLLDLQMILNGINNYKNPKLTRMLTFEFY MPKKATELKHLQCLEKELKPLEEVLNLAQSKNFHLRPRDLISNINVIVLELKGSETTFMCEY ADETATIVEFLNRWITFCQSIISTLT |
| hAIb-hIL2_A5 (SEQ ID NO: 12) | MKWVTFISLLFLFSSAYSRGVFRRDAHKSEVAHRFKDLGEENFKALVLIAFAQYLQQCPFE DHVKLVNEVTEFAKTCVADESAENCDKSLHTLFGDKLCTVATLRETYGEMADCCAKQEPE RNECFLQHKDDNPNLPRLVRPEVDVMCTAFHDNEETFLKKYLYEIARRHPYFYAPELLFFA KRYKAAFTECCQAADKAACLLPKLDELRDEGKASSAKQRLKCASLQKFGERAFKAWAVA RLSQRFPKAEFAEVSKLVTDLTKVHTECCHGDLLECADDRADLAKYICENQDSISSKLKEC CEKPLLEKSHCIAEVENDEMPADLPSLAADFVESKDVCKNYAEAKDVFLGMFLYEYARRH PDYSVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSVVLNQ LCVLHEKTPVSDRVTKCCTESLVNRRPCFSALEVDETYVPKEFNAETFTFHADICTLSEKE RQIKKQTALVELVKHKPKATKEQLKAVMDDFAAFVEKCCKADDKETCFAEEGKKLVAASQ AALGLGGSGGGGSGGAPTSSSTKKTQLQLEHLLLDLQMILNGINNYKNPKLTRMLTFKFY MPKKATELKHLQCLEKELKPLEEVLNLAQSKNFHLRPRDLISNINVIVLELKGSETTFMCEY ADETATIVEFLNRWITFCQSIISTLT |

TABLE 2-continued

Amino acid sequences of mRNA encoded and expressed proteins.

hAlb-hIL2_A8
(SEQ ID NO:
13)
MKWVTFISLLFLFSSAYSRGVFRRDAHKSEVAHRFKDLGEENFKALVLIAFAQYLQQCPFE
DHVKLVNEVTEFAKTCVADESAENCDKSLHTLFGDKLCTVATLRETYGEMADCCAKQEPE
RNECFLQHKDDNPNLPRLVRPEVDVMCTAPHDNEETFLKKYLYEIARRHPYFYAPELLFFA
KRYKAAFTECCQAADKAACLLPKLDELRDEGKASSAKQRLKCASLQKFGERAFKAWAVA
RLSQRFPKAEFAEVSKLVTDLTKVHTECCHGDLLECADDRADLAKYICENQDSISSKLKEC
CEKPLLEKSHCIAEVENDEMPADLPSLAADFVESKDVCKNYAEAKDVFLGMFLYEYARRH
PDYSVVLLLRLAKTYETTLEKCCAAADPHECYAKVFDEFKPLVEEPQNLIKQNCELFEQLG
EYKFQNALLVRYTKKVPQVSTPTLVEVSRNLGKVGSKCCKHPEAKRMPCAEDYLSVVLNQ
LCVLHEKTPVSDRVTKCCTESLVNRRPCFSALEVDETYVPKEFNAETFTFHADICTLSEKE
RQIKKQTALVELVKHKPKATKEQLKAVMDDFAAFVEKCCMDDKETCFAEEGKKLVAASQ
AALGLGGSGGGGSGGAPTSSSTKKTQLQLEHLLLDLQMILNGINNYKNPKLTRMLTFEFY
MPKKATELKHLQCLEEELKPLEEVLNLAQSKNFHLRPRDLISNINVIVLELKGSETTFMCEY
ADETATIVEFLNRWITFCQSIISTLT hIL2RA
(SEQ ID NO:
4)
MDSYLLMWGLLTFIMVPGCQAELCDDDPPEIPHATFMMAYKEGTMLNCECKRGFRRIKS
GSLYMLCTGNSSHSSWDNQCQCTSSATRNTTKQVTPQPEEQKERKTTEMQSPMQPVDQ
ASLPGHCREPPPWENEATERIYHFVVGQMVYYQCVQGYRALHRGPAESVCKMTHGKTR
WTQPQLICTGEMETSQFPGEEKPQASPEGRPESETSCLVTTTDFQIQTEMAATMETSIFTT
EYQVAVAGCVFLLISVLLLSGLTWQRRQRKSRRTI hIL2RA_mut1
(SEQ ID NO:
14)
MDSYLLMWGLLTFIMVPGCQAELCDDDPPEIPHATFKAMAYKEGTMLNCKCKRGFRRIES
GSLYMLCTGNSSHSSWDNQCQCTSSATRNTTKQVTPQPEEQKERKTTEMQSPMQPVDQ
ASLPGHCREPPPWENEATERIYHFVVGQMVYYQCVQGYRALHRGPAESVCKMTHGKTR
WTQPQLICTGEMETSQFPGEEKPQASPEGRPESETSCLVTTTDFQIQTEMAATMETSIFTT
EYQVAVAGCVFLLISVLLLSGLTWQRRQRKSRRTI hIL2RA_mut2
(SEQ ID NO:
15)
MDSYLLMWGLLTFIMVPGCQAELCDDDPPEIPHATFKAMAYKEGTMLNCECKRGFRRIES
GSLYMLCTGNSSHSSWDNQCQCTSSATRNTTKQVTPQPEEQKERKTTEMQSPMQPVDQ
ASLPGHCREPPPWENEATERIYHFVVGQMVYYQCVQGYRALHRGPAESVCKMTHGKTR
WTQPQLICTGEMETSQFPGEEKPQASPEGRPESETSCLVTTTDFQIQTEMAATMETSIFTT
EYQVAVAGCVFLLISVLLLSGLTWQRRQRKSRRTI hIL2RA_mut3
(SEQ ID NO:
16)
MDSYLLMWGLLTFIMVPGCQAELCDDDPPEIPHATFKAMAYKEGTMLNCKCKRGFRRIKS
GSLYMLCTGNSSHSSWDNQCQCTSSATRNTTKQVTPQPEEQKERKTTEMQSPMQPVDQ
ASLPGHCREPPPWENEATERIYHFVVGQMVYYQCVQGYRALHRGPAESVCKMTHGKTR
WTQPQLICTGEMETSQFPGEEKPQASPEGRPESETSCLVTTTDFQIQTEMAATMETSIFTT
EYQVAVAGCVFLLISVLLLSGLTWQRRQRKSRRTI hIL2RA_mut4
(SEQ ID NO:
17)
MDSYLLMWGLLTFIMVPGCQAKLCDDDPPEIPHATFKAMAYKEGTMLNCKCKRGFRRIES
GSLYMLCTGNSSHSSWDNQCQCTSSATRNTTKQVTPQPEEQKERKTTEMQSPMQPVDQ
ASLPGHCREPPPWENEATERIYHFVVGQMVYYQCVQGYRALHRGPAESVCKMTHGKTR
WTQPQLICTGEMETSQFPGEEKPQASPEGRPESETSCLVTTTDFQIQTEMAATMETSIFTT
EYQVAVAGCVFLLISVLLLSGLTWQRRQRKSRRTI

Example 3: In Vitro Expression of RNA-Encoded hAlb-hIL2 Variants

Figure 1:
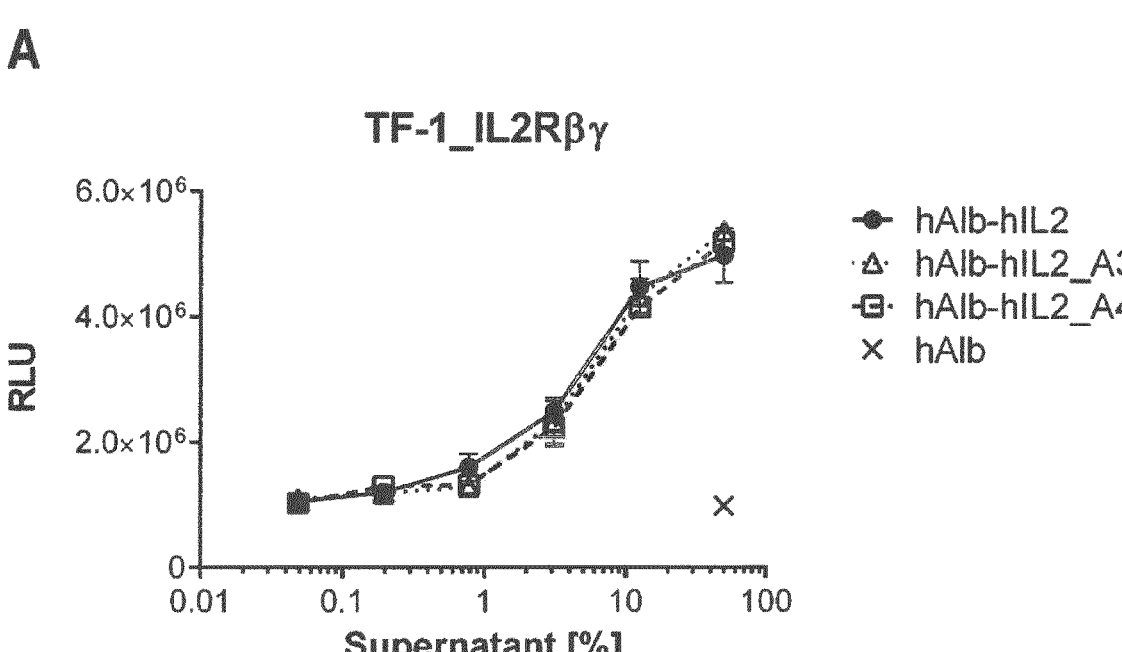
FIG. 1: In vitro expression and IL2Rβγ binding of RNA-encoded hAlb-hIL2 variants. $1.2 \times 10^6$ HEK293T/17 cells were seeded in 6-well plates and after reaching approx. 80% confluency lipofected with 3 μg mRNA (400 ng mRNA complexed per μL Lipofectamine MessengerMAX) in a total volume of 3.25 mL DMEM+10% FBS. After 20 h incubation at 37° C., 7.5% $CO_2$, supernatants were collected and serial dilutions thereof incubated with intermediate-affinity IL2 receptor (IL2Rβγ) expressing human cell line TF-1_IL2Rβγ. Proliferation responses were measured after three days by quantitating viable cells via ATP amount using the CellTiter-Glo®2.0 Assay. Data shown are mean±standard deviation (SD) of n=2 technical replicates. RLU=relative luminescence units.
Figure 1:
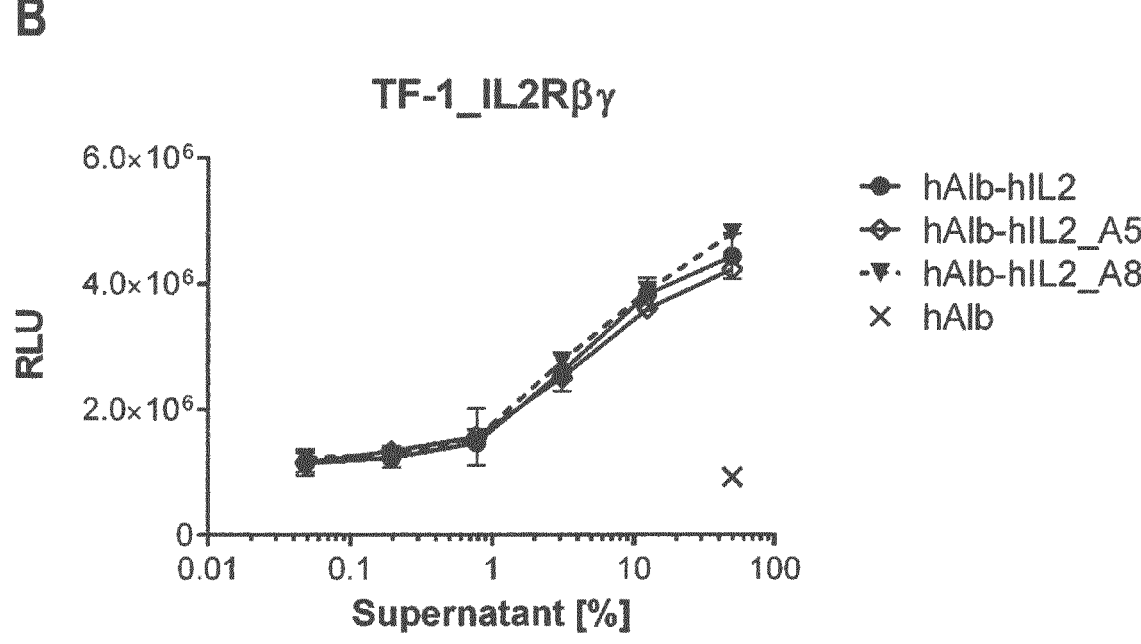

In vitro expression of the generated hAlb-hIL2 variant-encoding mRNAs was analyzed by lipofection of the mRNA into HEK293T/17 cells and subsequent analysis of the CD25 independent activation of IL2Rβγ-expressing reporter cells by hAlb-hIL2 variant containing supernatants (FIG. 1 A, B). One day prior to lipofection, $1.2 \times 10^6$ HEK293T/17 cells were seeded in 3 mL DMEM (Life Technologies GmbH, cat. no. 31966-021)+10% fetal bovine serum (FBS, Biochrom GmbH, cat. no. S0115) in 6-well plates. For lipofection, 3 µg IVT-mRNA was formulated under sterile and RNase-free conditions using 400 ng mRNA per µL Lipofectamine MessengerMax (Thermo Fisher Scientific, cat. No. LMRNA015) and applied per 10 $cm^2$ culture dish to the HEK293T/17 cells at approximately 80% confluence. After 20 h of expression, supernatants were collected under sterile conditions and stored at −20° C. until further use. The CD25-independent bioactivity of the hAlb-hIL2 variants was assessed by measuring specific proliferation responses of intermediate-affinity IL2 receptor (IL2Rβγ) expressing TF-1_IL2Rβγ cells. This cell line was generated from TF-1 cells (ATCC CRL-2003), a human erythroleukemic cell line naturally expressing the IL2R common γ-chain, by transduction with a retroviral vector encoding for the sequence of the human IL2Rβ chain (Gene ID: 3560) analogous to Famer et al. (Famer, N. L. et al. Blood 86, 4568-4578 (1995)). In short, TF-1_IL2Rβγ cells were washed two times with D-PBS and re-suspended in RPMI 1640 (+GlutaMAX, Life Technologies GmbH, cat. no. 61870-010) supplemented with 10% fetal bovine serum (FBS; Biochrom GmbH, cat. no. S0115) and 1 mM sodium pyruvate (Life Technologies GmbH, cat. no. 11360-039). A total of 5,000 cells/well were seeded in white 96-well flat-bottom plates (Fisher Scientific GmbH, cat. no. 10072151) and were incubated with four-fold serial dilutions of hAlb-hIL2 variant-containing supernatants. After three days of culture proliferation was measured by quantitating viable cells via ATP amount using the CellTiter-Glo® 2.0 Assay (Promega, cat. no. G9242). Luminescence was recorded on a Tecan Infinite® F200 PRO reader (Tecan Deutschland GmbH) and dose-response curves were plotted in GraphPad Prism version 6.04 (GraphPad Software, Inc.).

Wild-type hAlb-hIL2 as well as all hAlb-hIL2 variants with reduced CD25 binding affinity (i.e. hAlb-hIL2_A3, hAlb-hIL2_A4, hAlb-hIL2_A5 and hAlb-hIL2_A8) performed on par in inducing CD25-independent proliferation of IL2Rβγ-expressing TF-1_IL2Rβγ cells with nearly superimposable dose-response curves (FIG. 1 A, B). This is also reflected in the calculated $EC_{50}$ values, ranging from 4.62%-supernatant for hAlb-hIL2_A5 to 6.82%-supernatant for hAlb-hIL2_A4 (Table 3). In sum this indicates that mRNA encoding hAlb-hIL2 as well as hAlb-IL2 variants is translated into comparable amounts of functional cytokine.

TABLE 3

EC$_{50}$ values [%-supernatant] of the hAlb-hIL2 variants in intermediate-affinity IL2 receptor (IL2R$\beta\gamma$)-dependent cell culture derived from human TF-1_IL2R$\beta\gamma$ proliferation dose-responses.

| hAlb-hIL2 variant | EC$_{50}$ [%-supernatant] |
|---|---|
| hAlb-hIL2 | 4.65 |
| hAlb-hIL2_A3 | 6.44 |
| hAlb-hIL2_A4 | 6.82 |
| hAlb-hIL2_A5 | 4.62 |
| hAlb-hIL2_A8 | 5.16 |

Example 4: In Vitro Expression of RNA-Encoded hIL2RA (CD25) Mutants in Human Primary CD8$^+$ T Cells In order to test the expression of hIL2RA mutants in human primary CD8$^+$ T cells, CD8$^+$ T cells were isolated from PBMCs by magnetic-activated cell sorting (MACS) technology using anti-CD8 MicroBeads (Miltenyi, cat. no. 130-045-201), according to the manufacturer's instructions. About 10×10$^6$ CD8$^+$ T cells were electroporated with 15 µg of in vitro transcribed (IVT)-mRNA encoding the hIL2RA (CD25) mutants in 250 µL X-Vivo15 (Biozym Scientific GmbH, cat. no. 881026) in a 4-mm electroporation cuvette (VWR International GmbH, cat. no. 732-0023) using the BTX ECM® 830 Electroporation System device (BTX; 500 V, 1×3 ms pulse). Immediately after electroporation, cells were transferred into fresh Iscove's Modified Dulbecco's Medium (IMDM; Life Technologies GmbH, cat. no. 12440-053) supplemented with 5% human plasma-derived AB serum (One Lambda, cat. no. A25761) and rested at 37° C., 5% CO$_2$ for approximately 24 hours. The next day, the CD8$^+$ T cells were harvested and the cell surface expression of hIL2RA (CD25) mutants was checked by flow cytometry. CD8$^+$ T cells were stained with PerCP-Cy™ 5.5 Mouse Anti-Human CD25 antibody (Becton Dickinson GmbH, cat. no. 560503). Analysis of the individual cell surface expression of hIL2RA (CD25) variants was performed assessing the mean fluorescence intensity (MFI) as readout parameter.

Figure 2:
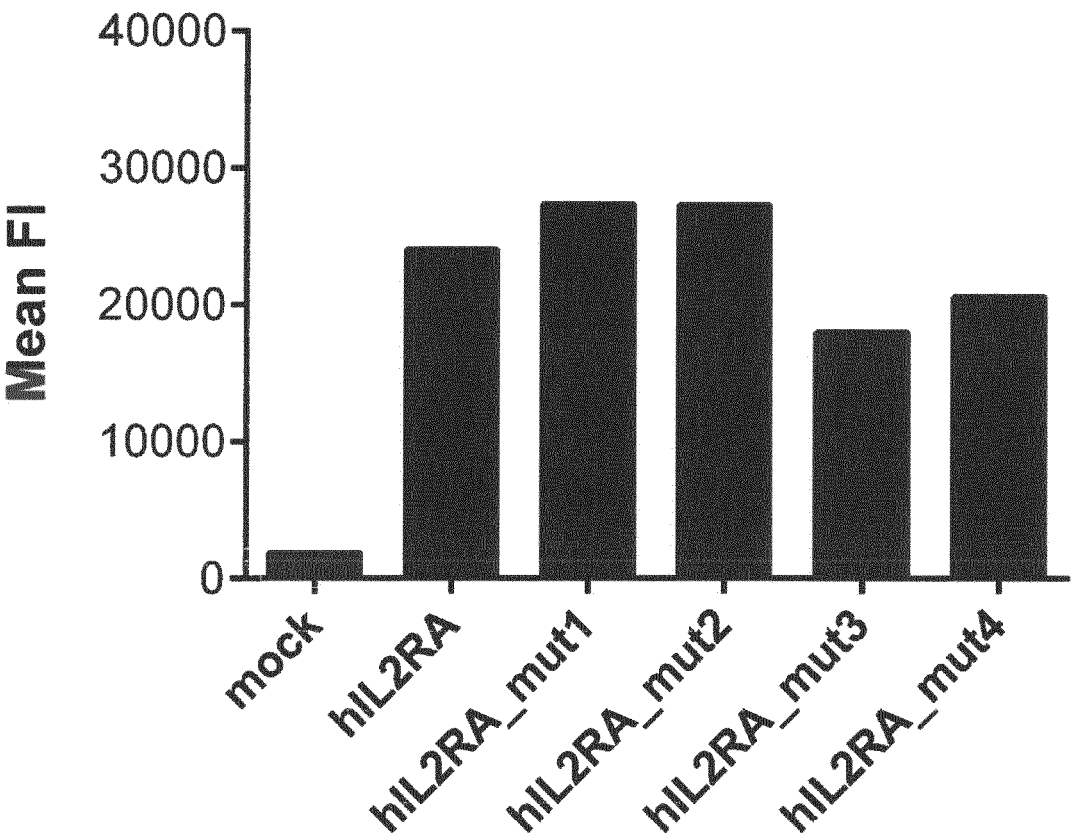
FIG. 2: In vitro expression of RNA-encoded hIL2RA (CD25) mutants in human primary CD8⁺ T cells. Human primary CD8⁺ T cells were isolated from PBMCs by MACS technology using anti-CD8 MicroBeads and $10 \times 10^6$ CD8⁺ T cells were electroporated with 15 μg of mRNA encoding the hIL2RA (CD25) mutants in 250 μL X-Vivo15 in a 4-mm electroporation cuvette at one 500 V, 3 ms pulse. After 20-24 h incubation at 37° C., 5% $CO_2$, cell surface expression of hIL2RA (CD25) mutants was checked by flow cytometry using PerCP-Cy™5.5 Mouse Anti-Human CD25 antibody. Data shown are mean fluorescence intensity (MFI) values of a single measurement.

Compared to the mock-electroporated CD8$^+$ T cells the MFI of hIL2RA or hIL2RA mutant electroporated CD8$^+$ T cells was elevated by a factor of ≥9-fold, (MFI of 1837 versus ≥17998; FIG. 2), hence proving successful surface expression of all hIL2RA constructs tested. Important to note, the expression levels of all hIL2RA constructs were in the same order of magnitude, ranging from an MFI of 17998 to 27352.

Example 5: Comparison of the Functional Activity of hAlb-hIL2 Variants on Naturally CD25-Expressing CD4$^+$CD25$^+$ Regulatory T Cells Compared to Primary CD8$^+$ T Cells Electroporated with hIL2RA (CD25) Measured by IL2-Mediated Phosphorylation of STAT5

In order to qualify isolated primary human CD8$^+$ T cells transfected with different hIL2RA mutants as an adequate model system to test the biological activity of different reciprocally designed hAlb-hIL2 variants, the bioactivity of two exemplary CD25-binding deficient hAlb-hIL2 variants (hAlb-hIL2_A3, hAlb-hIL2_A4) versus hAlb-hIL2 was analyzed on naturally CD25-expressing CD4$^+$CD25$^+$ regulatory T cells compared to autologous CD8$^+$ T cells electroporated with hIL2RA (CD25) via STAT5 phosphorylation read-out.

In a first step, CD8$^+$ T cells were isolated from PBMCs obtained from healthy donors (Transfusionszentrale, University Hospital, Mainz, Germany) by MACS technology using anti-CD8 MicroBeads according to the manufacturer's instructions. About 10×10$^6$ CD8$^+$ T cells were electroporated with 15 µg of IVT-mRNA encoding hIL2RA (CD25) in 250 µL X-Vivo15 as described in example 4 (500 V, 1×3 ms pulse). Immediately after electroporation, cells were transferred into fresh IMDM medium supplemented with 5% human AB serum and were rested at 37° C., 5% CO$_2$ overnight. The next day, autologous PBMCs were thawed, re-suspended in IMDM supplemented with 5% human AB serum and were rested for 2 h at 37° C. and 5% CO$_2$. After resting i.) 125,000 hIL2RA (CD25)-electroporated CD8$^+$ T cells, and ii) 125,000 PBMCs were seeded per well of a 96-well V-bottom plate (Greiner Bio-One GmbH, cat. no. 651101) in IMDM supplemented with 5% human AB serum. In parallel, eight six-fold serial dilutions of hAlb-hIL2 variant-containing supernatants were generated in IMDM supplemented with 5% human AB serum. Seeded cells were mixed 1:1 with hAlb-hIL2 variant supernatants and stimulated for 10 min at 37° C. and 5% CO$_2$. Next, 1:1,000 fixable viability dye eFluor™ 780 (eBioscience, cat. No. 65-0865-14) was added and the cells stimulated for another 5 min at 37° C. and 5% CO$_2$. The cells were fixed by addition of buffered formaldehyde (Cad Roth GmbH+Co. KG, cat. no. P087.4) to a final concentration of 2% and incubated for 10 min on ice. Fixed PBMCs/CD8$^+$ T cells were washed with ice cold D-PBS and permeabilized with 100% ice-cold methanol (Cad Roth, cat. no. 7342.2) for 30 min on ice. Permeabilized PBMCs/CD8$^+$ T cells were washed twice with D-PBS supplemented with 2% FBS and 2 mM EDTA and subsequently stained. hIL2RA (CD25)-electroporated CD8$^+$ T cells were stained with 1:10 Alexa Fluor® 488 Anti-Stat5 (pY694) (Becton Dickinson GmbH, cat. no. 612598) and 1:25 PerCP-Cy™5.5 Mouse Anti-Human CD25 in D-PBS supplemented with 2% FBS and 2 mM EDTA for 30 min at 2-8° C. protected from light; PBMCs were stained with 1:10 Alexa Fluor® 488 Anti-Stat5 (pY694), 1:25 PerCP-Cy™5.5 Mouse Anti-Human CD25, 1:50 BV421 Mouse Anti-Human CD4 (Becton Dickinson GmbH, cat. no. 565997) and 1:25 BV510 Mouse Anti-Human CD8 (Becton Dickinson GmbH, cat. no. 563256). Stained PBMCs/CD8$^+$ T cells were washed twice with and finally re-suspended in D-PBS supplemented with 2% FBS and 2 mM EDTA. Flow cytometric analysis was performed on a BD FACSCanto™ II flow cytometer (Becton Dickinson GmbH) and acquired data was analyzed using FlowJo software version 10. Dose-response curves were generated and EC$_{50}$ values were calculated in GraphPad Prism version 6.04 (GraphPad Software, Inc.).

Figure 3:
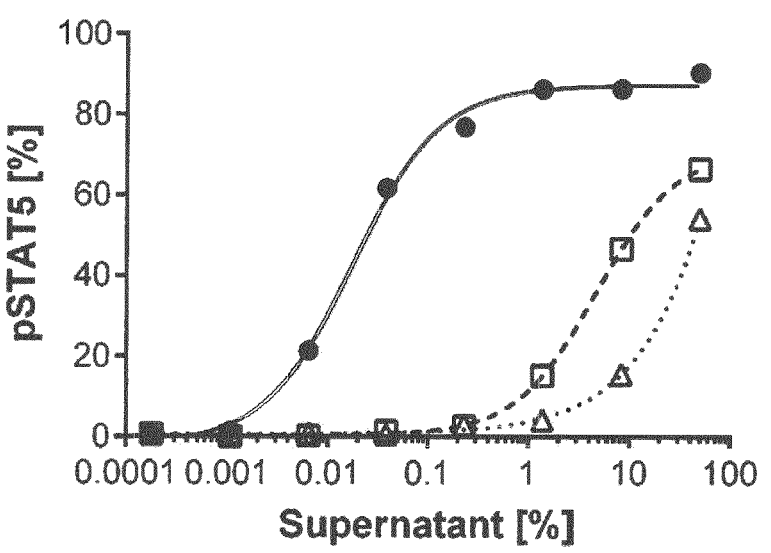
FIG. 3: Functional activity of hAlb-hIL2 variants on naturally CD25-expressing CD4⁺CD25⁺ regulatory T cells compared to CD8⁺ T cells electroporated with hIL2RA (CD25) measured by IL2-mediated phosphorylation of STAT5. Dose-response curves of STAT5 phosphorylation (pSTAT5) on CD4⁺CD25⁺ regulatory T cells (A) and CD8⁺ T cells transfected with hIL2RA (CD25) (B). PBMCs and CD8⁺ T cells transfected with hIL2RA (CD25) were incubated with serial dilutions of hAlb-hIL2 variant-containing supernatant and phosphorylation of STAT5 was subsequently analyzed via flow cytometry. Data shown are fitted with a four parameter logarithmic fit to calculate $EC_{50}$ values.
Figure 3:
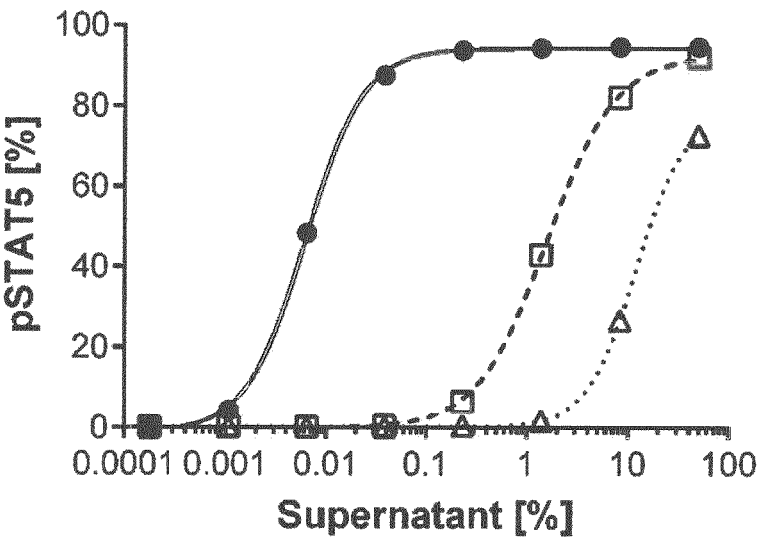
Figure 5:
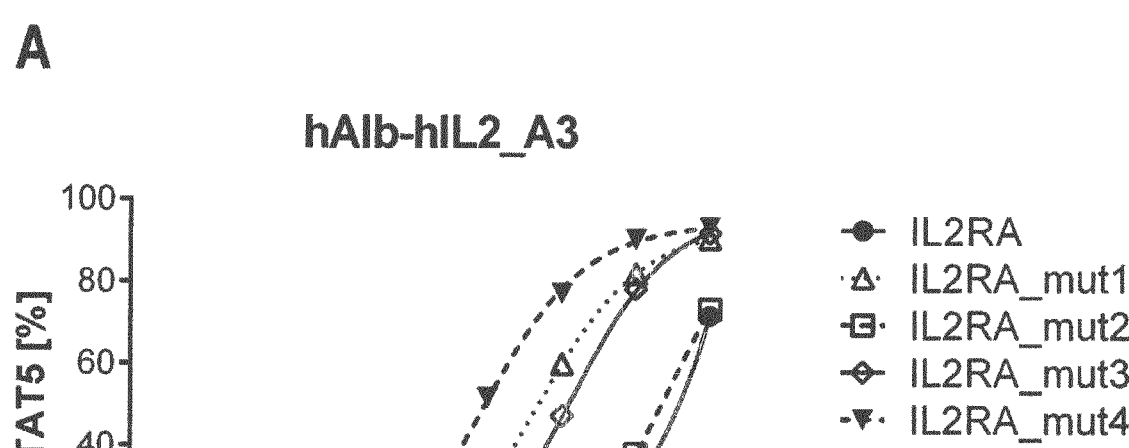
Figure 5:
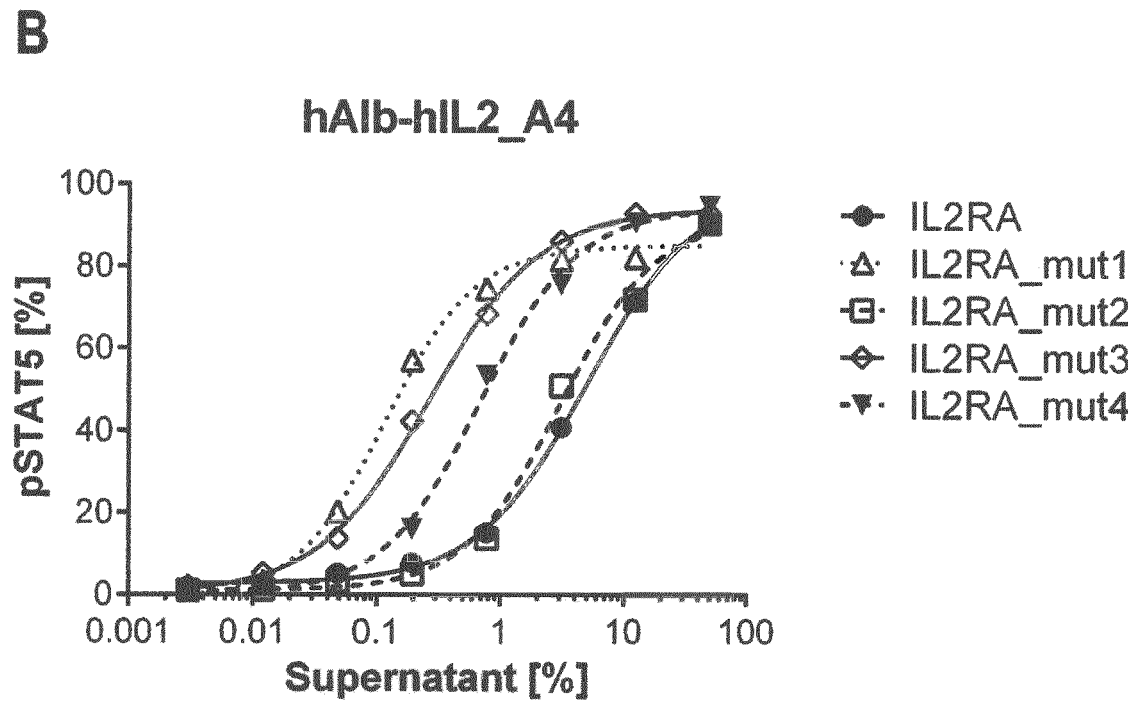
Figure 6:
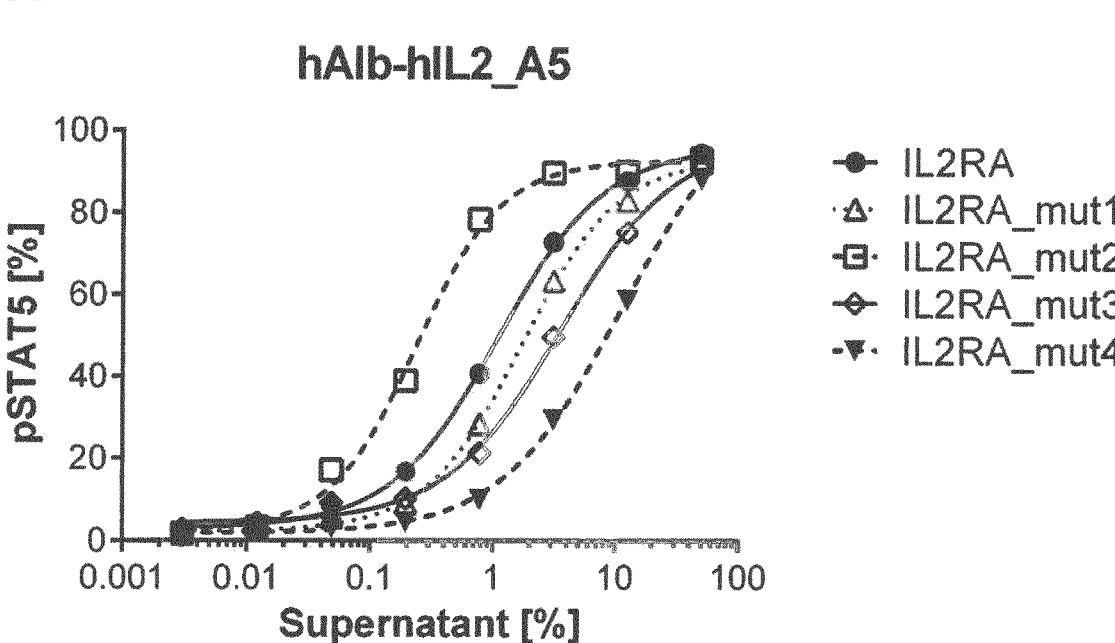
Figure 6:
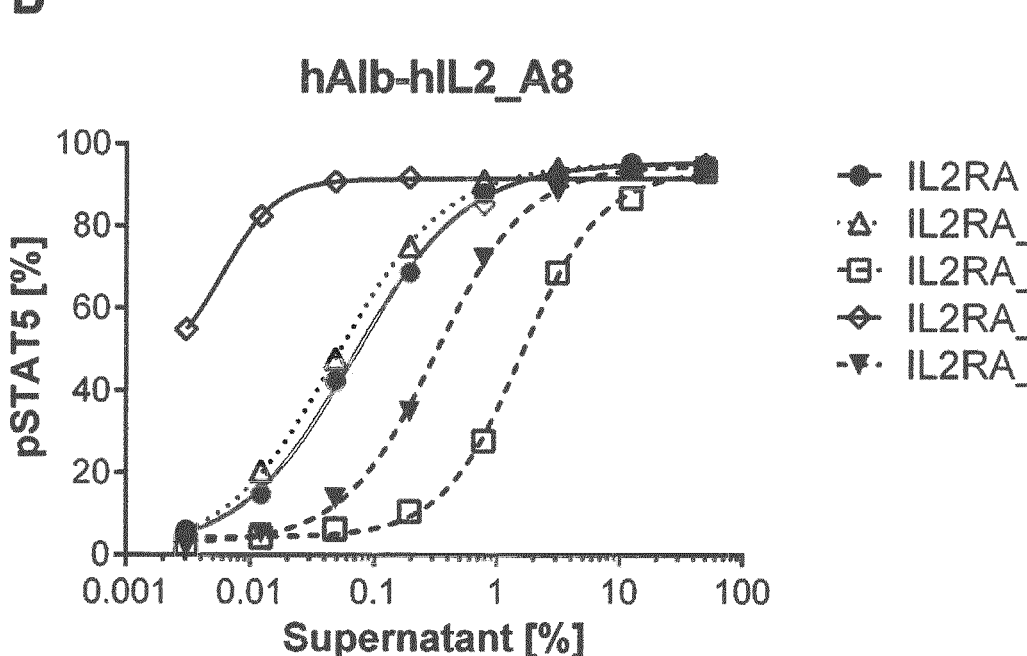

On both CD4$^+$CD25$^+$ regulatory T cells and hIL2RA (CD25) electroporated CD8$^+$ T cells hAlb-hIL2 displayed superior potency over both exemplarily tested hAlb-hIL2 variants with reduced CD25 binding affinity (hAlb-hIL2_A3, hAlb-hIL2_A4) (FIG. 3 and Tables 4, 5). In detail, the biological activity of hAlb-hIL2_A3 was strongly reduced by approx. 1718 to 1937-fold compared to hAlb-hIL2, whereas hAlb-hIL2A4 displayed an intermediate phenotype (255 to 269-fold reduced activity compared to hAlb-hIL2). Most importantly, even though the individual EC$_{50}$ values on natural CD25$^+$ regulatory T cells (FIG. 3 A) are ~3-fold higher when compared to the artificial hIL2RA (C25)-electroporated CD8$^+$ T cell population (FIG. 3B), the fold-difference in-between mutated variants hAlb-hIL2_A3/ A4 and hAlb-hIL2 is consistent throughout natural and artificial sub-populations. This finding qualifies hIL2RA (CD25) and hence also hIL2RA mutant electroporated CD8$^+$ T cells as an adequate surrogate population to test the biological activity of different reciprocally designed hAlb-hIL2 variants.

ity on CD8$^+$ T cells expressing the predicted matching hIL2RA mutant, namely hIL2RA_mut4 for hAlb-hIL2_A3 (EC$_{50}$ 0.663%-supernatant) and hIL2RA_mut1 for hAlb-hIL2_A4 (EC$_{50}$ 0.116%-supernatant) (FIG. 5 A, B and Table 6) outperformed all other hIL2RA mutants, thereby reflecting a high selectivity increase of approx. 74-fold for hAlb-hIL2_3 and 43-fold for hAlb-hIL2_A4 on hIL2RA mutant versus hIL2RA wild-type electroporated CD8$^+$ T cells (Table 7). Variant hAlb-hIL2_A5 with intermediate biological activity on hIL2RA expressing CD8'T cell cultures, displayed an approx. 5-fold increased selectivity for CD8$^+$ T cells transfected with the predicted hIL2RA_mut2 (EC$_{50}$ of 0.237%-supernatant vs. 1.106%-supernatant in hIL2RA_mut2-positive culture), while being less potent on all other hIL2RA mutants compared to hIL2RA wild-type (FIG. 6 A, Table 6 & 7). Likewise, also variant hAlb-hIL2_A8 showed an approx. 11-fold increase in selectivity only for CD8$^+$ T cells expressing the reciprocally designed hIL2RA_mut3 (Table 7) represented by an EC$_{50}$ value of

TABLE 4

EC$_{50}$ values [%-supernatant] calculated based on STAT5 phosphorylation dose-response for the hAlb-hIL2 variants on different T cell populations.

| hAlb-hIL2 variant | CD4$^+$CD25$^+$ regulatory T cells | hIL2RA-velectroporated CD8$^+$ T cells |
|---|---|---|
| hAlb-hIL2 | 0.01746 | 0.0062 |
| hAlb-hIL2_A3 | ~30 | 12.01 |
| hAlb-hIL2_A4 | 4.70 | 1.58 |

TABLE 5

The difference in biological activity in-between mutated hAlb-hIL2 variants and hAlb-hIL2 on natural vs. artificial CD25$^+$ T cell populations is given as fold-reduced potency of the hAlb-hIL2 variant compared to hAlb-hIL2. Fold-reduced potency was calculated as the ratio of individual EC$_{50}$ values for each hAlb-hIL2 variant versus the EC$_{50}$ value for hAlb-hIL2 on the respective T cell population.

| hAlb-hIL2 variant | CD4$^+$CD25$^+$ regulatory T cells | hIL2RA-electroporated CD8$^+$ T cells |
|---|---|---|
| hAlb-hIL2_A3 | ~1718 | 1937 |
| hAlb-hIL2_A4 | 269 | 255 |

Example 6: Comparison of the Functional Activity of hAlb-hIL2 Variants on Primary CD8$^+$ T Cells Electroporated with Different hIL2RA (CD25) Mutants Measured by IL2-Mediated Phosphorylation of STAT5

Figure 4:
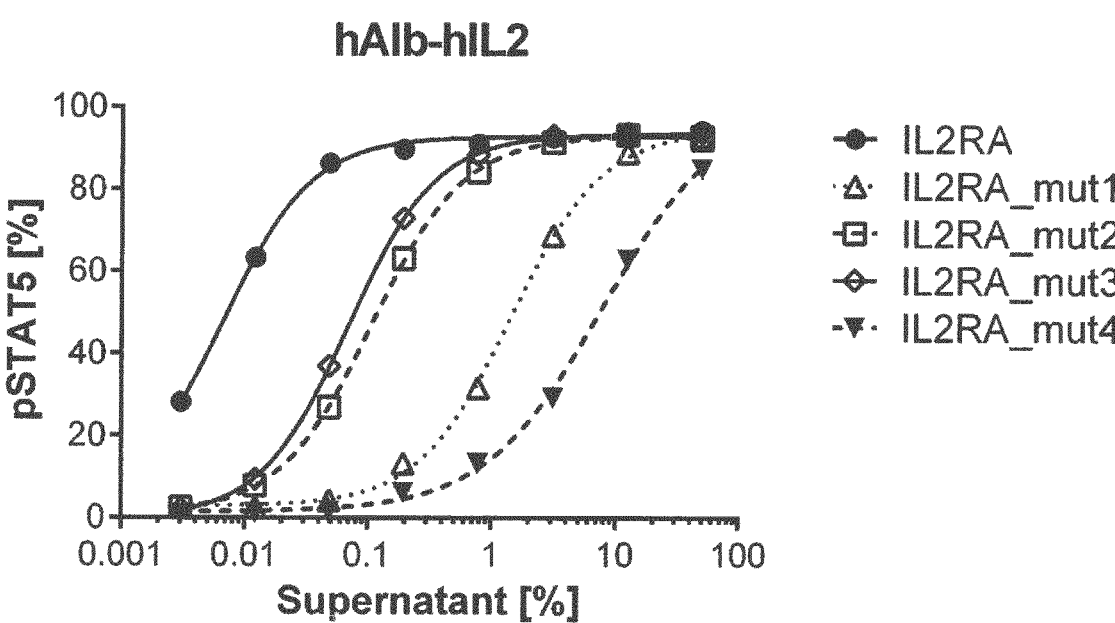
FIGS. 4, 5 and 6: Functional activity of hAlb-hIL2 variants on CD8⁺ T cells electroporated with different mutants of hIL2RA (CD25) measured by IL2-mediated phosphorylation of STAT5. Dose-response curves of STAT5 phosphorylation (pSTAT5) on CD8⁺ T cells transfected with hIL2RA (CD25) mutants is shown for hAlb-hIL2 (FIG. 4), hAlb-hIL2_A3 (FIG. 5, A), hAlb-hIL2_A4 (FIG. 5, B), hAlb-hIL2_A5 (FIG. 6, A) and hAlb-hIL2_A8 (FIG. 6, B). CD8 T cells were incubated with serial dilutions of hAlb-hIL2 variant-containing supernatant and phosphorylation of STAT5 was subsequently analyzed via flow cytometry. Data shown are from one representative experiment out of four and are fitted with a four parameter logarithmic fit to calculate $EC_{50}$ values.

Wild-type hAlb-hIL2 displayed highest biological activity on hIL2RA transfected CD8$^+$ T cells represented by an EC$_{50}$ value of 0.0067%-supernatant. With increasing number of mutations implemented in the hIL2RA mutants and hence incremental numbers of repulsive interactions, the biological activity of hAlb-hIL2 gradually declined approx. by factor 10 to 1000 with strongest reduction being present in CD8$^+$ T cells transfected with hIL2RA_mut4 (3 mutations; EC$_{50}$ of 7.76%-supernatant) (FIG. 4, Table 6). Compared to wild-type hAlb-hIL2 the variants hAlb-hIL2_A3 with three amino acid substitutions or hAlb-hIL2_A4 with two amino acid substitutions showed strongly decreased biological activity on hIL2RA wild-type electroporated CD8$^+$ T cells (EC$_{50}$ of 49.4 and 5.017%-supernatant, respectively), but both hAlb-hIL2 variants regained potency on CD8$^+$ T cell cultures expressing all various reciprocally designed hIL2RA mutants. Importantly, the biological activ- 0.0059%-supernatant compared to 0.0677%-supernatant on CD8$^+$ T cells electroporated with hIL2RA wild-type (FIG. 6 B, Table 6).

In summary, all predictions made for pairings of reciprocally designed hAlb-hIL2 variants and hIL2RA mutants (Table 1) were confirmed. The highest increase in selectivity of a hAlb-hIL2 variant for a reciprocally designed hIL2RA mutant was achieved in the pairing of hAlb-hL2_A4 with hIL2RA_mut1 and hAlb-hIL2_A3 with hIL2RA_mut4 where two or even three amino acid positions were reciprocally substituted, resulting in an approx. 43-fold resp. 75-fold increased potency on the mutated hIL2RA compared to hIL2RA wild-type. Both combinations concomitantly showed high biological activity with EC$_{50}$ values ranging between 0.1 and 0.6% supernatant. Of note, the biological activity of hAlb-hIL2_A8 on hIL2RA_mut3 expressing CD8$^+$ T cells even exceeded the levels of hAlb-hIL2 wild-type on CD8$^+$ T cells transfected with hIL2RA wild-type (EC$_{50}$ of 0.0059 vs. 0.0067%-supernatant, Table 6), but the selectivity for the mutant hIL2RA receptor was only increased by factor 10.

TABLE 6

EC$_{50}$ values [%-supernatant] calculated based on STAT5 phosphorylation dose-responses for the hAIb-hIL2 variants on CD8$^+$ T cells electroporated with different hIL2RA mutants.

| hAIb-hIL2 variant | hIL2RA | hIL2RA_mut1 | hIL2RA_mut2 | hIL2RA_mut3 | hIL2RA_mut4 |
|---|---|---|---|---|---|
| hAIb-hIL2 | 0.0067 | 1.427 | 0.107 | 0.069 | 7.76 |
| hAIb-hIL2_A3 | 49.4 | 1.795 | 31.66 | 3.717 | 0.663 |
| hAIb-hIL2_A4 | 5.017 | 0.116 | 3.059 | 0.265 | 0.694 |
| hAIb-hIL2_A5 | 1.106 | 1.725 | 0.237 | 3.539 | 11.01 |
| hAIb-hIL2_A8 | 0.0677 | 0.048 | 1.6 | 0.0059 | 0.315 |

TABLE 7

The selectivity towards the respective hIL2RA mutant of each hAIb-hIL2 variant is given as fold-increased potency on hIL2RA mutant versus hIL2RA wild-type electroporated CD8$^+$ T cells. Fold-increased potency was calculated as the ratio of individual EC$_{50}$ values for each hAIb-hIL2 variant determined on hIL2RA mutant electroporated CD8$^+$ T cells versus the EC$_{50}$ values determined on hIL2RA wild-type electroporated CD8$^+$ T cells.

| hAIb-hIL2 variant | hIL2RA_mut1 | hIL2RA_mut2 | hIL2RA_mut3 | hIL2RA_mut4 |
|---|---|---|---|---|
| hAIb-hIL2 | 0.005 | 0.063 | 0.097 | 0.001 |
| hAIb-hIL2_A3 | 27.52 | 1.560 | 13.29 | 74.35 |
| hAIb-hIL2_A4 | 43.10 | 1.64 | 18.96 | 7.231 |
| hAIb-hIL2_A5 | 0.641 | 4.659 | 0.313 | 0.101 |
| hAIb-hIL2_A8 | 1.407 | 0.042 | 11.43 | 0.215 |

Example 7: Effect of hAIb-hIL2 Variants on In Vitro Anti-Tumor Efficacy of CAR Redirected CD8$^+$ T Cells Electroporated with Different hIL2RA (CD25) Mutants To investigate the benefit of reciprocal systems on CAR T cell mediated cytotoxicity, an in vitro killing assay was set up comparing CAR T cells electroporated with either mutant or wild-type hIL2RA. CAR T cells were co-cultivated with PA-1 human ovarian cancer cell spheroids as targets. The PA-1 cell line was stably transfected with eGFP via lentiviral transduction to allow fluorescence-based live imaging. Co-cultures were set up in the presence of the corresponding reciprocal hAIb-hIL2 variant. The applied E:T ratio of 10:1 confers suboptimal cytotoxicity, therefore allowing to assess hAIb-hIL2 variant:hIL2RA mutant mediated enhanced killing.

In a first step, CD8$^+$ T cells were isolated from PBMCs obtained from healthy donors (Transfusionszentrale, University Hospital, Mainz, Germany) by MACS technology using anti-CD8 MicroBeads according to the manufacturer's instructions. $2 \times 10^6$ CD8$^+$ T cells per well were activated for 2 days in 24-well plates (VWR international, cat no. 701605) coated with 1 µg anti-CD3 antibody (Abcam plc, cat. no. ab86883) per well in the presence of 50 U/mL IL2 (Proleukin®S, Novartis Pharma, cat. no. 02238131). Next, the T cells were transferred to new 24-well plates with fresh medium containing 50 U/mL IL2, in order to rest for an additional 3 days prior to electroporation. About $10^7$ CD8$^+$ T cells were electroporated per 4-mm cuvette with 20 µg IVT-mRNA encoding a CLDN6-specific CAR construct containing the CD28-CD3zeta (ζ) chimeric cytoplasmic domain (28ζ) (Kofler et al. Mol Ther 2011), or 15 µg IVT-mRNA encoding a CLDN6-specific CAR construct containing the 41BB-ζ chimeric cytoplasmic domain (BBζ) (Reinhard et al. Science 2020) as described in example 4. CD8$^+$ T cells electroporated with 20 µg IVT-mRNA encoding a Claudin 18.2 (CLDN18.2)-specific CAR construct were used as negative control (mock CAR). All CAR constructs were electroporated in combination with 10 µg IVT-mRNA encoding hIL2RA, hIL2RA_mut1 or hIL2RA_mut4. Immediately after electroporation, cells were transferred into RPMI 1640 medium supplemented with 5% human AB serum and were rested at 37° C., 5% CO$_2$ overnight. The same day, CLDN6-positive PA-1 tumor cells (ATCC® CRL-1572™) were harvested from continuous culture using accutase (Sigma-Aldrich Chemie GmbH, cat no. A6964-100ML) and adjusted to $4 \times 10^5$ cells/mL in MEM Glutamax (Gibco, cat. no. 41090036) supplemented with 10% heat-inactivated FBS, 1 mM Sodium Pyruvate (Life Technologies GmbH, cat. no. 11360-039), 1% NEAA (Gibco, cat. no. 11140050) and 2% Sodium Bicarbonate (Gibco, cat. no. 25080094). 25 µL of PA-1 cell suspension were transferred per well into 96-well ultra-low attachment plates (Corning, cat. no. 7007) and incubated for 24 hours at 37° C. and 5% CO$_2$ to initiate tumor spheroid formation. The following day, surface expression of hIL2RA wild-type and mutants as well as CAR constructs on electroporated CD8$^+$ T cells was confirmed via flow cytometry using anti-CD25 (see Example 4) and custom-developed anti-CAR idiotype antibodies. Flow cytometric analysis was performed on a BD FACSCanto™ II flow cytometer and acquired data were analyzed using FlowJo software version 10. $10^5$ CAR- and hIL2RA-modified CD8$^+$ T cells per well were added to the PA-1 tumor spheroid cultures in 125 µL FluoroBrite DMEM medium (Thermo Fisher Scientific, cat. no. 15266695) supplemented with 5% human AB serum in technical triplicates. 50 µL of the respective hAIb-hIL2 variant-containing supernatants were added to the CAR T cell:tumor spheroid co-cultures, and the 96-well plates were transferred into an Incucyte S3 live cell imaging system (Essen Bioscience). hAIb-containing supernatants were used as a negative control. The fluorescence signal of eGFP positive PA-1 tumor spheroids was measured over 5 days as a surrogate marker for cell viability. The total green object area of each tumor spheroid triplicate was recorded and normalized to the respective spheroid area at the beginning of the co-culture. The cytotoxic effect on PA-1 tumor spheroids mediated by CAR T cells expressing the respective hIL2RA constructs was analyzed upon addition of the corresponding reciprocal hAlb-hIL2 variant and compared to CAR T cells electroporated with hIL2RA wild-type. Data for each CAR construct (CLDN18.2 CAR 28ζ, CLDN6 CAR 28ζ and CLDN6 CAR BB) are plotted separately in FIG. 7, FIG. 8 and FIG. 9, respectively.

Figure 8:
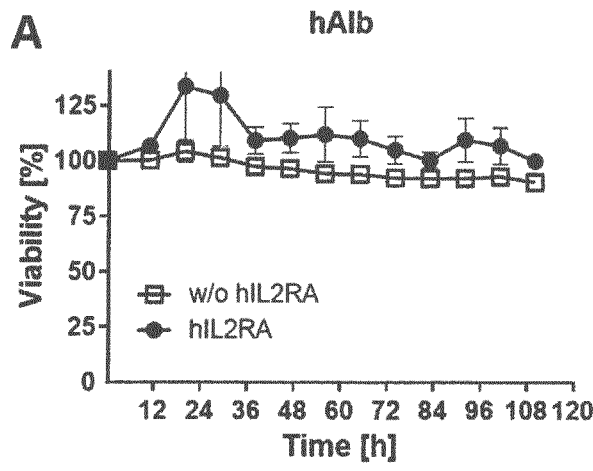
Figure 8:
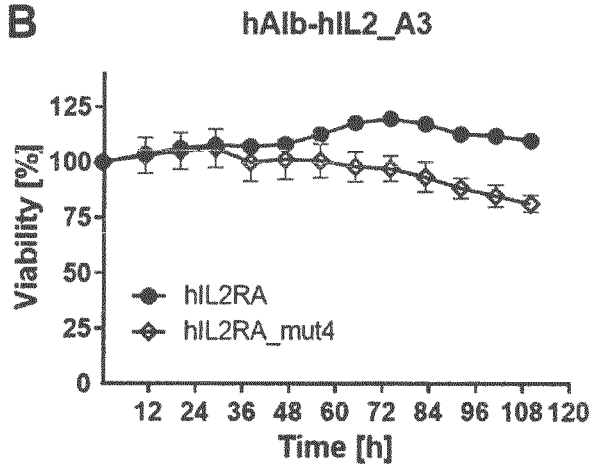
Figure 8:
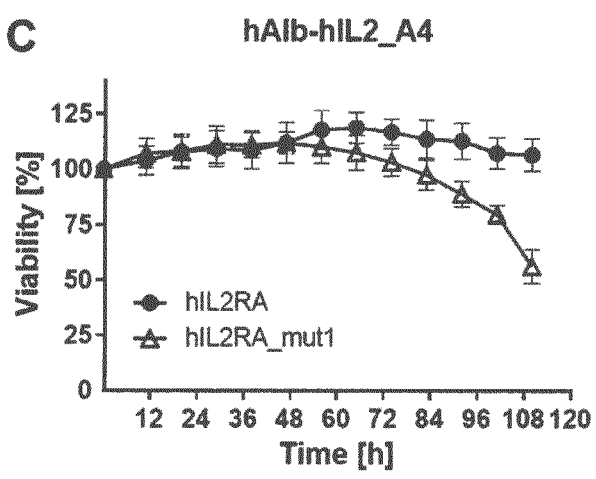
Figure 9:
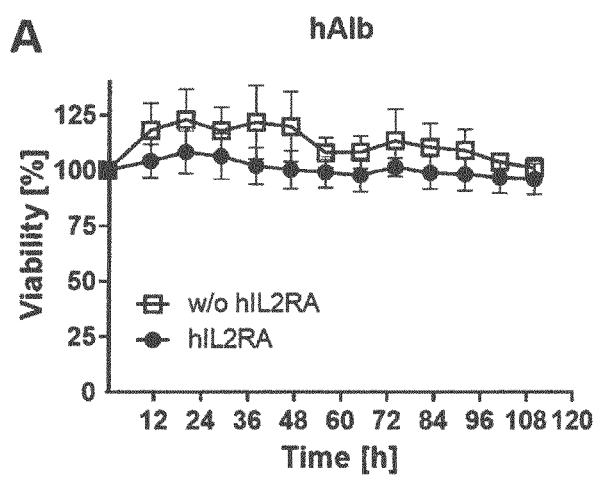
Figure 9:
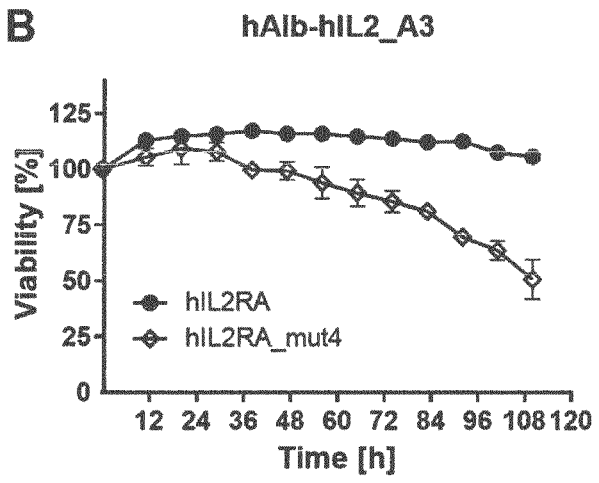

Independent of the hAlb-hIL2 variant or control supernatant applied, mock CAR (CLDN18.2 28ζ) containing co-cultures displayed no signs of CAR-mediated cytotoxicity (92 to 120% viability at the end of observation; FIG. 7A-C). Likewise, hAlb control supernatant treated CLDN6-specific CAR T cell (both CLDN6 28ζ and CLDN6 BBζ): PA-1 tumor spheroid co-cultures were not affected in their viability (90% to 101% viability at the end of observation; FIG. 8-9A). This is in line with the suboptimal number of CAR T cells applied to tumor spheroids. In contrast, the addition of both hAlb-hIL2_A3 and hAlb-hIL2_A4 to the corresponding reciprocal hIL2RA-electroporated CLDN6 28ζ CAR T cell containing co-cultures led to a selectively improved killing of PA-1 spheroids, since addition to hIL2RA wild-type electroporated CLDN6 CAR containing co-cultures was without any effect (FIG. 8B-C). In detail, hAlb-hIL2_A3 treatment resulted in a PA-1 tumor spheroid viability of 81% at the end of observation for the hIL2RA_mut4 co-electroporated CLDN6 28ζ CAR T cell containing co-cultures compared to 110% viability for the hIL2RA wild-type co-electroporated condition (FIG. 88). This is consistent with hAlb-hIL2_A4 treatment resulting in a PA-1 tumor spheroid viability of 56% at the end of observation for the hIL2RA_mut1 co-electroporated CLDN6 28ζ CAR T cell containing co-cultures compared to 107% viability for the hIL2RA wild-type co-electroporated condition (FIG. 8C). To work out the effect of hAlb-hIL2_A3 treatment more clearly, co-cultures containing T cells modified with the more potent CLDN6 BBC CAR construct were used. Thereby the hAlb-hIL2_A3 treatment resulted in a selectively improved killing of PA-1 tumor spheroids (51% viability at the end of observation) for the hIL2RA_mut4 co-electroporated CLDN6 BBC CAR T cell containing co-cultures compared to no reduction of spheroid viability for the hIL2RA wild-type co-electroporated condition (106% viability at the end of observation; FIG. 9B).

In conclusion, the tumor spheroid cytotoxicity assay data indicate that CAR T cell mediated cytotoxicity can be selectively augmented when CAR T cells are modified with an IL2RA mutant and treated with the corresponding reciprocal hAlb-hIL2 variant.

---

The invention claimed is:

1. A system comprising:
(i) a receptor polypeptide comprising a mutein of the alpha subunit of interleukin-2 receptor (IL2R), wherein the alpha subunit of IL2R has the amino acid sequence according to SEQ ID NO: 2 or 4, or of a functional variant of the alpha subunit of IL2R having at least 95% sequence identity to SEQ ID NO: 2 or 4 and having modifications only in positions which are not conserved between homologous IL2R amino acid sequences, wherein the alpha subunit of IL2R or the functional variant thereof is substituted at at least one position,
(ii) a ligand polypeptide comprising a mutein of IL2, wherein the IL2 has the amino acid sequence according to SEQ ID NO: 1, or of a functional variant of IL2 having at least 95% sequence identity to SEQ ID NO: 1 and having modifications only in positions which are not conserved between homologous IL2 amino acid sequences, wherein the IL2 or the functional variant thereof is substituted at at least one position,
wherein the substitutions are such that
  (a) the mutein under (ii) binds to and activates IL2R comprising the mutein under (i) as alpha subunit,
  (b) binding to and/or activation of IL2R comprising the mutein under (i) as alpha subunit by the mutein under (ii) exceeds binding to and/or activation of IL2R comprising the alpha subunit of IL2R or the functional variant thereof as alpha subunit by the mutein under (ii), and
  (c) acidic amino acid residues are substituted by basic amino acid residues and basic amino acid residues are substituted by acidic amino acid residues,
wherein
  (i) the alpha subunit of IL2R is the human alpha subunit of IL2R and the alpha subunit of IL2R or the functional variant thereof is substituted at at least position 1 (glutamic acid) relative to wild type human alpha subunit of IL2R according to SEQ ID NO: 2 and numbered in accordance with the wild type human alpha subunit of IL2R, and
  (ii) the IL2 is human IL2 and the IL2 or the functional variant thereof is substituted at at least position 35 (lysine) relative to wild type human IL2 according to SEQ ID NO: 1 and numbered in accordance with the wild type human IL2;
and/or
  (i) the alpha subunit of IL2R is the human alpha subunit of IL2R and the alpha subunit of IL2R or the functional variant thereof is substituted at at least position 29 (glutamic acid) relative to wild type human alpha subunit of IL2R and numbered in accordance with wild type human alpha subunit of IL2R, and
  (ii) the IL2 is human IL2 and the IL2 or the functional variant thereof is substituted at at least position 43 (lysine) relative to wild type human IL2 and numbered in accordance with wild type human IL2;
and/or
  (i) the alpha subunit of IL2R is the human alpha subunit of IL2R and the alpha subunit of IL2R or the functional variant thereof is substituted at at least position 38 (lysine) relative to wild type human alpha subunit of IL2R and numbered in accordance with wild type human alpha subunit of IL2R, and
  (ii) the IL2 is human IL2 and the IL2 or the functional variant thereof is substituted at at least position 61 (glutamic acid) relative to wild type human IL2 and numbered in accordance with wild type human IL2.

2. The system of claim 1, wherein
(a) binding to and/or activation of IL2R comprising the mutein under (i) as alpha subunit by the mutein under (ii) exceeds binding to and/or activation of IL2R comprising the mutein under (i) as alpha subunit by IL2 or the functional variant thereof, or

(b) binding to and/or activation of IL2R comprising the alpha subunit of IL2R or the functional variant thereof as alpha subunit by IL2 or the functional variant thereof exceeds binding to and/or activation of IL2R comprising the alpha subunit of IL2R or the functional variant thereof as alpha subunit by the mutein under (ii), or (c) binding to and/or activation of IL2R comprising the alpha subunit of IL2R or the functional variant thereof as alpha subunit by IL2 or the functional variant thereof exceeds binding to and/or activation of IL2R comprising the mutein under (i) as alpha subunit by IL2 or the functional variant thereof.

3. The system of claim 1, wherein (i) the alpha subunit of IL2R is the human alpha subunit of IL2R and the alpha subunit of IL2R or the functional variant thereof is substituted at at least position 1 (glutamic acid) by lysine, position 29 (glutamic acid) by lysine and position 38 (lysine) by glutamic acid relative to wild type human alpha subunit of IL2R and numbered in accordance with wild type human alpha subunit of IL2R, and (ii) the IL2 is human IL2 and the IL2 or the functional variant thereof is substituted at at least position 35 (lysine) by glutamic acid, position 43 (lysine) by glutamic acid and position 61 (glutamic acid) by lysine relative to wild type human IL2 and numbered in accordance with wild type human IL2;

or (i) the alpha subunit of IL2R is the human alpha subunit of IL2R and the alpha subunit of IL2R or the functional variant thereof is substituted at at least position 29 (glutamic acid) by lysine and position 38 (lysine) by glutamic acid relative to wild type human alpha subunit of IL2R and numbered in accordance with wild type human alpha subunit of IL2R, and (ii) the IL2 is human IL2 and the IL2 or the functional variant thereof is substituted at at least position 43 (lysine) by glutamic acid and position 61 (glutamic acid) by lysine relative to wild type human IL2 and numbered in accordance with wild type human IL2;

or (i) the alpha subunit of IL2R is the human alpha subunit of IL2R and the alpha subunit of IL2R or the functional variant thereof is substituted at at least position 38 (lysine) by glutamic acid relative to wild type human alpha subunit of IL2R and numbered in accordance with wild type human alpha subunit of IL2R, and (ii) the IL2 is human IL2 and the IL2 or the functional variant thereof is substituted at at least position 61 (glutamic acid) by lysine relative to wild type human IL2 and numbered in accordance with wild type human IL2;

or (i) the alpha subunit of IL2R is the human alpha subunit of IL2R and the alpha subunit of IL2R or the functional variant thereof is substituted at at least position 29 (glutamic acid) by lysine relative to wild type human alpha subunit of IL2R and numbered in accordance with wild type human alpha subunit of IL2R, and (ii) the IL2 is human IL2 and the IL2 or the functional variant thereof is substituted at at least position 43 (lysine) by glutamic acid relative to wild type human IL2 and numbered in accordance with wild type human IL2;

or (i) the alpha subunit of IL2R is the human alpha subunit of IL2R and the alpha subunit of IL2R or the functional variant thereof is substituted at at least position 29 (glutamic acid) by lysine and position 38 (lysine) by glutamic acid relative to wild type human alpha subunit of IL2R and numbered in accordance with wild type human alpha subunit of IL2R, and (ii) the IL2 is human IL2 and the IL2 or the functional variant thereof is substituted at at least position 35 (lysine) by glutamic acid, position 43 (lysine) by glutamic acid and position 61 (glutamic acid) by lysine relative to wild type human IL2 and numbered in accordance with wild type human IL2;

or (i) the alpha subunit of IL2R is the human alpha subunit of IL2R and the alpha subunit of IL2R or the functional variant thereof is substituted at at least position 29 (glutamic acid) by lysine relative to wild type human alpha subunit of IL2R and numbered in accordance with wild type human alpha subunit of IL2R, and (ii) the IL2 is human IL2 and the IL2 or the functional variant thereof is substituted at at least position 43 (lysine) by glutamic acid and position 61 (glutamic acid) by lysine relative to wild type human IL2 and numbered in accordance with wild type human IL2.

4. The system of claim 1, wherein the substitution in IL2 or the functional variant thereof reduces the affinity for IL2R comprising the wild type alpha subunit of IL2R as alpha subunit (IL2Rαβγ), and/or
wherein the substitution in IL2 or the functional variant thereof reduces the affinity for IL2R comprising the wild type alpha subunit of IL2R as alpha subunit (IL2Rαβγ) to a greater extent than for the βγ IL2 receptor complex (IL2Rβγ).

5. The system of claim 1, wherein the mutein under (ii) has a decreased ability to stimulate regulatory T cells compared to wild type IL2, and/or wherein the mutein under (ii) further comprises one or more amino acid substitutions which enhance the affinity for IL2Rβγ.

6. The system of claim 1, wherein the mutein under (ii) further comprises one or more amino acid substitutions which enhance the affinity for IL2Rβγ.

7. The system of claim 6, wherein the one or more amino acid substitutions which enhance the affinity for IL2Rβγ comprise the following set of substitutions: 80F, 81D, 85V, 86V, 92F.

8. The system of claim 1, wherein the ligand polypeptide is an extended pharmacokinetic (PK) polypeptide.

9. The system of claim 1, wherein the modifications in the functional variant of the alpha subunit of IL2R and in the functional variant of IL2 are conservative amino acid substitutions.

10. The system of claim 1, wherein the functional variant of the alpha subunit of IL2R and in the functional variant of IL2 each have 5 or fewer substitutions.

11. The system of claim 9, wherein the functional variant of the alpha subunit of IL2R and in the functional variant of IL2 each have 5 or fewer substitutions.

12. A system comprising:

(i) a receptor polypeptide comprising a mutein of the alpha subunit of interleukin-2 receptor (IL2R), wherein the alpha subunit of IL2R has the amino acid sequence according to SEQ ID NO: 2 or 4, or of a functional variant of the alpha subunit of IL2R having at least 95% sequence identity to SEQ ID NO: 2 or 4 and having only modifications which are conservative substitutions, wherein the alpha subunit of IL2R or the functional variant thereof is substituted at at least one position, (ii) a ligand polypeptide comprising a mutein of IL2, wherein the IL2 has the amino acid sequence according to SEQ ID NO: 1, or of a functional variant of IL2 having at least 95% sequence identity to SEQ ID NO: 1 and having only modifications which are conservative substitutions, wherein the IL2 or the functional variant thereof is substituted at at least one position, wherein the substitutions are such that (a) the mutein under (ii) binds to and activates IL2R comprising the mutein under (i) as alpha subunit, (b) binding to and/or activation of IL2R comprising the mutein under (i) as alpha subunit by the mutein under (ii) exceeds binding to and/or activation of IL2R comprising the alpha subunit of IL2R or the functional variant thereof as alpha subunit by the mutein under (ii), and (c) acidic amino acid residues are substituted by basic amino acid residues and basic amino acid residues are substituted by acidic amino acid residues, wherein (i) the alpha subunit of IL2R is the human alpha subunit of IL2R and the alpha subunit of IL2R or the functional variant thereof is substituted at at least position 1 (glutamic acid) relative to wild type human alpha subunit of IL2R according to SEQ ID NO: 2 and numbered in accordance with the wild type human alpha subunit of IL2R, and (ii) the IL2 is human IL2 and the IL2 or the functional variant thereof is substituted at at least position 35 (lysine) relative to wild type human IL2 according to SEQ ID NO: 1 and numbered in accordance with the wild type human IL2;

and/or (i) the alpha subunit of IL2R is the human alpha subunit of IL2R and the alpha subunit of IL2R or the functional variant thereof is substituted at at least position 29 (glutamic acid) relative to wild type human alpha subunit of IL2R and numbered in accordance with wild type human alpha subunit of IL2R, and (ii) the IL2 is human IL2 and the IL2 or the functional variant thereof is substituted at at least position 43 (lysine) relative to wild type human IL2 and numbered in accordance with wild type human IL2;

and/or (i) the alpha subunit of IL2R is the human alpha subunit of IL2R and the alpha subunit of IL2R or the functional variant thereof is substituted at at least position 38 (lysine) relative to wild type human alpha subunit of IL2R and numbered in accordance with wild type human alpha subunit of IL2R, and (ii) the IL2 is human IL2 and the IL2 or the functional variant thereof is substituted at at least position 61 (glutamic acid) relative to wild type human IL2 and numbered in accordance with wild type human IL2.

13. The system of claim 12, wherein the functional variant of the alpha subunit of IL2R and in the functional variant of IL2 each have 5 or fewer substitutions.

14. A system comprising:

(i) a receptor polypeptide comprising a mutein of the alpha subunit of interleukin-2 receptor (IL2R), wherein the alpha subunit of IL2R has the amino acid sequence according to SEQ ID NO: 2 or 4, or of a functional variant of the alpha subunit of IL2R having 5 or fewer substitutions to SEQ ID NO: 2 or 4, wherein the alpha subunit of IL2R or the functional variant thereof is substituted at at least one position, (ii) a ligand polypeptide comprising a mutein of IL2, wherein the IL2 has the amino acid sequence according to SEQ ID NO: 1, or of a functional variant of IL2 having 5 or fewer substitutions, wherein the IL2 or the functional variant thereof is substituted at at least one position, wherein the substitutions are such that (a) the mutein under (ii) binds to and activates IL2R comprising the mutein under (i) as alpha subunit, (b) binding to and/or activation of IL2R comprising the mutein under (i) as alpha subunit by the mutein under (ii) exceeds binding to and/or activation of IL2R comprising the alpha subunit of IL2R or the functional variant thereof as alpha subunit by the mutein under (ii), and (c) acidic amino acid residues are substituted by basic amino acid residues and basic amino acid residues are substituted by acidic amino acid residues, wherein (i) the alpha subunit of IL2R is the human alpha subunit of IL2R and the alpha subunit of IL2R or the functional variant thereof is substituted at at least position 1 (glutamic acid) relative to wild type human alpha subunit of IL2R according to SEQ ID NO: 2 and numbered in accordance with the wild type human alpha subunit of IL2R, and (ii) the IL2 is human IL2 and the IL2 or the functional variant thereof is substituted at at least position 35 (lysine) relative to wild type human IL2 according to SEQ ID NO: 1 and numbered in accordance with the wild type human IL2;

and/or (i) the alpha subunit of IL2R is the human alpha subunit of IL2R and the alpha subunit of IL2R or the functional variant thereof is substituted at at least position 29 (glutamic acid) relative to wild type human alpha subunit of IL2R and numbered in accordance with wild type human alpha subunit of IL2R, and (ii) the IL2 is human IL2 and the IL2 or the functional variant thereof is substituted at at least position 43 (lysine) relative to wild type human IL2 and numbered in accordance with wild type human IL2;

and/or (i) the alpha subunit of IL2R is the human alpha subunit of IL2R and the alpha subunit of IL2R or the functional variant thereof is substituted at at least position 38 (lysine) relative to wild type human alpha subunit of IL2R and numbered in accordance with wild type human alpha subunit of IL2R, and (ii) the IL2 is human IL2 and the IL2 or the functional variant thereof is substituted at at least position 61 (glutamic acid) relative to wild type human IL2 and numbered in accordance with wild type human IL2.

15. The system of claim 14, wherein the functional variant of the alpha subunit of IL2R and in the functional variant of IL2 each have 4 or fewer substitutions.

16. The system of claim 14, wherein the functional variant of the alpha subunit of IL2R and in the functional variant of IL2 each have 3 or fewer substitutions.

\* \* \* \* \*